US009855328B2

(12) United States Patent
Tang et al.

(10) Patent No.: US 9,855,328 B2
(45) Date of Patent: Jan. 2, 2018

(54) IMMUNIZATION OF AVIANS BY ADMINISTRATION OF NON-REPLICATING VECTORED VACCINES

(71) Applicants: AUBURN UNIVERSITY, Auburn, AL (US); ALTIMMUNE INC., Gaithersburg, MD (US)

(72) Inventors: De-Chu C. Tang, Birmingham, AL (US); Kent R. Van Kampen, Birmingham, AL (US); Haroldo Toro, Auburn, AL (US)

(73) Assignees: AUBURN UNIVERSITY, Auburn, AL (US); ALTIMMUNE INC., Gaithersburg, MD (US)

(*) Notice: Subject to any disclaimer, the term of this patent is extended or adjusted under 35 U.S.C. 154(b) by 0 days.

(21) Appl. No.: 14/020,024

(22) Filed: Sep. 6, 2013

(65) Prior Publication Data

US 2014/0037679 A1 Feb. 6, 2014

Related U.S. Application Data

(63) Continuation of application No. 11/504,152, filed on Aug. 15, 2006, now abandoned.

(60) Provisional application No. 60/708,524, filed on Aug. 15, 2005.

(51) Int. Cl.
| | | |
|---|---|---|
| *C12N 15/33* | (2006.01) | |
| *C12N 15/44* | (2006.01) | |
| *C12N 15/63* | (2006.01) | |
| *C12N 15/861* | (2006.01) | |
| *A61K 39/145* | (2006.01) | |
| *C07K 14/005* | (2006.01) | |
| *C12N 7/00* | (2006.01) | |
| *C12N 15/86* | (2006.01) | |
| *A61K 39/12* | (2006.01) | |
| *A61K 39/00* | (2006.01) | |

(52) U.S. Cl.
CPC ........... *A61K 39/145* (2013.01); *A61K 39/12* (2013.01); *C07K 14/005* (2013.01); *C12N 7/00* (2013.01); *C12N 15/86* (2013.01); *A61K 2039/5256* (2013.01); *A61K 2039/54* (2013.01); *A61K 2039/55* (2013.01); *A61K 2039/552* (2013.01); *A61K 2039/6075* (2013.01); *C12N 2710/10322* (2013.01); *C12N 2710/10343* (2013.01); *C12N 2760/16122* (2013.01); *C12N 2760/16134* (2013.01)

(58) Field of Classification Search
CPC .......... A61K 39/145; A61K 2039/5256; A61K 2039/54; A61K 2039/55; A61K 2039/552; A61K 2039/6075; C12N 15/86; C12N 2710/10241; C12N 2710/10321
USPC ...... 424/199.1, 233.1, 93.2, 209.1; 435/320.1
See application file for complete search history.

(56) References Cited

U.S. PATENT DOCUMENTS

| 6,716,823 B1 | 4/2004 | Tang et al. | |
|---|---|---|---|
| 2007/0003576 A1* | 1/2007 | Gambotto et al. | ......... 424/209.1 |
| 2008/0187557 A1* | 8/2008 | Sambhara et al. | ......... 424/233.1 |

FOREIGN PATENT DOCUMENTS

| AU | 2005201381 | 4/2005 |
|---|---|---|
| WO | 01/19968 | 3/2001 |
| WO | 03/070920 | 8/2003 |
| WO | 2006/063101 | 6/2006 |
| WO | 2006/113214 | 10/2006 |
| WO | WO 2006/113214 | * 10/2006 |
| WO | 2006/127956 | 11/2006 |

OTHER PUBLICATIONS

Fallaux et al. (1998) Human Gene Therapy, vol. 9(13), 1909-1917.*
Ding et al. (2005) Vaccine, vol. 23, 3733-3740.*
Adam et al. (1995) J. Gen. Virol., vol. 76, 3153-3157.*
Francois et al. (2004) Vaccine, vol. 22, 2351-2360.*
Webster et al. (1991) Vaccine, vol. 9, 303-308.*
Takahashi et al. (1998) Development, vol. 125, 1627-1635.*
McGrory et al. (1988) Virology, vol. 163(2) 614-617.*
Adam et al. "Replication-defective adenovirus type 5 as an in vitro and in vivo gene transfer vector in chickens" J. Gen. Virol., 1995, 76(12):3153-3157.
Fallaux et al. "New Helper Cells and Matched Early Region 1-Deleted Adenovirus Vectors Prevent Generation of Replication-Competent Adenoviruses" Human Gene Therapy, Sep. 1998, 9(13)1909-1917.
Gao, et al., "A Protective Vaccine for the Rapid Response to Pandemic Avian Influenza", Molecular Therapy, 2005, 11(Supplement 1):S27.
Gao, et al., "Protection of Mice and Poultry From Lethal H5N1 Influenza Virus Through Adenovirus-Based Immunization", Journal of Virology, 2006, 80(4):1959-1964.
He, et al. "A simplified system for generating recombinant adenoviruses" PNAS, Mar. 1998, 95:2509-2514.
Hoelscher, et al., "Development of Adenoviral-Vector-Based Pandemic Influenza Vaccine Against Antigenically Distinct Human H5N1 Strains in Mice" Lancet, 2006, 367:475-481.
Takahashi et al. "Adenovirus-mediated ectopic expression of Msx2 in even-numbered rhombomeres induces apoptotic elimination of cranial neural crest cells in ovo" Development, Apr. 1998, 125:1627-1635.
Tian, et al., "Protective Efficacy in Chickens, Geese and Ducks of an H5N1-inactivated Vaccine Developed by Reverse Genetics" Virology, 2005, 341:153-162.

(Continued)

*Primary Examiner* — Anne Marie S Wehbe
(74) *Attorney, Agent, or Firm* — Vedder Price P.C.; Thomas J. Kowalski; Deborah L. Lu

(57) ABSTRACT

The present invention relates generally to the fields of immunology and vaccine technology. More specifically, the invention relates to recombinant human adenovirus vectors for delivery of avian immunogens and antigens, such as avian influenza into avians. The invention also provides methods of introducing and expressing an avian immunogen in avian subjects, including avian embryos, as well as methods of eliciting an immunogenic response in avian subjects to avian immunogens.

19 Claims, 7 Drawing Sheets

(56) References Cited

OTHER PUBLICATIONS

Toro, et al., Protective Avian Influenza in Ovo Vaccination With Non-Replicating Human Adenovirus Vector, Vaccine, 2007, 25:2886-2891.
Webster, et al., "Efficacy of Nucleoprotein and Haemagglutinin Antigens Expressed in Fowlpox Virus as Vaccine for Influenza in Chickens", Vaccine, 1991, 9:303-308.
Wesley, et al., "Protection of Weaned Pigs by Vaccination With Human Adenovirus 5 Recombinant Viruses Expressing the Hemagglutinin and the Nucleoprotein of H3N2 Swine Influenza Virus", Vaccine, 2004, 22:3427-3434.

* cited by examiner

FIGURE 6

SEQUENCE LISTING

```
<160> NUMBER OF SEQ ID NOS: 10

<210> SEQ ID NO 1
<211> LENGTH: 1701
<212> TYPE: DNA
<213> ORGANISM: Influenza A virus
<220> FEATURE:
<221> NAME/KEY: CDS
<222> LOCATION: (1)..(1701)
<220> FEATURE:
<221> NAME/KEY: misc_feature
<222> LOCATION: (1)..(1701)
<223> OTHER INFORMATION: Influenza virus A/Panama/2007/1999(H3N2)
      hemagglutinin(HA)gene GeneBank DQ508865

<400> SEQUENCE: 1 atg aag act atc att gct ttg agc tac att tta tgt ctg gtt ttc gct       48
Met Lys Thr Ile Ile Ala Leu Ser Tyr Ile Leu Cys Leu Val Phe Ala
1               5                   10                  15 caa aaa ctt ccc gga aat gac aac agc acg gca acg ctg tgc ctg ggg       96
Gln Lys Leu Pro Gly Asn Asp Asn Ser Thr Ala Thr Leu Cys Leu Gly
            20                  25                  30 cac cat gca gtg tca aac gga acg cta gtg aaa aca atc acg aat gac      144
His His Ala Val Ser Asn Gly Thr Leu Val Lys Thr Ile Thr Asn Asp
        35                  40                  45 caa att gaa gtg act aat gct act gag ctg gtt cag agt tcc tca aca      192
Gln Ile Glu Val Thr Asn Ala Thr Glu Leu Val Gln Ser Ser Ser Thr
    50                  55                  60 ggt aga ata tgc gac agt cct cac caa atc ctt gat gga gaa aac tgc      240
Gly Arg Ile Cys Asp Ser Pro His Gln Ile Leu Asp Gly Glu Asn Cys
65                  70                  75                  80 aca cta ata gat gct cta ttg gga gac cct cat tgt gat ggc ttc caa      288
Thr Leu Ile Asp Ala Leu Leu Gly Asp Pro His Cys Asp Gly Phe Gln
```

-continued

|   |   |   | 85 |   |   |   | 90 |   |   |   | 95 |   |   |     |
|---|---|---|----|---|---|---|----|---|---|---|----|---|---|-----|
| aat | aag | gaa | tgg | gac | ctt | ttt | gtt | gaa | cgc | agc | aaa | gcc | tac | agc | aac | 336 |
| Asn | Lys | Glu | Trp | Asp | Leu | Phe | Val | Glu | Arg | Ser | Lys | Ala | Tyr | Ser | Asn |  |
|   |   |   | 100 |   |   |   | 105 |   |   |   | 110 |   |   |  |

```
aat aag gaa tgg gac ctt ttt gtt gaa cgc agc aaa gcc tac agc aac      336
Asn Lys Glu Trp Asp Leu Phe Val Glu Arg Ser Lys Ala Tyr Ser Asn
            100                 105                 110 tgt tac cct tat gat gtg ccg gat tat gcc tcc ctt agg tca cta gtt      384
Cys Tyr Pro Tyr Asp Val Pro Asp Tyr Ala Ser Leu Arg Ser Leu Val
            115                 120                 125 gcc tca tcc ggc aca ctg gag ttt aac aat gaa agc ttc aat tgg act      432
Ala Ser Ser Gly Thr Leu Glu Phe Asn Asn Glu Ser Phe Asn Trp Thr
130                 135                 140 gga gtc gct cag aat gga aca agc tct gct tgc aaa agg aga tct aat      480
Gly Val Ala Gln Asn Gly Thr Ser Ser Ala Cys Lys Arg Arg Ser Asn
145                 150                 155                 160 aaa agt ttc ttt agt aga ttg aat tgg ttg cac caa tta aaa tac aaa      528
Lys Ser Phe Phe Ser Arg Leu Asn Trp Leu His Gln Leu Lys Tyr Lys
            165                 170                 175 tat cca gca ctg aac gtg act atg cca aac aat gaa aaa ttt gac aaa      576
Tyr Pro Ala Leu Asn Val Thr Met Pro Asn Asn Glu Lys Phe Asp Lys
            180                 185                 190 ttg tac att tgg ggg gtt cac cac ccg agt acg gac agt gac caa atc      624
Leu Tyr Ile Trp Gly Val His His Pro Ser Thr Asp Ser Asp Gln Ile
            195                 200                 205 agc ata tat gct caa gca tca ggg aga gtc aca gtc tct acc aaa aga      672
Ser Ile Tyr Ala Gln Ala Ser Gly Arg Val Thr Val Ser Thr Lys Arg
210                 215                 220 agc caa caa act gta atc ccg aat atc gga tct agt ccc tgg gta agg      720
Ser Gln Gln Thr Val Ile Pro Asn Ile Gly Ser Ser Pro Trp Val Arg
225                 230                 235                 240 ggt gtc tcc agc aga ata agc atc tat tgg aca ata gta aaa ccg gga      768
Gly Val Ser Ser Arg Ile Ser Ile Tyr Trp Thr Ile Val Lys Pro Gly
            245                 250                 255 gac ata ctt ttg att aac agc aca ggg aat cta att gct cct cgg ggt      816
Asp Ile Leu Leu Ile Asn Ser Thr Gly Asn Leu Ile Ala Pro Arg Gly
            260                 265                 270 tac ttc aaa ata cga agt ggg aaa agc tca ata atg agg tca gat gca      864
Tyr Phe Lys Ile Arg Ser Gly Lys Ser Ser Ile Met Arg Ser Asp Ala
            275                 280                 285 ccc att ggc aaa tgt aat tct gaa tgc atc act cca aat gga agc att      912
Pro Ile Gly Lys Cys Asn Ser Glu Cys Ile Thr Pro Asn Gly Ser Ile
290                 295                 300 ccc aat gac aaa cca ttt caa aat gta aac agg atc aca tat ggg gcc      960
Pro Asn Asp Lys Pro Phe Gln Asn Val Asn Arg Ile Thr Tyr Gly Ala
305                 310                 315                 320 tgt ccc aga tat gtt aag caa aac act ctg aaa ttg gca aca ggg atg     1008
Cys Pro Arg Tyr Val Lys Gln Asn Thr Leu Lys Leu Ala Thr Gly Met
            325                 330                 335 cgg aat gta cca gag aaa caa act aga ggc ata ttc ggc gca atc gcg     1056
Arg Asn Val Pro Glu Lys Gln Thr Arg Gly Ile Phe Gly Ala Ile Ala
            340                 345                 350 ggt ttc ata gaa aat ggt tgg gag gga atg gtg gac ggt tgg tac ggt     1104
Gly Phe Ile Glu Asn Gly Trp Glu Gly Met Val Asp Gly Trp Tyr Gly
            355                 360                 365 ttc agg cat caa aat tct gag ggc aca gga caa gca gca gat ctt aaa     1152
Phe Arg His Gln Asn Ser Glu Gly Thr Gly Gln Ala Ala Asp Leu Lys
370                 375                 380 agc act caa gca gca atc aac caa atc aac ggg aaa ctg aat agg tta     1200
Ser Thr Gln Ala Ala Ile Asn Gln Ile Asn Gly Lys Leu Asn Arg Leu
385                 390                 395                 400 atc gag aaa acg aac gag aaa ttc cat caa att gaa aaa gaa ttc tca     1248
```

-continued

```
                Ile Glu Lys Thr Asn Glu Lys Phe His Gln Ile Glu Lys Glu Phe Ser
                                405                 410                 415 gaa gta gaa ggg aga att cag gac ctc gag aaa tat gtt gag gac act      1296
Glu Val Glu Gly Arg Ile Gln Asp Leu Glu Lys Tyr Val Glu Asp Thr
            420                 425                 430 aaa ata gat ctc tgg tcg tac aac gcg gag ctt ctt gtt gcc ctg gag      1344
Lys Ile Asp Leu Trp Ser Tyr Asn Ala Glu Leu Leu Val Ala Leu Glu
        435                 440                 445 aac caa cat aca att gat cta act gac tca gaa atg aac aaa ctg ttt      1392
Asn Gln His Thr Ile Asp Leu Thr Asp Ser Glu Met Asn Lys Leu Phe
    450                 455                 460 gaa aga aca aag aag caa ctg agg gaa aat gct gag gat atg ggc aat      1440
Glu Arg Thr Lys Lys Gln Leu Arg Glu Asn Ala Glu Asp Met Gly Asn
465                 470                 475                 480 ggt tgt ttc aaa ata tac cac aaa tgt gac aat gcc tgc ata ggg tca      1488
Gly Cys Phe Lys Ile Tyr His Lys Cys Asp Asn Ala Cys Ile Gly Ser
                485                 490                 495 atc aga aat gga act tat gac cat gat gta tac aga gac gaa gca tta      1536
Ile Arg Asn Gly Thr Tyr Asp His Asp Val Tyr Arg Asp Glu Ala Leu
            500                 505                 510 aac aac cgg ttc cag atc aaa ggt gtt gag ctg aag tca gga tac aaa      1584
Asn Asn Arg Phe Gln Ile Lys Gly Val Glu Leu Lys Ser Gly Tyr Lys
        515                 520                 525 gat tgg atc cta tgg att tcc ttt gcc ata tca tgc ttt ttg ctt tgt      1632
Asp Trp Ile Leu Trp Ile Ser Phe Ala Ile Ser Cys Phe Leu Leu Cys
    530                 535                 540 gtt gtt ttg ctg ggg ttc atc atg tgg gcc tgc caa aaa ggc aac att      1680
Val Val Leu Leu Gly Phe Ile Met Trp Ala Cys Gln Lys Gly Asn Ile
545                 550                 555                 560 agg tgc aac att tgc att tga                                           1701
Arg Cys Asn Ile Cys Ile
                565

<210> SEQ ID NO 2
<211> LENGTH: 566
<212> TYPE: PRT
<213> ORGANISM: Influenza A virus

<400> SEQUENCE: 2

Met Lys Thr Ile Ile Ala Leu Ser Tyr Ile Leu Cys Leu Val Phe Ala
1               5                   10                  15

Gln Lys Leu Pro Gly Asn Asp Asn Ser Thr Ala Thr Leu Cys Leu Gly
            20                  25                  30

His His Ala Val Ser Asn Gly Thr Leu Val Lys Thr Ile Thr Asn Asp
        35                  40                  45

Gln Ile Glu Val Thr Asn Ala Thr Glu Leu Val Gln Ser Ser Ser Thr
    50                  55                  60

Gly Arg Ile Cys Asp Ser Pro His Gln Ile Leu Asp Gly Glu Asn Cys
65                  70                  75                  80

Thr Leu Ile Asp Ala Leu Leu Gly Asp Pro His Cys Asp Gly Phe Gln
                85                  90                  95

Asn Lys Glu Trp Asp Leu Phe Val Glu Arg Ser Lys Ala Tyr Ser Asn
            100                 105                 110

Cys Tyr Pro Tyr Asp Val Pro Asp Tyr Ala Ser Leu Arg Ser Leu Val
        115                 120                 125

Ala Ser Ser Gly Thr Leu Glu Phe Asn Asn Glu Ser Phe Asn Trp Thr
    130                 135                 140

Gly Val Ala Gln Asn Gly Thr Ser Ser Ala Cys Lys Arg Arg Ser Asn
```

```
            145                 150                 155                 160
Lys Ser Phe Phe Ser Arg Leu Asn Trp Leu His Gln Leu Lys Tyr Lys
                    165                 170                 175
Tyr Pro Ala Leu Asn Val Thr Met Pro Asn Glu Lys Phe Asp Lys
                180                 185                 190
Leu Tyr Ile Trp Gly Val His His Pro Ser Thr Asp Ser Asp Gln Ile
            195                 200                 205
Ser Ile Tyr Ala Gln Ala Ser Gly Arg Val Thr Val Ser Thr Lys Arg
210                 215                 220
Ser Gln Gln Thr Val Ile Pro Asn Ile Gly Ser Ser Pro Trp Val Arg
225                 230                 235                 240
Gly Val Ser Ser Arg Ile Ser Ile Tyr Trp Thr Ile Val Lys Pro Gly
                    245                 250                 255
Asp Ile Leu Leu Ile Asn Ser Thr Gly Asn Leu Ile Ala Pro Arg Gly
                260                 265                 270
Tyr Phe Lys Ile Arg Ser Gly Lys Ser Ser Ile Met Arg Ser Asp Ala
            275                 280                 285
Pro Ile Gly Lys Cys Asn Ser Glu Cys Ile Thr Pro Asn Gly Ser Ile
        290                 295                 300
Pro Asn Asp Lys Pro Phe Gln Asn Val Asn Arg Ile Thr Tyr Gly Ala
305                 310                 315                 320
Cys Pro Arg Tyr Val Lys Gln Asn Thr Leu Lys Leu Ala Thr Gly Met
                    325                 330                 335
Arg Asn Val Pro Glu Lys Gln Thr Arg Gly Ile Phe Gly Ala Ile Ala
                340                 345                 350
Gly Phe Ile Glu Asn Gly Trp Glu Gly Met Val Asp Gly Trp Tyr Gly
            355                 360                 365
Phe Arg His Gln Asn Ser Glu Gly Thr Gly Gln Ala Ala Asp Leu Lys
        370                 375                 380
Ser Thr Gln Ala Ala Ile Asn Gln Ile Asn Gly Lys Leu Asn Arg Leu
385                 390                 395                 400
Ile Glu Lys Thr Asn Glu Lys Phe His Gln Ile Glu Lys Glu Phe Ser
                    405                 410                 415
Glu Val Glu Gly Arg Ile Gln Asp Leu Glu Lys Tyr Val Glu Asp Thr
                420                 425                 430
Lys Ile Asp Leu Trp Ser Tyr Asn Ala Glu Leu Leu Val Ala Leu Glu
            435                 440                 445
Asn Gln His Thr Ile Asp Leu Thr Asp Ser Glu Met Asn Lys Leu Phe
        450                 455                 460
Glu Arg Thr Lys Lys Gln Leu Arg Glu Asn Ala Glu Asp Met Gly Asn
465                 470                 475                 480
Gly Cys Phe Lys Ile Tyr His Lys Cys Asp Asn Ala Cys Ile Gly Ser
                    485                 490                 495
Ile Arg Asn Gly Thr Tyr Asp His Asp Val Tyr Arg Asp Glu Ala Leu
                500                 505                 510
Asn Asn Arg Phe Gln Ile Lys Gly Val Glu Leu Lys Ser Gly Tyr Lys
            515                 520                 525
Asp Trp Ile Leu Trp Ile Ser Phe Ala Ile Ser Cys Phe Leu Leu Cys
        530                 535                 540
Val Val Leu Leu Gly Phe Ile Met Trp Ala Cys Gln Lys Gly Asn Ile
545                 550                 555                 560
Arg Cys Asn Ile Cys Ile
                565
```

<210> SEQ ID NO 3
<211> LENGTH: 1647
<212> TYPE: DNA
<213> ORGANISM: Influenza A virus
<220> FEATURE:
<221> NAME/KEY: CDS
<222> LOCATION: (1)..(1647)
<220> FEATURE:
<221> NAME/KEY: misc_feature
<222> LOCATION: (1)..(1647)
<223> OTHER INFORMATION: Nucleotide sequence of HA of Influenza virus
    A/Turkey/Wisconsin/68
    Gene Bank: U79456.1

<400> SEQUENCE: 3

| gac | caa | atc | tgc | atc | ggt | tat | cat | gca | aac | aat | tca | aca | aaa | caa | gtt | 48 |
| Asp | Gln | Ile | Cys | Ile | Gly | Tyr | His | Ala | Asn | Asn | Ser | Thr | Lys | Gln | Val | |
| 1 | | | | 5 | | | | | 10 | | | | | 15 | | |

| gac | aca | atc | atg | gag | aag | aat | gtg | acg | gtc | aca | cat | gct | caa | gat | ata | 96 |
| Asp | Thr | Ile | Met | Glu | Lys | Asn | Val | Thr | Val | Thr | His | Ala | Gln | Asp | Ile | |
| | | | 20 | | | | | 25 | | | | | 30 | | | |

| ctg | gaa | aaa | gag | cac | aac | ggg | aaa | ctc | tgc | agt | ctc | aaa | gga | gtg | agg | 144 |
| Leu | Glu | Lys | Glu | His | Asn | Gly | Lys | Leu | Cys | Ser | Leu | Lys | Gly | Val | Arg | |
| | 35 | | | | | 40 | | | | | 45 | | | | | |

| ccc | ctc | att | ctg | aag | gat | tgc | agt | gtg | gct | gga | tgg | ctt | ctt | ggg | aac | 192 |
| Pro | Leu | Ile | Leu | Lys | Asp | Cys | Ser | Val | Ala | Gly | Trp | Leu | Leu | Gly | Asn | |
| 50 | | | | | 55 | | | | | 60 | | | | | | |

| cca | atg | tgt | gat | gag | ttc | cta | aat | gta | ccg | gaa | tgg | tca | tat | att | gta | 240 |
| Pro | Met | Cys | Asp | Glu | Phe | Leu | Asn | Val | Pro | Glu | Trp | Ser | Tyr | Ile | Val | |
| 65 | | | | | 70 | | | | | 75 | | | | | 80 | |

| gag | aag | gac | aat | cca | acc | aat | ggc | tta | tgt | tat | ccg | gga | gac | ttc | aat | 288 |
| Glu | Lys | Asp | Asn | Pro | Thr | Asn | Gly | Leu | Cys | Tyr | Pro | Gly | Asp | Phe | Asn | |
| | | | | 85 | | | | | 90 | | | | | 95 | | |

| gat | tat | gaa | gaa | ctg | aag | tat | tta | atg | agc | aac | aca | aac | cat | ttt | gag | 336 |
| Asp | Tyr | Glu | Glu | Leu | Lys | Tyr | Leu | Met | Ser | Asn | Thr | Asn | His | Phe | Glu | |
| | | | 100 | | | | | 105 | | | | | 110 | | | |

| aaa | att | caa | ata | atc | cct | agg | aac | tct | tgg | tcc | aat | cat | gat | gcc | tca | 384 |
| Lys | Ile | Gln | Ile | Ile | Pro | Arg | Asn | Ser | Trp | Ser | Asn | His | Asp | Ala | Ser | |
| | | 115 | | | | | 120 | | | | | 125 | | | | |

| tca | gga | gtg | agc | tca | gca | tgc | cca | tac | aat | ggt | agg | tct | tcc | ttt | ttc | 432 |
| Ser | Gly | Val | Ser | Ser | Ala | Cys | Pro | Tyr | Asn | Gly | Arg | Ser | Ser | Phe | Phe | |
| | 130 | | | | | 135 | | | | | 140 | | | | | |

| agg | agt | gtg | gtg | tgg | ttg | atc | aag | aag | agt | aat | gta | tac | cca | aca | ata | 480 |
| Arg | Ser | Val | Val | Trp | Leu | Ile | Lys | Lys | Ser | Asn | Val | Tyr | Pro | Thr | Ile | |
| 145 | | | | | 150 | | | | | 155 | | | | | 160 | |

| aag | agg | acc | tac | aat | aac | acc | aat | gta | gag | gac | ctt | ctg | ata | ttg | tgg | 528 |
| Lys | Arg | Thr | Tyr | Asn | Asn | Thr | Asn | Val | Glu | Asp | Leu | Leu | Ile | Leu | Trp | |
| | | | | 165 | | | | | 170 | | | | | 175 | | |

| gga | atc | cat | cac | cct | aat | gat | gca | gcg | gaa | caa | acg | aaa | ctc | tat | cag | 576 |
| Gly | Ile | His | His | Pro | Asn | Asp | Ala | Ala | Glu | Gln | Thr | Lys | Leu | Tyr | Gln | |
| | | | 180 | | | | | 185 | | | | | 190 | | | |

| aac | tcg | aac | act | tat | gtg | tct | gta | gga | aca | tca | aca | cta | aat | cag | agg | 624 |
| Asn | Ser | Asn | Thr | Tyr | Val | Ser | Val | Gly | Thr | Ser | Thr | Leu | Asn | Gln | Arg | |
| | | 195 | | | | | 200 | | | | | 205 | | | | |

| tca | att | cca | gaa | ata | gct | acc | agg | ccc | aaa | gtg | aat | gga | caa | agt | gga | 672 |
| Ser | Ile | Pro | Glu | Ile | Ala | Thr | Arg | Pro | Lys | Val | Asn | Gly | Gln | Ser | Gly | |
| | 210 | | | | | 215 | | | | | 220 | | | | | |

| aga | ata | gaa | ttt | ttc | tgg | aca | ata | cta | agg | ccg | aac | gat | gca | atc | agc | 720 |
| Arg | Ile | Glu | Phe | Phe | Trp | Thr | Ile | Leu | Arg | Pro | Asn | Asp | Ala | Ile | Ser | |
| 225 | | | | | 230 | | | | | 235 | | | | | 240 | |

| ttt | gaa | agt | aat | ggg | aac | ttt | ata | gct | cct | gaa | tat | gca | tac | aag | ata | 768 |

|   |   |   |   |   |   |   |   |   |   |   |   |   |
|---|---|---|---|---|---|---|---|---|---|---|---|---|
| Phe | Glu | Ser | Asn | Gly | Asn | Phe | Ile | Ala | Pro | Glu | Tyr | Ala | Tyr | Lys | Ile |
|   |   |   |   | 245 |   |   |   | 250 |   |   |   | 255 |

```
gtt aaa aag gga gat tca gca atc atg aga agc gaa ctg gag tat ggc       816
Val Lys Lys Gly Asp Ser Ala Ile Met Arg Ser Glu Leu Glu Tyr Gly
            260                 265                 270 aac tgt gat acc aaa tgt cag acc cca gtg ggt gct ata aat tcc agt       864
Asn Cys Asp Thr Lys Cys Gln Thr Pro Val Gly Ala Ile Asn Ser Ser
        275                 280                 285 atg cct ttt cac aat gtt cat ccc ctt acc att gga gag tgt ccc aaa       912
Met Pro Phe His Asn Val His Pro Leu Thr Ile Gly Glu Cys Pro Lys
    290                 295                 300 tat gtc aaa tca gat aaa ctg gtc ctt gca aca gga ctg agg aac gtg       960
Tyr Val Lys Ser Asp Lys Leu Val Leu Ala Thr Gly Leu Arg Asn Val
305                 310                 315                 320 cct cag aga gaa aca aga ggt ctg ttt gga gca ata gca gga ttc ata      1008
Pro Gln Arg Glu Thr Arg Gly Leu Phe Gly Ala Ile Ala Gly Phe Ile
                325                 330                 335 gaa ggg ggg tgg caa gga atg gta gat gga tgg tat ggt tac cat cat      1056
Glu Gly Gly Trp Gln Gly Met Val Asp Gly Trp Tyr Gly Tyr His His
            340                 345                 350 agc aac gag cag gga agt gga tat gct gca gac aaa gag tcc act cag      1104
Ser Asn Glu Gln Gly Ser Gly Tyr Ala Ala Asp Lys Glu Ser Thr Gln
        355                 360                 365 aaa gca atc gac ggg atc acc aat aaa gtc aac tca atc att gac aaa      1152
Lys Ala Ile Asp Gly Ile Thr Asn Lys Val Asn Ser Ile Ile Asp Lys
    370                 375                 380 atg aac act caa ttc gaa gcc gtt ggg aaa gaa ttc aac aac tta gaa      1200
Met Asn Thr Gln Phe Glu Ala Val Gly Lys Glu Phe Asn Asn Leu Glu
385                 390                 395                 400 agg aga ata gaa aat ttg aat aag aaa atg gaa gat gga ttt cta gat      1248
Arg Arg Ile Glu Asn Leu Asn Lys Lys Met Glu Asp Gly Phe Leu Asp
                405                 410                 415 gta tgg act tac aat gca gaa ctt ctg gtg ctc atg gaa aat gaa aga      1296
Val Trp Thr Tyr Asn Ala Glu Leu Leu Val Leu Met Glu Asn Glu Arg
            420                 425                 430 act ctg gat ttc cat gat tca tat gtc aag aac cta tac gat aag gtc      1344
Thr Leu Asp Phe His Asp Ser Tyr Val Lys Asn Leu Tyr Asp Lys Val
        435                 440                 445 cga ctc cag ctg aga gat aat gca aaa gaa ttg ggc aat ggg tgt ttg      1392
Arg Leu Gln Leu Arg Asp Asn Ala Lys Glu Leu Gly Asn Gly Cys Leu
    450                 455                 460 gag ttc tcc cac aaa tgt gac aat gaa tgc atg gaa agt gtg aga aac      1440
Glu Phe Ser His Lys Cys Asp Asn Glu Cys Met Glu Ser Val Arg Asn
465                 470                 475                 480 gga acg tat gac tat cca caa tac tca gaa gaa tca agg ctg aac aga      1488
Gly Thr Tyr Asp Tyr Pro Gln Tyr Ser Glu Glu Ser Arg Leu Asn Arg
                485                 490                 495 gag gaa ata gat gga gtc aaa ttg gag tca atg ggc acc tat cag ata      1536
Glu Glu Ile Asp Gly Val Lys Leu Glu Ser Met Gly Thr Tyr Gln Ile
            500                 505                 510 cta tca att tac tca aca gtg gcg agt tcc cta gca ctg gca atc atg      1584
Leu Ser Ile Tyr Ser Thr Val Ala Ser Ser Leu Ala Leu Ala Ile Met
        515                 520                 525 gta gct ggt ctg tct ttt tgg atg tgc tcc aat gga tca ttg caa tgc      1632
Val Ala Gly Leu Ser Phe Trp Met Cys Ser Asn Gly Ser Leu Gln Cys
    530                 535                 540 aga att tgc atc tag                                                  1647
Arg Ile Cys Ile
545
```

<210> SEQ ID NO 4
<211> LENGTH: 548
<212> TYPE: PRT
<213> ORGANISM: Influenza A virus

<400> SEQUENCE: 4

Asp Gln Ile Cys Ile Gly Tyr His Ala Asn Asn Ser Thr Lys Gln Val
1               5                   10                  15

Asp Thr Ile Met Glu Lys Asn Val Thr Val Thr His Ala Gln Asp Ile
            20                  25                  30

Leu Glu Lys Glu His Asn Gly Lys Leu Cys Ser Leu Lys Gly Val Arg
        35                  40                  45

Pro Leu Ile Leu Lys Asp Cys Ser Val Ala Gly Trp Leu Leu Gly Asn
    50                  55                  60

Pro Met Cys Asp Glu Phe Leu Asn Val Pro Glu Trp Ser Tyr Ile Val
65                  70                  75                  80

Glu Lys Asp Asn Pro Thr Asn Gly Leu Cys Tyr Pro Gly Asp Phe Asn
                85                  90                  95

Asp Tyr Glu Glu Leu Lys Tyr Leu Met Ser Asn Thr Asn His Phe Glu
            100                 105                 110

Lys Ile Gln Ile Ile Pro Arg Asn Ser Trp Ser Asn His Asp Ala Ser
        115                 120                 125

Ser Gly Val Ser Ser Ala Cys Pro Tyr Asn Gly Arg Ser Ser Phe Phe
    130                 135                 140

Arg Ser Val Val Trp Leu Ile Lys Lys Ser Asn Val Tyr Pro Thr Ile
145                 150                 155                 160

Lys Arg Thr Tyr Asn Asn Thr Asn Val Glu Asp Leu Leu Ile Leu Trp
                165                 170                 175

Gly Ile His His Pro Asn Asp Ala Ala Glu Gln Thr Glu Leu Tyr Gln
            180                 185                 190

Asn Ser Asn Thr Tyr Val Ser Val Gly Thr Ser Thr Leu Asn Gln Arg
        195                 200                 205

Ser Ile Pro Glu Ile Ala Thr Arg Pro Lys Val Asn Gly Gln Ser Gly
    210                 215                 220

Arg Ile Glu Phe Phe Trp Thr Ile Leu Arg Pro Asn Asp Ala Ile Ser
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Arg Ser Glu Leu Glu Tyr Gly
            260                 265                 270

Asn Cys Asp Thr Lys Cys Gln Thr Pro Val Gly Ala Ile Asn Ser Ser
        275                 280                 285

Met Pro Phe His Asn Val His Pro Leu Thr Ile Gly Glu Cys Pro Lys
    290                 295                 300

Tyr Val Lys Ser Asp Lys Leu Val Leu Ala Thr Gly Leu Arg Asn Val
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Ile Thr Asn Lys Val Asn Ser Ile Ile Asp Lys
    370                 375                 380

```
Met Asn Thr Gln Phe Glu Ala Val Gly Lys Glu Phe Asn Asn Leu Glu
385                 390                 395                 400

Arg Arg Ile Glu Asn Leu Asn Lys Lys Met Glu Asp Gly Phe Leu Asp
            405                 410                 415

Val Trp Thr Tyr Asn Ala Glu Leu Leu Val Leu Met Glu Asn Glu Arg
        420                 425                 430

Thr Leu Asp Phe His Asp Ser Tyr Val Lys Asn Leu Tyr Asp Lys Val
    435                 440                 445

Arg Leu Gln Leu Arg Asp Asn Ala Lys Glu Leu Gly Asn Gly Cys Leu
450                 455                 460

Glu Phe Ser His Lys Cys Asp Asn Glu Cys Met Glu Ser Val Arg Asn
465                 470                 475                 480

Gly Thr Tyr Asp Tyr Pro Gln Tyr Ser Glu Glu Ser Arg Leu Asn Arg
            485                 490                 495

Glu Glu Ile Asp Gly Val Lys Leu Glu Ser Met Gly Thr Tyr Gln Ile
        500                 505                 510

Leu Ser Ile Tyr Ser Thr Val Ala Ser Ser Leu Ala Leu Ala Ile Met
    515                 520                 525

Val Ala Gly Leu Ser Phe Trp Met Cys Ser Asn Gly Ser Leu Gln Cys
530                 535                 540

Arg Ile Cys Ile
545

<210> SEQ ID NO 5
<211> LENGTH: 1659
<212> TYPE: DNA
<213> ORGANISM: Influenza A virus
<220> FEATURE:
<221> NAME/KEY: CDS
<222> LOCATION: (1)..(1659)
<220> FEATURE:
<221> NAME/KEY: misc_feature
<222> LOCATION: (1)..(1659)
<223> OTHER INFORMATION: Influenza A virus (A/chicken/Queretaro/7653-
      20/95(H5N2)) Genbank Accession No. U79448

<400> SEQUENCE: 5 gac caa atc tgc att ggt tat cat gca aac aat tca aca aaa cag gtt      48
Asp Gln Ile Cys Ile Gly Tyr His Ala Asn Asn Ser Thr Lys Gln Val
1               5                   10                  15 gac aca atc atg gag aag aat gtg acg gtc aca cat gct cag gac ata      96
Asp Thr Ile Met Glu Lys Asn Val Thr Val Thr His Ala Gln Asp Ile
            20                  25                  30 ctg gaa aaa gaa cac aat gga aga ctc tgc agt ctt aaa gga gtg aag     144
Leu Glu Lys Glu His Asn Gly Arg Leu Cys Ser Leu Lys Gly Val Lys
        35                  40                  45 ccc ctc att ctg aag gat tgc agt gta gct gga tgg ctt ctt gga aat     192
Pro Leu Ile Leu Lys Asp Cys Ser Val Ala Gly Trp Leu Leu Gly Asn
    50                  55                  60 cca atg tgt gat gaa ttc ctg aat gta ccg gaa tgg tca tat att gtg     240
Pro Met Cys Asp Glu Phe Leu Asn Val Pro Glu Trp Ser Tyr Ile Val
65                  70                  75                  80 gaa aag gac aat cca gcc aat ggc ctg tgt tat ccg gga aac ttc aac     288
Glu Lys Asp Asn Pro Ala Asn Gly Leu Cys Tyr Pro Gly Asn Phe Asn
                85                  90                  95 gat tat gaa gaa ctg aag cat tta atg agc agc aca aac cat ttt gag     336
Asp Tyr Glu Glu Leu Lys His Leu Met Ser Ser Thr Asn His Phe Glu
            100                 105                 110 aaa att cag ata ttt cct agg agc tct tgg tcc aac cat gat gcc tca     384
```

```
                Lys Ile Gln Ile Phe Pro Arg Ser Ser Trp Ser Asn His Asp Ala Ser
                        115                 120                 125 tca gga gtg agc tct gca tgc cca tac aat ggt agg tct tcc ttt ttc          432
Ser Gly Val Ser Ser Ala Cys Pro Tyr Asn Gly Arg Ser Ser Phe Phe
130                 135                 140 agg aat gta gtg tgg ctg atc aag aag aat aat gtg tac cga aca ata          480
Arg Asn Val Val Trp Leu Ile Lys Lys Asn Asn Val Tyr Arg Thr Ile
145                 150                 155                 160 aag agg acc tac cat aac act aat gta gaa gac ctt tta ata tta tgg          528
Lys Arg Thr Tyr His Asn Thr Asn Val Glu Asp Leu Leu Ile Leu Trp
                165                 170                 175 gga att cat cac cct aat gat gca gct gaa cag ata aaa ctc tac cag          576
Gly Ile His His Pro Asn Asp Ala Ala Glu Gln Ile Lys Leu Tyr Gln
        180                 185                 190 aac ccg aac act tac gtg tca gtg gga aca tca aca ttg aat caa agg          624
Asn Pro Asn Thr Tyr Val Ser Val Gly Thr Ser Thr Leu Asn Gln Arg
            195                 200                 205 tca atc cca gaa ata gcc acc aga ccc aag gtg aac gga cag agt gga          672
Ser Ile Pro Glu Ile Ala Thr Arg Pro Lys Val Asn Gly Gln Ser Gly
210                 215                 220 agg atg gaa ttt ttt tgg aca ata cta agg ccg aac gac tca atc aac          720
Arg Met Glu Phe Phe Trp Thr Ile Leu Arg Pro Asn Asp Ser Ile Asn
225                 230                 235                 240 ttt gag agt act ggg aac ttt ata gct cct gaa tat gca tac aag ctt          768
Phe Glu Ser Thr Gly Asn Phe Ile Ala Pro Glu Tyr Ala Tyr Lys Leu
                245                 250                 255 att aaa aaa gga gat tca gca atc atg aaa agt gaa ctg aat tat ggt          816
Ile Lys Lys Gly Asp Ser Ala Ile Met Lys Ser Glu Leu Asn Tyr Gly
        260                 265                 270 aac tgt gat acc aaa tgt cag acc cca gcg ggt gct ata aat tcc agg          864
Asn Cys Asp Thr Lys Cys Gln Thr Pro Ala Gly Ala Ile Asn Ser Arg
            275                 280                 285 atg cct ttt cac aat gtc cat cct ttt act att ggg gag tgc ccc aag          912
Met Pro Phe His Asn Val His Pro Phe Thr Ile Gly Glu Cys Pro Lys
290                 295                 300 tat gtc aaa tcg aaa aaa cta gtt ctt gca aca ggg cta aga aac gta          960
Tyr Val Lys Ser Lys Lys Leu Val Leu Ala Thr Gly Leu Arg Asn Val
305                 310                 315                 320 ccc caa aga aaa aga aaa aga aaa aca aga ggc cta ttt gga gca ata         1008
Pro Gln Arg Lys Arg Lys Arg Lys Thr Arg Gly Leu Phe Gly Ala Ile
                325                 330                 335 gcc gga ttc ata gaa gga gga tgg caa gga atg gtg gat gga tgg tat         1056
Ala Gly Phe Ile Glu Gly Gly Trp Gln Gly Met Val Asp Gly Trp Tyr
        340                 345                 350 gga tat cat cat agc aat gag cag gga agt gga tat ggt gaa gac aac         1104
Gly Tyr His His Ser Asn Glu Gln Gly Ser Gly Tyr Gly Glu Asp Asn
            355                 360                 365 gaa tct aca cag aaa gca atc gat ggg atc act aat aaa gtc aac tca         1152
Glu Ser Thr Gln Lys Ala Ile Asp Gly Ile Thr Asn Lys Val Asn Ser
370                 375                 380 atc att gac aaa atg aac act caa ttc gaa gcc gtt ggg aaa gaa ttc         1200
Ile Ile Asp Lys Met Asn Thr Gln Phe Glu Ala Val Gly Lys Glu Phe
385                 390                 395                 400 aac aac cta gaa agg aga ata gaa aat ttg aat aag aaa atg gaa gat         1248
Asn Asn Leu Glu Arg Arg Ile Glu Asn Leu Asn Lys Lys Met Glu Asp
                405                 410                 415 ggc ttt ata gat gta tgg act tac aat gcg gaa ctt cta gtg ctc atg         1296
Gly Phe Ile Asp Val Trp Thr Tyr Asn Ala Glu Leu Leu Val Leu Met
        420                 425                 430
```

| | | |
|---|---|---|
| gaa aac gaa aga act ctg gat ctc cat gat tca aat gtc aag aaa tta<br>Glu Asn Glu Arg Thr Leu Asp Leu His Asp Ser Asn Val Lys Lys Leu<br>435 440 445 | | 1344 |
| tac gat agg gtc cga ctc cag ctg aga gac aat gcc aaa gaa tta ggc<br>Tyr Asp Arg Val Arg Leu Gln Leu Arg Asp Asn Ala Lys Glu Leu Gly<br>450 455 460 | | 1392 |
| aat ggg tgc ttt gaa ttc tac cac aag tgt gac aat gaa tgc atg gaa<br>Asn Gly Cys Phe Glu Phe Tyr His Lys Cys Asp Asn Glu Cys Met Glu<br>465 470 475 480 | | 1440 |
| agt gtg aga aat gga acg tat gac tat cca caa tac tca gaa gaa tca<br>Ser Val Arg Asn Gly Thr Tyr Asp Tyr Pro Gln Tyr Ser Glu Glu Ser<br>485 490 495 | | 1488 |
| aga ctg aac agg gag gaa ata gac gga gtc aaa tta gaa tca atg ggg<br>Arg Leu Asn Arg Glu Glu Ile Asp Gly Val Lys Leu Glu Ser Met Gly<br>500 505 510 | | 1536 |
| act tat cag ata ctt tca atc tat tca aca gta gcg agt tcc cta gca<br>Thr Tyr Gln Ile Leu Ser Ile Tyr Ser Thr Val Ala Ser Ser Leu Ala<br>515 520 525 | | 1584 |
| ctg gca atc atg gta gct ggt cta tct ttt tgg atg tgt tcc aat gga<br>Leu Ala Ile Met Val Ala Gly Leu Ser Phe Trp Met Cys Ser Asn Gly<br>530 535 540 | | 1632 |
| tca tta cag tgc aga att tgc atc tag<br>Ser Leu Gln Cys Arg Ile Cys Ile<br>545 550 | | 1659 |

<210> SEQ ID NO 6
<211> LENGTH: 552
<212> TYPE: PRT
<213> ORGANISM: Influenza A virus

<400> SEQUENCE: 6

Asp Gln Ile Cys Ile Gly Tyr His Ala Asn Asn Ser Thr Lys Gln Val
1               5                   10                  15

Asp Thr Ile Met Glu Lys Asn Val Thr Val Thr His Ala Gln Asp Ile
                20                  25                  30

Leu Glu Lys Glu His Asn Gly Arg Leu Cys Ser Leu Lys Gly Val Lys
            35                  40                  45

Pro Leu Ile Leu Lys Asp Cys Ser Val Ala Gly Trp Leu Leu Gly Asn
        50                  55                  60

Pro Met Cys Asp Glu Phe Leu Asn Val Pro Glu Trp Ser Tyr Ile Val
65                  70                  75                  80

Glu Lys Asp Asn Pro Ala Asn Gly Leu Cys Tyr Pro Gly Asn Phe Asn
                85                  90                  95

Asp Tyr Glu Glu Leu Lys His Leu Met Ser Ser Thr Asn His Phe Glu
            100                 105                 110

Lys Ile Gln Ile Phe Pro Arg Ser Ser Trp Ser Asn His Asp Ala Ser
        115                 120                 125

Ser Gly Val Ser Ser Ala Cys Pro Tyr Asn Gly Arg Ser Ser Phe Phe
    130                 135                 140

Arg Asn Val Val Trp Leu Ile Lys Lys Asn Asn Val Tyr Arg Thr Ile
145                 150                 155                 160

Lys Arg Thr Tyr His Asn Thr Asn Val Glu Asp Leu Leu Ile Leu Trp
                165                 170                 175

Gly Ile His His Pro Asn Asp Ala Ala Glu Gln Ile Lys Leu Tyr Gln
            180                 185                 190

Asn Pro Asn Thr Tyr Val Ser Val Gly Thr Ser Thr Leu Asn Gln Arg
        195                 200                 205

```
Ser Ile Pro Glu Ile Ala Thr Arg Pro Lys Val Asn Gly Gln Ser Gly
    210                 215                 220

Arg Met Glu Phe Phe Trp Thr Ile Leu Arg Pro Asn Asp Ser Ile Asn
225                 230                 235                 240

Phe Glu Ser Thr Gly Asn Phe Ile Ala Pro Glu Tyr Ala Tyr Lys Leu
                245                 250                 255

Ile Lys Lys Gly Asp Ser Ala Ile Met Lys Ser Glu Leu Asn Tyr Gly
            260                 265                 270

Asn Cys Asp Thr Lys Cys Gln Thr Pro Ala Gly Ala Ile Asn Ser Arg
        275                 280                 285

Met Pro Phe His Asn Val His Pro Phe Thr Ile Gly Glu Cys Pro Lys
290                 295                 300

Tyr Val Lys Ser Lys Lys Leu Val Leu Ala Thr Gly Leu Arg Asn Val
305                 310                 315                 320

Pro Gln Arg Lys Arg Lys Arg Lys Thr Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Gly Glu Asp Asn
        355                 360                 365

Glu Ser Thr Gln Lys Ala Ile Asp Gly Ile Thr Asn Lys Val Asn Ser
370                 375                 380

Ile Ile Asp Lys Met Asn Thr Gln Phe Glu Ala Val Gly Lys Glu Phe
385                 390                 395                 400

Asn Asn Leu Glu Arg Arg Ile Glu Asn Leu Asn Lys Lys Met Glu Asp
                405                 410                 415

Gly Phe Ile Asp Val Trp Thr Tyr Asn Ala Glu Leu Leu Val Leu Met
            420                 425                 430

Glu Asn Glu Arg Thr Leu Asp Leu His Asp Ser Asn Val Lys Lys Leu
        435                 440                 445

Tyr Asp Arg Val Arg Leu Gln Leu Arg Asp Asn Ala Lys Glu Leu Gly
450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ser
                485                 490                 495

Arg Leu Asn Arg Glu Glu Ile Asp Gly Val Lys Leu Glu Ser Met Gly
            500                 505                 510

Thr Tyr Gln Ile Leu Ser Ile Tyr Ser Thr Val Ala Ser Ser Leu Ala
        515                 520                 525

Leu Ala Ile Met Val Ala Gly Leu Ser Phe Trp Met Cys Ser Asn Gly
530                 535                 540

Ser Leu Gln Cys Arg Ile Cys Ile
545                 550

<210> SEQ ID NO 7
<211> LENGTH: 1647
<212> TYPE: DNA
<213> ORGANISM: Influenza A virus
<220> FEATURE:
<221> NAME/KEY: CDS
<222> LOCATION: (1)..(1647)
<220> FEATURE:
<221> NAME/KEY: misc_feature
<222> LOCATION: (1)..(1647)
<223> OTHER INFORMATION: Influenza A virus (A/turkey/Wisconsin/68(H5N9))
      Genbank Accession No. U79456
```

<400> SEQUENCE: 7

```
gac caa atc tgc atc ggt tat cat gca aac aat tca aca aaa caa gtt        48
Asp Gln Ile Cys Ile Gly Tyr His Ala Asn Asn Ser Thr Lys Gln Val
1               5                   10                  15 gac aca atc atg gag aag aat gtg acg gtc aca cat gct caa gat ata        96
Asp Thr Ile Met Glu Lys Asn Val Thr Val Thr His Ala Gln Asp Ile
            20                  25                  30 ctg gaa aaa gag cac aac ggg aaa ctc tgc agt ctc aaa gga gtg agg       144
Leu Glu Lys Glu His Asn Gly Lys Leu Cys Ser Leu Lys Gly Val Arg
        35                  40                  45 ccc ctc att ctg aag gat tgc agt gtg gct gga tgg ctt ctt ggg aac       192
Pro Leu Ile Leu Lys Asp Cys Ser Val Ala Gly Trp Leu Leu Gly Asn
    50                  55                  60 cca atg tgt gat gag ttc cta aat gta ccg gaa tgg tca tat att gta       240
Pro Met Cys Asp Glu Phe Leu Asn Val Pro Glu Trp Ser Tyr Ile Val
65                  70                  75                  80 gag aag gac aat cca acc aat ggc tta tgt tat ccg gga gac ttc aat       288
Glu Lys Asp Asn Pro Thr Asn Gly Leu Cys Tyr Pro Gly Asp Phe Asn
                85                  90                  95 gat tat gaa gaa ctg aag tat tta atg agc aac aca aac cat ttt gag       336
Asp Tyr Glu Glu Leu Lys Tyr Leu Met Ser Asn Thr Asn His Phe Glu
            100                 105                 110 aaa att caa ata atc cct agg aac tct tgg tcc aat cat gat gcc tca       384
Lys Ile Gln Ile Ile Pro Arg Asn Ser Trp Ser Asn His Asp Ala Ser
        115                 120                 125 tca gga gtg agc tca gca tgc cca tac aat ggt agg tct tcc ttt ttc       432
Ser Gly Val Ser Ser Ala Cys Pro Tyr Asn Gly Arg Ser Ser Phe Phe
    130                 135                 140 agg agt gtg gtg tgg ttg atc aag aag agt aat gta tac cca aca ata       480
Arg Ser Val Val Trp Leu Ile Lys Lys Ser Asn Val Tyr Pro Thr Ile
145                 150                 155                 160 aag agg acc tac aat aac acc aat gta gag gac ctt ctg ata ttg tgg       528
Lys Arg Thr Tyr Asn Asn Thr Asn Val Glu Asp Leu Leu Ile Leu Trp
                165                 170                 175 gga atc cat cac cct aat gat gca gcg gaa caa acg gaa ctc tat cag       576
Gly Ile His His Pro Asn Asp Ala Ala Glu Gln Thr Glu Leu Tyr Gln
            180                 185                 190 aac tcg aac act tat gtg tct gta gga aca tca aca cta aat cag agg       624
Asn Ser Asn Thr Tyr Val Ser Val Gly Thr Ser Thr Leu Asn Gln Arg
        195                 200                 205 tca att cca gaa ata gct acc agg ccc aaa gtg aat gga caa agt gga       672
Ser Ile Pro Glu Ile Ala Thr Arg Pro Lys Val Asn Gly Gln Ser Gly
    210                 215                 220 aga ata gaa ttt ttc tgg aca ata cta agg ccg aac gat gca atc agc       720
Arg Ile Glu Phe Phe Trp Thr Ile Leu Arg Pro Asn Asp Ala Ile Ser
225                 230                 235                 240 ttt gaa agt aat ggg aac ttt ata gct cct gaa tat gca tac aag ata       768
Phe Glu Ser Asn Gly Asn Phe Ile Ala Pro Glu Tyr Ala Tyr Lys Ile
                245                 250                 255 gtt aaa aag gga gat tca gca atc atg aga agc gaa ctg gag tat ggc       816
Val Lys Lys Gly Asp Ser Ala Ile Met Arg Ser Glu Leu Glu Tyr Gly
            260                 265                 270 aac tgt gat acc aaa tgt cag acc cca gtg ggt gct ata aat tcc agt       864
Asn Cys Asp Thr Lys Cys Gln Thr Pro Val Gly Ala Ile Asn Ser Ser
        275                 280                 285 atg cct ttt cac aat gtt cat ccc ctt acc att gga gag tgt ccc aaa       912
Met Pro Phe His Asn Val His Pro Leu Thr Ile Gly Glu Cys Pro Lys
    290                 295                 300
```

| | | | | | | | | | | | | | | | | |
|---|---|---|---|---|---|---|---|---|---|---|---|---|---|---|---|---|
| tat | gtc | aaa | tca | gat | aaa | ctg | gtc | ctt | gca | aca | gga | ctg | agg | aac | gtg | 960 |
| Tyr | Val | Lys | Ser | Asp | Lys | Leu | Val | Leu | Ala | Thr | Gly | Leu | Arg | Asn | Val | |
| 305 | | | | 310 | | | | 315 | | | | 320 | | | | |
| cct | cag | aga | gaa | aca | aga | ggt | ctg | ttt | gga | gca | ata | gca | gga | ttc | ata | 1008 |
| Pro | Gln | Arg | Glu | Thr | Arg | Gly | Leu | Phe | Gly | Ala | Ile | Ala | Gly | Phe | Ile | |
| | | | | 325 | | | | 330 | | | | 335 | | | | |
| gaa | ggg | ggg | tgg | caa | gga | atg | gta | gat | gga | tgg | tat | ggt | tac | cat | cat | 1056 |
| Glu | Gly | Gly | Trp | Gln | Gly | Met | Val | Asp | Gly | Trp | Tyr | Gly | Tyr | His | His | |
| | | | 340 | | | | 345 | | | | 350 | | | | | |
| agc | aac | gag | cag | gga | agt | gga | tat | gct | gca | gac | aaa | gag | tcc | act | cag | 1104 |
| Ser | Asn | Glu | Gln | Gly | Ser | Gly | Tyr | Ala | Ala | Asp | Lys | Glu | Ser | Thr | Gln | |
| | | 355 | | | | 360 | | | | 365 | | | | | | |
| aaa | gca | atc | gac | ggg | atc | acc | aat | aaa | gtc | aac | tca | atc | att | gac | aaa | 1152 |
| Lys | Ala | Ile | Asp | Gly | Ile | Thr | Asn | Lys | Val | Asn | Ser | Ile | Ile | Asp | Lys | |
| | 370 | | | | 375 | | | | 380 | | | | | | | |
| atg | aac | act | caa | ttc | gaa | gcc | gtt | ggg | aaa | gaa | ttc | aac | aac | tta | gaa | 1200 |
| Met | Asn | Thr | Gln | Phe | Glu | Ala | Val | Gly | Lys | Glu | Phe | Asn | Asn | Leu | Glu | |
| 385 | | | | 390 | | | | 395 | | | | 400 | | | | |
| agg | aga | ata | gaa | aat | ttg | aat | aag | aaa | atg | gaa | gat | gga | ttt | cta | gat | 1248 |
| Arg | Arg | Ile | Glu | Asn | Leu | Asn | Lys | Lys | Met | Glu | Asp | Gly | Phe | Leu | Asp | |
| | | | | 405 | | | | 410 | | | | 415 | | | | |
| gta | tgg | act | tac | aat | gca | gaa | ctt | ctg | gtg | ctc | atg | gaa | aat | gaa | aga | 1296 |
| Val | Trp | Thr | Tyr | Asn | Ala | Glu | Leu | Leu | Val | Leu | Met | Glu | Asn | Glu | Arg | |
| | | | 420 | | | | 425 | | | | 430 | | | | | |
| act | ctg | gat | ttc | cat | gat | tca | tat | gtc | aag | aac | cta | tac | gat | aag | gtc | 1344 |
| Thr | Leu | Asp | Phe | His | Asp | Ser | Tyr | Val | Lys | Asn | Leu | Tyr | Asp | Lys | Val | |
| | | 435 | | | | 440 | | | | 445 | | | | | | |
| cga | ctc | cag | ctg | aga | gat | aat | gca | aaa | gaa | ttg | ggc | aat | ggg | tgt | ttg | 1392 |
| Arg | Leu | Gln | Leu | Arg | Asp | Asn | Ala | Lys | Glu | Leu | Gly | Asn | Gly | Cys | Leu | |
| | 450 | | | | 455 | | | | 460 | | | | | | | |
| gag | ttc | tcc | cac | aaa | tgt | gac | aat | gaa | tgc | atg | gaa | agt | gtg | aga | aac | 1440 |
| Glu | Phe | Ser | His | Lys | Cys | Asp | Asn | Glu | Cys | Met | Glu | Ser | Val | Arg | Asn | |
| 465 | | | | 470 | | | | 475 | | | | 480 | | | | |
| gga | acg | tat | gac | tat | cca | caa | tac | tca | gaa | gaa | tca | agg | ctg | aac | aga | 1488 |
| Gly | Thr | Tyr | Asp | Tyr | Pro | Gln | Tyr | Ser | Glu | Glu | Ser | Arg | Leu | Asn | Arg | |
| | | | | 485 | | | | 490 | | | | 495 | | | | |
| gag | gaa | ata | gat | gga | gtc | aaa | ttg | gag | tca | atg | ggc | acc | tat | cag | ata | 1536 |
| Glu | Glu | Ile | Asp | Gly | Val | Lys | Leu | Glu | Ser | Met | Gly | Thr | Tyr | Gln | Ile | |
| | | | 500 | | | | 505 | | | | 510 | | | | | |
| cta | tca | att | tac | tca | aca | gtg | gcg | agt | tcc | cta | gca | ctg | gca | atc | atg | 1584 |
| Leu | Ser | Ile | Tyr | Ser | Thr | Val | Ala | Ser | Ser | Leu | Ala | Leu | Ala | Ile | Met | |
| | | 515 | | | | 520 | | | | 525 | | | | | | |
| gta | gct | ggt | ctg | tct | ttt | tgg | atg | tgc | tcc | aat | gga | tca | ttg | caa | tgc | 1632 |
| Val | Ala | Gly | Leu | Ser | Phe | Trp | Met | Cys | Ser | Asn | Gly | Ser | Leu | Gln | Cys | |
| | 530 | | | | 535 | | | | 540 | | | | | | | |
| aga | att | tgc | atc | tag | | | | | | | | | | | | 1647 |
| Arg | Ile | Cys | Ile | | | | | | | | | | | | | |
| 545 | | | | | | | | | | | | | | | | |

<210> SEQ ID NO 8
<211> LENGTH: 548
<212> TYPE: PRT
<213> ORGANISM: Influenza A virus

<400

```
                35                  40                  45
Pro Leu Ile Leu Lys Asp Cys Ser Val Ala Gly Trp Leu Leu Gly Asn
 50                  55                  60

Pro Met Cys Asp Glu Phe Leu Asn Val Pro Glu Trp Ser Tyr Ile Val
 65                  70                  75                  80

Glu Lys Asp Asn Pro Thr Asn Gly Leu Cys Tyr Pro Gly Asp Phe Asn
                     85                  90                  95

Asp Tyr Glu Glu Leu Lys Tyr Leu Met Ser Asn Thr Asn His Phe Glu
                100                 105                 110

Lys Ile Gln Ile Ile Pro Arg Asn Ser Trp Ser Asn His Asp Ala Ser
                115                 120                 125

Ser Gly Val Ser Ser Ala Cys Pro Tyr Asn Gly Arg Ser Ser Phe Phe
            130                 135                 140

Arg Ser Val Val Trp Leu Ile Lys Lys Ser Asn Val Tyr Pro Thr Ile
145                 150                 155                 160

Lys Arg Thr Tyr Asn Asn Thr Asn Val Glu Asp Leu Leu Ile Leu Trp
                165                 170                 175

Gly Ile His His Pro Asn Asp Ala Ala Glu Gln Thr Glu Leu Tyr Gln
                180                 185                 190

Asn Ser Asn Thr Tyr Val Ser Val Gly Thr Ser Thr Leu Asn Gln Arg
                195                 200                 205

Ser Ile Pro Glu Ile Ala Thr Arg Pro Lys Val Asn Gly Gln Ser Gly
            210                 215                 220

Arg Ile Glu Phe Phe Trp Thr Ile Leu Arg Pro Asn Asp Ala Ile Ser
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Arg Ser Glu Leu Glu Tyr Gly
                260                 265                 270

Asn Cys Asp Thr Lys Cys Gln Thr Pro Val Gly Ala Ile Asn Ser Ser
            275                 280                 285

Met Pro Phe His Asn Val His Pro Leu Thr Ile Gly Glu Cys Pro Lys
290                 295                 300

Tyr Val Lys Ser Asp Lys Leu Val Leu Ala Thr Gly Leu Arg Asn Val
305                 310                 315                 320

Pro Gln Arg Glu Thr Arg Gly Leu Phe Gly Ala Ile Ala Gly Phe Ile
                325                 330                 335

Glu Gly Gly Trp Gln Gly Met Val Asp Gly Trp Tyr Gly Tyr His His
                340                 345                 350

Ser Asn Glu Gln Gly Ser Gly Tyr Ala Ala Asp Lys Glu Ser Thr Gln
            355                 360                 365

Lys Ala Ile Asp Gly Ile Thr Asn Lys Val Asn Ser Ile Ile Asp Lys
            370                 375                 380

Met Asn Thr Gln Phe Glu Ala Val Gly Lys Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
                420                 425                 430

Thr Leu Asp Phe His Asp Ser Tyr Val Lys Asn Leu Tyr Asp Lys Val
            435                 440                 445

Arg Leu Gln Leu Arg Asp Asn Ala Lys Glu Leu Gly Asn Gly Cys Leu
450                 455                 460
```

```
Glu Phe Ser His Lys Cys Asp Asn Glu Cys Met Glu Ser Val Arg Asn
465                 470                 475                 480

Gly Thr Tyr Asp Tyr Pro Gln Tyr Ser Glu Glu Ser Arg Leu Asn Arg
                485                 490                 495

Glu Glu Ile Asp Gly Val Lys Leu Glu Ser Met Gly Thr Tyr Gln Ile
            500                 505                 510

Leu Ser Ile Tyr Ser Thr Val Ala Ser Ser Leu Ala Leu Ala Ile Met
            515                 520                 525

Val Ala Gly Leu Ser Phe Trp Met Cys Ser Asn Gly Ser Leu Gln Cys
        530                 535                 540

Arg Ile Cys Ile
545

<210> SEQ ID NO 9
<211> LENGTH: 39
<212> TYPE: DNA
<213> ORGANISM: Artificial Sequence
<220> FEATURE:
<223> OTHER INFORMATION: Primers Used in Construction of Ad vectors

<400> SEQUENCE: 9
cacacaggta ccgccatgaa gactatcatt gctttgagc                           39

<210> SEQ ID NO 10
<211> LENGTH: 32
<212> TYPE: DNA
<213> ORGANISM: Artificial Sequence
<220> FEATURE:
<223> OTHER INFORMATION: Primers Used in Construction of Ad vectors

<400> SEQUENCE: 10
cacacaggta cctcaaatgc aaatgttgca cc                                  32
```

IMMUNIZATION OF AVIANS BY ADMINISTRATION OF NON-REPLICATING VECTORED VACCINES

CROSS-REFERENCE TO RELATED APPLICATIONS

This application claims priority from U.S. provisional application Ser. No. 60/708,524, filed Aug. 15, 2005 which is incorporated by reference herein in its entirety.

Mention is also made of U.S. patent application Ser. No. 10/052,323, filed Jan. 18, 2002; Ser. No. 10/116,963, filed Apr. 5, 2002; Ser. No. 10/346,021, filed Jan. 16, 2003 and U.S. Pat. Nos. 6,706,693; 6,716,823; 6,348,450, and PCT/US98/16739, filed Aug. 13, 1998 which are incorporated by reference herein in their entirety.

Each of these applications, patents, and each document cited in this text, and each of the documents cited in each of these applications, patents, and documents ("application cited documents"), and each document referenced or cited in the application cited documents, either in the text or during the prosecution of the applications and patents thereof, as well as all arguments in support of patentability advanced during prosecution thereof, are hereby incorporated herein by reference.

FIELD OF THE INVENTION

The present invention relates generally to the fields of immunology and vaccine technology. More specifically, the invention relates to recombinant non-replicating vectors such as E1-defective human adenovirus vectors for delivery of avian immunogens and antigens, such as avian influenza virus antigens, into avians. The invention also provides methods of introducing and expressing an avian immunogen in avian subjects, including avian embryos, as well as methods of eliciting an immune response in avian subjects to immunogens.

BACKGROUND OF THE INVENTION

Avian influenza (AI) is a serious pathogen that infects avians, other animals, and humans. Since 1997, there have been several incidents of transmission of AI virus to humans (Subbarao et al., 1998; Ungchusak et al., 2005). Evidence also shows that genetic recombination between avian and human influenza viruses have occurred on multiple occasions in medical history (Kawaoka et al., 1989). Since avians and humans are in close contact, it is believed that the generation of new AI virus strains that could potentially cross the species barrier into the human population will continue to be a public health concern.

Mass vaccination of avians appears to be the most promising approach to prevent dissemination of AI virus and to reduce the risk of human pandemics. Vaccination of avians with inactivated whole virus vaccines has been performed in some countries over the past several years. These AI vaccines are prepared from amnio-allantoic fluid harvested from infected eggs, and are subsequently inactivated by formalin or β-propiolactone (Tollis and Di Trani, 2002). However, the unpredictable emergence of new AI virus strains, the evolution of AI virus into a form highly lethal to chicken embryos (Wood et al., 2002), and possible dissemination of lethal AI strains by bioterrorists make the rapid development and timely supply of safe and efficacious AI vaccine a crucial, yet very difficult, task. In addition, it is not possible to discriminate field-infected chickens from those previously vaccinated with inactivated AI viruses of the same strains (Normile, 2004).

An experimental recombinant fowlpox virus encoding the hemagglutinin (HA) of an AI virus has protected chickens against a H5N2 AI virus challenge after wing-web puncture, although the hemagglutination-inhibition (HI) serologic response was negligible (Beard et al., 1992). Chickens inoculated through the wing web with a live recombinant vaccinia virus expressing HA also developed protective immunity against a lethal AI virus challenge with low levels of serum HI antibody detected (Chambers et al., 1988). Although AI isolates of waterfowl-origin that have a tropism for the alimentary tract have been inoculated into chickens as an oral AI vaccine (Crawford et al., 1998), those isolates are not expected to be broadly effective against new AI virus strains, due to the inherently dynamic evolution of this type of virus.

Avians have also been immunized by subcutaneous injection of HA proteins expressed from baculovirus vectors (Crawford et al., 1999), and inoculation of an expression plasmid encoding HA into the skin using a gene gun (Fynan et al., 1993). These AI vaccines are able to protect avians from exhibiting clinical signs and death, and reduce respiratory and intestinal replication of a challenge virus containing homologous HA. There is also evidence that a low-cost aerosol AI vaccine expressing HA from a Newcastle disease virus vector (Swayne, 2003) or a recombinant influenza virus containing a non-pathogenic influenza virus backbone may be efficacious (Lee et al., 2004; Webby et al., 2004).

Most of the above AI vaccines rely upon labor-intensive parenteral delivery. The oral and aerosol AI vaccines suffer from inconsistencies in delivering a uniform dose to individual birds during mass-inoculation. The replicating vectors used in some vaccines also pose a biohazard by introducing unnatural microbial forms to the environment. The recombined influenza virus vaccine could even generate harmful reassortments through recombination between a reassortant influenza virus and a wild AI virus concurrently circulating in the environment (Hilleman, 2002).

There are several noteworthy reasons for utilizing recombinant Adenovirus ("Ad") vectors as a vaccine carrier. Ad vectors are able to transduce both mitotic and postmitotic cells in situ. Additionally, preparation of Ad stocks containing high titers of virus (i.e., greater than $10^{12}$ pfu [plaque-forming units] per ml) are easy to generate, which makes it possible to transduce cells in situ at high multiplicity of infection (MOI). Ad vectors also have a proven safety record, based on their long-term use as a vaccine. Further, the Ad virus is capable of inducing high levels of gene expression (at least as an initial burst), and replication-defective Ad vectors can be easily bioengineered, manufactured, and stored using techniques well known in the art.

Ad-based vaccines are more potent than DNA vaccines due to Ad vector's high affinity for specific receptors and its ability to escape the endosomal pathway (Curiel, 1994). Ad vectors may transduce part of a chicken embryo through binding of its fiber to the coxsackie and adenovirus receptor (CAR) found on the surface of chicken cells (Tan et al., 2001). In addition, at least one of the Ad components, hexon, is highly immunogenic and can confer adjuvant activity to exogenous antigens (Molinier-Frenkel et al., 2002).

Ad-based vaccines mimic the effects of natural infections in their ability to induce major histocompatibility complex (MHC) class I restricted T-cell responses, yet eliminate the possibility of reversion back to virulence because only a subfragment of the pathogen's genome is expressed from the vector. This "selective expression" may solve the problem of differentiating vaccinated-but-uninfected animals from their infected counterparts, because the specific markers of the pathogen not encoded by the vector can be used to discriminate the two events. Notably, propagation of the pathogen is not required for generating vectored vaccines because the relevant antigen genes can be amplified and cloned directly from field samples (Rajakumar et al., 1990). This is particularly important for production of highly virulent AI strains, such as H5N1, because this strain is too dangerous and difficult to propagate (Wood et al., 2002). In addition to the above criteria, commercial concerns factor heavily in the poultry industry. The current AI vaccine alone costs about 7 cents per bird, not counting the labor of injecting running birds (Normile, 2004).

Replication-incompetent E1/E3-defective human Ad serotype 5 (Ad5)-derived vectors have been extensively studied in mammals (Graham and Prevec, 1995). Although chickens have been immunized by subcutaneous or intradermal injection of an avian Ad chicken embryo lethal orphan (CELO) viral vector encoding an antigen (Francois et al., 2004), the CELO vector has a low compliance rate and could be potentially harmful due to its ability to replicate in chicken cells. Since CELO possesses no identifiable E1, E3, and E4 regions (Chiocca et al., 1996), a replication-incompetent CELO vector is not available as a carrier for immunization at this time. The present invention addresses this need by providing a safe and efficient method for gene delivery to protect avians in a wide variety of disease settings, and consequently prevent transmission of avian pathogens to humans.

SUMMARY OF THE INVENTION

It has now been surprisingly shown that intramuscular and in ovo delivery of human adenovirus-vectored vaccines can rapidly, safely, and effectively immunize avians. Mass immunization of avians against several avian pathogens is crucial to prevent enormous economic loss, and to impede transmission of avian pathogens, such as avian influenza virus, to the human population. In ovo delivery of vaccines or immunogenic compositions with a mechanized injector is a non-labor-intensive method for mass immunization of avians in a timely manner. Unlike other in ovo avian vaccines, production of human adenovirus-vectored vaccines or immunogenic compositions does not require the propagation of lethal pathogens and does not involve transmission of antigens or immunogens by a vector that is capable of replication in avians. Furthermore, immunization by this type of vaccine or immunogenic composition allows differentiation between vaccinated and naturally infected animals.

In one aspect, the present invention provides a recombinant human adenovirus expression vector that comprises and expresses an adenoviral DNA sequence, and a promoter sequence operably linked to a foreign sequence encoding one or more avian antigens or immunogens of interest.

Preferably, the human adenoviral sequences are derived from human adenovirus serotype 5. The human adenoviral sequences can be derived from replication-defective adenovirus, non-replicating adenovirus, replication-competent adenovirus, or wild-type adenovirus.

The promoter sequence can be selected from the group consisting of viral promoters, avian promoters, CMV promoter, SV40 promoter, β-actin promoter, albumin promoter, EF1-α promoter, PγK promoter, MFG promoter, and Rous sarcoma virus promoter.

The one or more avian antigens or immunogens of interest can be derived from for example, avian influenza virus, infectious bursal disease virus, Marek's disease virus, Herpesviruses such as infectious laryngotracheitis virus, avian infectious bronchitis virus, avian reovirus, poxviruses including avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

Preferably, the one or more avian antigens or immunogens of interest are derived from avian influenza, i.e., hemagglutinin, nucleoprotein, matrix, and neuraminidase.

More preferably, the one or more avian antigens or immunogens of interest are derived from hemagglutinin subtype 3, 5, 7, or 9.

Another aspect of the invention provides an immunogenic composition or vaccine for in vivo delivery into an avian subject comprising a veterinarily acceptable vehicle or excipient and a recombinant human adenovirus expression vector that comprises and expresses an adenoviral DNA sequence, and a promoter sequence operably linked to a foreign sequence encoding one or more avian antigens or immunogens of interest.

Preferably, the adenoviral DNA sequence is derived from adenovirus serotype 5 (Ad5).

Preferably, the human adenoviral sequences are derived from human adenovirus serotype 5. The human adenoviral sequences can be derived from replication-defective adenovirus.

The promoter sequence can be selected from the group consisting of viral promoters, avian promoters, CMV promoter, SV40 promoter, β-actin promoter, albumin promoter, EF1-α promoter, PγK promoter, MFG promoter, and Rous sarcoma virus promoter.

The one or more avian antigens or immunogens of interest can be derived from for example, avian influenza virus, infectious bursal disease virus, Marek's disease virus, Herpesviruses such as infectious laryngotracheitis virus, avian infectious bronchitis virus, avian reovirus, poxviruses including avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

Preferably, the one or more avian antigens or immunogens of interest are derived from avian influenza, i.e., hemagglutinin, nucleoprotein, matrix, and neuraminidase.

More preferably, the one or more avian antigens or immunogens of interest are derived from hemagglutinin subtype 3, 5, 7, or 9.

The immunogenic composition or vaccine may further comprise an adjuvant.

The immunogenic composition or vaccine may further comprise an additional vaccine.

Another aspect of the invention provides a method of introducing and expressing one or more avian antigens or immunogens in a cell, comprising contacting the cell with a recombinant human adenovirus expression vector that comprises and expresses an adenoviral DNA sequence, and a promoter sequence operably linked to a foreign sequence encoding one or more avian antigens or immunogens of interest, and culturing the cell under conditions sufficient to express the one or more avian antigens or immunogens in the cell.

Preferably, the cell is a 293 cell or a PER.C6 cell.

Preferably, the one or more avian antigens or immunogens of interest are derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

Preferably, the foreign sequence encoding the one or more avian antigens or immunogens of interest is derived from one or more avian viruses.

Preferably, the foreign sequence encoding the one or more avian antigens or immunogens of interest is derived from avian influenza.

More preferably, the foreign sequence encoding the one or more avian antigens or immunogens of interest is selected from the group consisting of hemagglutinin, nucleoprotein, matrix, or neuraminidase.

More preferably, the foreign sequence encoding the one or more avian antigens or immunogens of interest is selected from the group consisting of hemagglutinin subtype 3, 5, 7, or 9.

Another aspect of the invention provides a method of introducing and expressing one or more avian influenza antigens or immunogens in an avian embryo, comprising contacting the avian embryo with a recombinant human adenovirus expression vector that comprises and expresses an adenoviral DNA sequence, and a promoter sequence operably linked to a foreign sequence encoding one or more avian antigens or immunogens of interest, thereby obtaining expression of the one or more avian influenza antigens or immunogens in the avian embryo.

Preferably, the foreign sequence encoding the one or more avian antigens or immunogens of interest is derived from one or more avian viruses.

More preferably, the foreign sequence encoding the one or more avian antigens or immunogens of interest is derived from avian influenza.

More preferably, the foreign sequence encoding the one or more avian antigens or immunogens of interest is selected from the group consisting of hemagglutinin, nucleoprotein, matrix, or neuraminidase.

More preferably, the foreign sequence encoding the one or more avian antigens or immunogens of interest is selected from the group consisting of hemagglutinin subtype 3, 5, 7, or 9.

The method of introducing and expressing one or more avian influenza antigens or immunogens in an avian embryo preferably can occur by by in ovo delivery.

Another aspect of the present invention provides a method of eliciting an immunogenic response in an avian subject, comprising administering an immunologically effective amount of the composition of the invention to the avian subject.

Yet another aspect of the present invention provides a method of eliciting an immunogenic response in an avian subject, comprising infecting the avian subject with an immunologically effective amount of an immunogenic composition comprising a recombinant human adenovirus expression vector that comprises and expresses an adenoviral DNA sequence, and a promoter sequence operably linked to a foreign sequence encoding one or more avian antigens or immunogens of interest, wherein the one or more avian antigens or immunogens of interest are expressed at a level sufficient to elicit an immunogenic response to the one or more avian antigens or immunogens of interest in the avian subject.

Preferably, the one or more avian antigens or immunogens of interest are derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

More preferably, the foreign sequence encoding the one or more avian antigens or immunogens of interest is derived from avian influenza.

More preferably, the foreign sequence encoding the one or more avian antigens or immunogens of interest is selected from the group consisting of hemagglutinin, nucleoprotein, matrix, or neuraminidase.

More preferably, the foreign sequence encoding the one or more avian antigens or immunogens of interest is selected from the group consisting of hemagglutinin subtype 3, 5, 7, or 9.

The method may further comprise administering an additional vaccine.

Preferably, the method of infecting occurs by in ovo delivery.

Another aspect of the invention provides a method of eliciting an immunogenic response in an avian subject, comprising infecting the avian subject with an immunologically effective amount of an immunogenic composition comprising a recombinant human adenovirus expression vector that comprises and expresses an adenoviral DNA sequence, and a promoter sequence operably linked to a foreign sequence encoding one or more avian antigens or immunogens of interest, wherein the one or more avian antigens or immunogens of interest are expressed at a level sufficient to elicit an immunogenic response to the one or more avian antigens or immunogens of interest in the avian subject.

Preferably, the one or more avian antigens or immunogens of interest are derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

More preferably, the foreign sequence encoding the one or more avian antigens or immunogens of interest is derived from avian influenza.

More preferably, the foreign sequence encoding the one or more avian antigens or immunogens of interest is selected from the group consisting of hemagglutinin, nucleoprotein, matrix, or neuraminidase.

More preferably, the foreign sequence encoding the one or more avian antigens or immunogens of interest is selected from the group consisting of hemagglutinin subtype 3, 5, 7, or 9.

The method may further comprise administering an additional vaccine.

Preferably, the avian subject is infected by intramuscular injection of the wing-web, wing-tip, pectoral muscle, or thigh musculature.

The avian subject may also be infected in ovo.

Another aspect of the invention provides a method for inoculation of an avian subject, comprising in ovo administration of a recombinant human adenovirus containing and expressing an heterologous nucleic acid molecule encoding an antigen of a pathogen of the avian subject.

Preferably, the human adenovirus comprises sequences derived from adenovirus serotype 5.

Preferably, the human adenovirus comprises sequences derived from replication-defective adenovirus, non-replicating adenovirus, replication-competent adenovirus, or wild-type adenovirus.

Preferably, the antigen of a pathogen of the avian is derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

More preferably, the antigen of a pathogen of the avian is derived from avian influenza.

More preferably, the avian influenza antigens or immunogens are selected from the group consisting of hemagglutinin, nucleoprotein, matrix, or neuraminidase.

More preferably, the avian influenza antigens or immunogens are selected from the group consisting of hemagglutinin subtype 3, 5, 7, or 9.

The method may further comprise administering an additional vaccine.

Another embodiment of the invention provides an in ovo administration apparatus for delivery of an immunogenic composition to an avian embryo wherein the apparatus contains a recombinant human adenovirus expression vector expressing one or more avian antigens or immunogens of interest, wherein the apparatus delivers to the recombinant human adenovirus to the avian embryo.

Preferably, the human adenovirus expression vector comprises sequences derived from adenovirus serotype 5.

Preferably, the human adenovirus expression vector comprises sequences derived from replication-defective adenovirus, non-replicating human adenovirus, replication-competent adenovirus, or wild-type adenovirus.

Preferably, the one or more avian antigens or immunogens of interest are derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

More preferably, the one or more avian antigens or immunogens of interest are derived from avian influenza.

More preferably, the avian influenza antigens or immunogens are selected from the group consisting of hemagglutinin, nucleoprotein, matrix, or neuraminidase.

More preferably, the avian influenza antigens or immunogens of interest is selected from the group consisting of hemagglutinin subtype 3, 5, 7, or 9.

The method may further comprise administering an additional vaccine.

These and other embodiments are disclosed or are obvious from and encompassed by, the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which.

Figure 1:
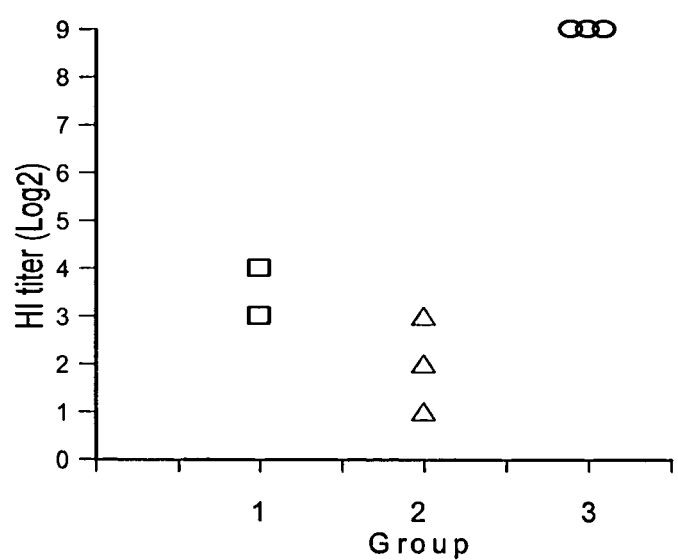
FIG. 1 is a graph depicting the immunization of chickens by in ovo and intramuscular injection of the recombinant adenovirus vector expressing avian influenza HA. Group 1 represents 9-day-old embryonated chicken eggs and Group 2 represents 18-day-old embryonated chicken eggs, respectively, in a volume of 200 µl at a dose of $5 \times 10^{10}$ pfu per egg. In Group 3, the recombinant adenovirus vector expressing avian influenza HA was injected intramuscularly into three 4-week-old chickens in a volume of 100 µl at a dose of $2.5 \times 10^{10}$ pfu per animal.

"Expression" of a gene or nucleic acid encompasses not only cellular gene expression, but also the transcription and translation of nucleic acid(s) in cloning systems and in any other context.

As used herein, a "vector" is a tool that allows or facilitates the transfer of an entity from one environment to another. By way of example, some vectors used in recombinant DNA techniques allow entities, such as a segment of DNA (such as a heterologous DNA segment, such as a heterologous cDNA segment), to be transferred into a target cell. The present invention comprehends recombinant vectors that can include viral vectors, bacterial vectors, protozoan vectors, DNA vectors, or recombinants thereof.

With respect to exogenous DNA for expression in a vector (e.g., encoding an epitope of interest and/or an antigen and/or a therapeutic) and documents providing such exogenous DNA, as well as with respect to the expression of transcription and/or translation factors for enhancing expression of nucleic acid molecules, and as to terms such as "epitope of interest", "therapeutic", "immune response", "immunological response", "protective immune response", "immunological composition", "immunogenic composition", and "vaccine composition", inter alia, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990,091 and WO 98/00166 and WO 99/60164 and documents cited therein and documents of record in the prosecution of that patent and those PCT applications, and other documents cited herein or otherwise incorporated herein by reference, can be consulted in the practice of this invention; and, all exogenous nucleic acid molecules, promoters, and vectors cited therein can be used in the practice of this invention. In this regard, mention is also made of U.S. Pat. Nos. 6,706, 693; 6,716,823; 6,348,450; U.S. patent application Ser. Nos. 10/424,409; 10/052,323; 10/116,963; 10/346,021; and WO 99/08713, published Feb. 25, 1999, from PCT/US98/16739.

As used herein, the terms "immunogenic composition" and "immunological composition" and "immunogenic or immunological composition" cover any composition that elicits an immune response against the antigen or immunogen of interest expressed from the adenoviral vectors and viruses of the invention; for instance, after administration into a subject, elicits an immune response against the targeted immunogen or antigen of interest. The terms "vaccinal composition" and "vaccine" and "vaccine composition" covers any composition that induces a protective immune response against the antigen(s) of interest, or which efficaciously protects against the antigen; for instance, after administration or injection into the subject, elicits an protective immune response against the targeted antigen or immunogen or provides efficacious protection against the antigen or immunogen expressed from the inventive adenovirus vectors of the invention. The term "veterinary composition" means any composition comprising a vector for veterinary use expressing a therapeutic protein as, for example, erythropoietin (EPO) or an immunomodulatory protein, such as, for example, interferon (IFN). Similarly, the term "pharmaceutical composition" means any composition comprising a vector for expressing a therapeutic protein.

An "immunologically effective amount" is an amount or concentration of the recombinant vector encoding the gene of interest, that, when administered to a subject, produces an immune response to the gene product of interest.

A "circulating recombinant form" refers to recombinant viruses that have undergone genetic reassortment among two or more subtypes or strains. Other terms used in the context of the present invention is "hybrid form", "recombined form", and "reassortant form".

"Clinical isolates" refer to, for example, frequently used laboratory strains of viruses that are isolated from infected subjects and are reasserted in laboratory cells or subjects with laboratory-adapted master strains of high-growth donor viruses.

"Field isolates" refer to viruses that are isolated from infected subjects or from the environment.

The methods of the invention can be appropriately applied to prevent diseases as prophylactic vaccination or provide relief against symptoms of disease as therapeutic vaccination.

The recombinant vectors of the present invention can be administered to a subject either alone or as part of an immunological or immunogenic composition. The recombinant vectors of the invention can also be used to deliver or administer one or more proteins to a subject of interest by in vivo expression of the protein(s).

It is noted that immunological products and/or antibodies and/or expressed products obtained in accordance with this invention can be expressed in vitro and used in a manner in which such immunological and/or expressed products and/ or antibodies are typically used, and that cells that express such immunological and/or expressed products and/or antibodies can be employed in in vitro and/or ex vivo applications, e.g., such uses and applications can include diagnostics, assays, ex vivo therapy (e.g., wherein cells that express the gene product and/or immunological response are expanded in vitro and reintroduced into the host or animal), etc., see U.S. Pat. No. 5,990,091, WO 99/60164 and WO 98/00166 and documents cited therein. Further, expressed antibodies or gene products that are isolated from herein methods, or that are isolated from cells expanded in vitro following herein administration methods, can be administered in compositions, akin to the administration of subunit epitopes or antigens or therapeutics or antibodies to induce immunity, stimulate a therapeutic response and/or stimulate passive immunity.

The term "human adenovirus" as used herein is intended to encompass all human adenoviruses of the Adenoviridae family, which include members of the Mastadenovirus genera. To date, over fifty-one human serotypes of adenoviruses have been identified (see, e.g., Fields et al., Virology 2, Ch. 67 (3d ed., Lippincott-Raven Publishers)). The adenovirus can be of serogroup A, B, C, D, E, or F. The human adenovirus can be a serotype 1 (Ad1), serotype 2 (Ad2), serotype 3 (Ad3), serotype 4 (Ad4), serotype 6 (Ad6), serotype 7 (Ad7), serotype 8 (Ad8), serotype 9 (Ad9), serotype 10 (Ad10), serotype 11 (Ad11), serotype 12 (Ad12), serotype 13 (Ad13), serotype 14 (Ad14), serotype 15 (Ad15), serotype 16 (Ad16), serotype 17 (Ad17), serotype 18 (Ad18), serotype 19 (Ad19), serotype 19a (Ad19a), serotype 19p (Ad19p), serotype 20 (Ad20), serotype 21 (Ad21), serotype 22 (Ad22), serotype 23 (Ad23), serotype 24 (Ad24), serotype 25 (Ad25), serotype 26 (Ad26), serotype 27 (Ad27), serotype 28 (Ad28), serotype 29 (Ad29), serotype 30 (Ad30), serotype 31 (Ad31), serotype 32 (Ad32), serotype 33 (Ad33), serotype 34 (Ad34), serotype 35 (Ad35), serotype 36 (Ad36), serotype 37 (Ad37), serotype 38 (Ad38), serotype 39 (Ad39), serotype 40 (Ad40), serotype 41 (Ad41), serotype 42 (Ad42), serotype 43

(Ad43), serotype 44 (Ad44), serotype 45 (Ad45), serotype 46 (Ad46), serotype 47 (Ad47), serotype 48 (Ad48), serotype 49 (Ad49), serotype 50 (Ad50), serotype 51 (Ad51), or preferably, serotype 5 (Ad5), but are not limited to these examples.

Also contemplated by the present invention are recombinant vectors, immunogenic compositions, and recombinant adenoviruses that can comprise subviral particles from more than one adenovirus serotype. For example, it is known that adenovirus vectors can display an altered tropism for specific tissues or cell types (Havenga, M. J. E. et al., 2002), and therefore, mixing and matching of different adenoviral capsids, i.e., fiber, or penton proteins from various adenoviral serotypes may be advantageous. Modification of the adenoviral capsids, including fiber and penton can result in an adenoviral vector with a tropism that is different from the unmodified adenovirus. Adenovirus vectors that are modified and optimized in their ability to infect target cells can allow for a significant reduction in the therapeutic or prophylactic dose, resulting in reduced local and disseminated toxicity.

Adenovirus is a non-enveloped DNA virus. Vectors derived from adenoviruses have a number of features that make them particularly useful for gene transfer. As used herein, a "recombinant adenovirus vector" is an adenovirus vector that carries one or more heterologous nucleotide sequences (e.g., two, three, four, five or more heterologous nucleotide sequences). For example, the biology of the adenoviruses is characterized in detail, the adenovirus is not associated with severe human pathology, the virus is extremely efficient in introducing its DNA into the host cell, the virus can infect a wide variety of cells and has a broad host range, the virus can be produced in large quantities with relative ease, and the virus can be rendered replication defective and/or non-replicating by deletions in the early region 1 ("E1") of the viral genome.

The genome of adenovirus is a linear double-stranded DNA molecule of approximately 36,000 base pairs ("bp") with a 55-kDa terminal protein covalently bound to the 5'-terminus of each strand. The Ad DNA contains identical Inverted Terminal Repeats ("ITRs") of about 100 bp, with the exact length depending on the serotype. The viral origins of replication are located within the ITRs exactly at the genome ends. DNA synthesis occurs in two stages. First, replication proceeds by strand displacement, generating a daughter duplex molecule and a parental displaced strand. The displaced strand is single stranded and can form a "panhandle" intermediate, which allows replication initiation and generation of a daughter duplex molecule. Alternatively, replication may proceed from both ends of the genome simultaneously, obviating the requirement to form the panhandle structure.

During the productive infection cycle, the viral genes are expressed in two phases: the early phase, which is the period up to viral DNA replication, and the late phase, which coincides with the initiation of viral DNA replication. During the early phase, only the early gene products, encoded by regions E1, E2, E3 and E4, are expressed, which carry out a number of functions that prepare the cell for synthesis of viral structural proteins (Berk, A. J., 1986). During the late phase, the late viral gene products are expressed in addition to the early gene products and host cell DNA and protein synthesis are shut off. Consequently, the cell becomes dedicated to the production of viral DNA and of viral structural proteins (Tooze, J., 1981).

The E1 region of adenovirus is the first region of adenovirus expressed after infection of the target cell. This region consists of two transcriptional units, the E1A and E1B genes, both of which are required for oncogenic transformation of primary (embryonal) rodent cultures. The main functions of the E1A gene products are to induce quiescent cells to enter the cell cycle and resume cellular DNA synthesis, and to transcriptionally activate the E1B gene and the other early regions (E2, E3 and E4) of the viral genome. Transfection of primary cells with the E1A gene alone can induce unlimited proliferation (immortalization), but does not result in complete transformation. However, expression of E1A, in most cases, results in induction of programmed cell death (apoptosis), and only occasionally is immortalization obtained (Jochemsen et al., 1987). Co-expression of the E1B gene is required to prevent induction of apoptosis and for complete morphological transformation to occur. In established immortal cell lines, high-level expression of E1A can cause complete transformation in the absence of E1B (Roberts, B. E. et al., 1985).

The E1B encoded proteins assist E1A in redirecting the cellular functions to allow viral replication. The E1B 55 kD and E4 33 kD proteins, which form a complex that is essentially localized in the nucleus, function in inhibiting the synthesis of host proteins and in facilitating the expression of viral genes. Their main influence is to establish selective transport of viral mRNAs from the nucleus to the cytoplasm, concomitantly with the onset of the late phase of infection. The E1B 21 kD protein is important for correct temporal control of the productive infection cycle, thereby preventing premature death of the host cell before the virus life cycle has been completed. Mutant viruses incapable of expressing the E1B 21 kD gene product exhibit a shortened infection cycle that is accompanied by excessive degradation of host cell chromosomal DNA (deg-phenotype) and in an enhanced cytopathic effect (cyt-phenotype; Telling et al., 1994). The deg and cyt phenotypes are suppressed when in addition the E1A gene is mutated, indicating that these phenotypes are a function of E1A (White, E. et al., 1988). Furthermore, the EIB 21 kDa protein slows down the rate by which E1A switches on the other viral genes. It is not yet known by which mechanisms E1B 21 kD quenches these E1A dependent functions.

In contrast to, for example, retroviruses, adenoviruses do not integrate into the host cell's genome, are able to infect non-dividing cells, and are able to efficiently transfer recombinant genes in vivo (Brody et al., 1994). These features make adenoviruses attractive candidates for in vivo gene transfer of, for example, an antigen or immunogen of interest into cells, tissues or subjects in need thereof.

Adenovirus vectors containing multiple deletions are preferred to both increase the carrying capacity of the vector and reduce the likelihood of recombination to generate replication competent adenovirus (RCA). Where the adenovirus contains multiple deletions, it is not necessary that each of the deletions, if present alone, would result in a replication defective and/or non-replicating adenovirus. As long as one of the deletions renders the adenovirus replication defective or non-replicating, the additional deletions may be included for other purposes, e.g., to increase the carrying capacity of the adenovirus genome for heterologous nucleotide sequences. Preferably, more than one of the deletions prevents the expression of a functional protein and renders the adenovirus replication defective and/or non-replicating and/or attenuated. More preferably, all of the deletions are deletions that would render the adenovirus replication-defective and/or non-replicating and/or attenuated. However, the invention also encompasses adenovirus and adenovirus vectors that are replication competent and/or wild-type, i.e. comprises all of the adenoviral genes necessary for infection and replication in a subject.

Embodiments of the invention employing adenovirus recombinants may include E1-defective or deleted, or E3-defective or deleted, or E4-defective or deleted or adenovirus vectors comprising deletions of E1 and E3, or E1 and E4, or E3 and E4, or E1, E3, and E4 deleted, or the "gutless" adenovirus vector in which all viral genes are deleted. The adenovirus vectors can comprise mutations in E1, E3, or E4 genes, or deletions in these or all adenoviral genes. The E1 mutation raises the safety margin of the vector because E1-defective adenovirus mutants are said to be replication-defective and/or non-replicating in non-permissive cells, and are, at the very least, highly attenuated. The E3 mutation enhances the immunogenicity of the antigen by disrupting the mechanism whereby adenovirus down-regulates MHC class I molecules. The E4 mutation reduces the immunogenicity of the adenovirus vector by suppressing the late gene expression, thus may allow repeated re-vaccination utilizing the same vector. The present invention comprehends adenovirus vectors of any serotype or serogroup that are deleted or mutated in E1, or E3, or E4, or E1 and E3, or E1 and E4. Deletion or mutation of these adenoviral genes result in impaired or substantially complete loss of activity of these proteins.

The "gutless" adenovirus vector is another type of vector in the adenovirus vector family. Its replication requires a helper virus and a special human 293 cell line expressing both E1a and Cre, a condition that does not exist in natural environment; the vector is deprived of all viral genes, thus the vector as a vaccine carrier is non-immunogenic and may be inoculated multiple times for re-vaccination. The "gutless" adenovirus vector also contains 36 kb space for accommodating antigen or immunogen(s) of interest, thus allowing co-delivery of a large number of antigen or immunogens into cells.

Other adenovirus vector systems known in the art include the AdEasy system (He et al., 1998) and the subsequently modified AdEasier system (Zeng et al., 2001), which were developed to generate recombinant Ad vectors in 293 cells rapidly by allowing homologous recombination between donor vectors and Ad helper vectors to occur in Escherichia coli cells, such as BJ5183 cells, overnight. pAdEasy comprises adenoviral structural sequences that, when supplied in trans with a donor vector such as pShuttle-CMV expressing an antigen or immunogen of interest, results in packaging of the antigen or immunogen (e.g., immunogens and/or antigens) in an adenoviral capsid. The sequence of pAdEasy is well known in the art and is publicly and commercially available through Stratagene.

The present invention can be generated using the AdHigh system (U.S. Patent Provisional Application Ser. No. 60/683,638). AdHigh is a safe, rapid, and efficient method of generating high titers of recombinant adenovirus without the risk of generating RCA, which may be detrimental or fatal to avian subjects. Further, RCA may be pathogenic to humans and undesirable to be present in the food chain. The AdHigh system uses modified shuttle plasmids, such as pAdHigh, to promote the production of RCA-free adenoviruses in permissive cells, such as PER.C6 cells after generating recombinants with an adenovirus backbone plasmid in E. coli cells. These shuttle plasmids contain polylinkers or multiple cloning sites for easy insertion of avian immunogens or antigens such as, for example, avian influenza immunogens or antigens. Recombination of the adenoviral shuttle plasmids in conjunction with an adenoviral helper plasmid such as pAdEasy in bacterial cells (i.e., BJ5183) can be easily implemented to produce the recombinant human adenoviruses expressing avian antigens or immunogens of the invention. Methods of producing recombinant vectors by cloning and restriction analysis are well known to those skilled in the art.

Specific sequence motifs such as the RGD motif may be inserted into the H-I loop of an adenovirus vector to enhance its infectivity. This sequence has been shown to be essential for the interaction of certain extracellular matrix and adhesion proteins with a superfamily of cell-surface receptors called integrins. Insertion of the RGD motif may be advantageously useful in immunocompromised subjects. An adenovirus recombinant is constructed by cloning specific antigen or immunogen or fragments thereof into any of the adenovirus vectors such as those described above. The adenovirus recombinant is used to transduce cells of a vertebrate use as an immunizing agent. (See, for example, U.S. patent application Ser. No. 10/424,409, incorporated by reference).

The adenovirus vectors of the present invention are useful for the delivery of nucleic acids expressing avian antigens or immunogens to cells both in vitro and in vivo. In particular, the inventive vectors can be advantageously employed to deliver or transfer nucleic acids to animal, more preferably avian and mammalian cells. Nucleic acids of interest include nucleic acids encoding peptides and proteins, preferably therapeutic (e.g., for medical or veterinary uses) or immunogenic (e.g., for vaccines) peptides or proteins.

Preferably, the codons encoding the antigen or immunogen of interest are "optimized" codons, i.e., the codons are those that appear frequently in, i.e., highly expressed avian genes, instead of those codons that are frequently used by, for example, influenza. Such codon usage provides for efficient expression of the antigen or immunogen in human or avian cells. In other embodiments, for example, when the antigen or immunogen of interest is expressed in bacteria, yeast or other expression system, the codon usage pattern is altered to represent the codon bias for highly expressed genes in the organism in which the antigen or immunogen is being expressed. Codon usage patterns are known in the literature for highly expressed genes of many species (e.g., Nakamura et al., 1996; Wang et al, 1998; McEwan et al. 1998).

As a further alternative, the adenovirus vectors can be used to infect a cell in culture to express a desired gene product, e.g., to produce a protein or peptide of interest. Preferably, the protein or peptide is secreted into the medium and can be purified therefrom using routine techniques known in the art as well as those provided herein. Signal peptide sequences that direct extracellular secretion of proteins are known in the art and nucleotide sequences encoding the same can be operably linked to the nucleotide sequence encoding the peptide or protein of interest by routine techniques known in the art. Alternatively, the cells can be lysed and the expressed recombinant protein can be purified from the cell lysate. Preferably, the cell is an animal cell, more preferably an avian or mammalian cell. Also preferred are cells that are competent for transduction by adenoviruses.

Such cells include PER.C6 cells, 911 cells, and HEK293 cells. The invention also comprehends the use of avian cells, such as, but not limited to, avian embryonic fibroblasts, such as DF-1 cells, avian stem cells such as those described in U.S. Pat. Nos. 6,872,561; 6,642,042; 6,280,970; and 6,255, 108, incorporated by reference, avian lymphoblasts, avian epithelial cells, among others, such as chicken embryo-derived cell strain CHCC-OU2 (Ogura, H. et al., 1987;

Japanese Patent Publication No. 9-173059), quail-derived cell strain QT-35 (Japanese Patent Publication No. 9-98778). Any avian cell that is competent for infection, transfection, or any type of gene transfer can be used in the practice of the invention.

A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S (Nichirei), TFBM-01 (Nichirei), ASF104, among others. Suitable culture media for specific cell types can be found at the American Type Culture Collection (ATCC) or the European Collection of Cell Cultures (ECACC). Culture media can be supplemented with amino acids such as L-glutamine, salts, anti-fungal or anti-bacterial agents such as Fungizone®, penicillin-streptomycin, animal serum, and the like. The cell culture medium can optionally be serum-free.

The present invention also provides vectors useful as vaccines. The immunogen or antigen can be presented in the adenovirus capsid, alternatively, the antigen can be expressed from an antigen or immunogen introduced into a recombinant adenovirus genome and carried by the inventive adenoviruses. The adenovirus vector can provide any antigen or immunogen of interest. Examples of immunogens are detailed herein.

The antigens or immunogens are preferably operably associated with the appropriate expression control sequences. Expression vectors include expression control sequences, such as an origin of replication (which can be bacterial origins, e.g., derived from bacterial vectors such as pBR322, or eukaryotic origins, e.g., autonomously replicating sequences (ARS)), a promoter, an enhancer, and necessary information processing sites, such as ribosome binding sites, RNA splice sites, polyadenylation sites, packaging signals, and transcriptional terminator sequences.

For example, the recombinant adenovirus vectors of the invention can contain appropriate transcription/translation control signals and polyadenylation signals (e.g., polyadenylation signals derived from bovine growth hormone, SV40 polyadenylation signal) operably associated with the antigen or immunogen sequence(s) to be delivered to the target cell. A variety of promoter/enhancer elements may be used depending on the level and tissue-specific expression desired. The promoter can be constitutive or inducible (e.g., the metallothionein promoter), depending on the pattern of expression desired. The promoter may be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) or tissue(s) of interest. Brain-specific, hepatic-specific, and muscle-specific (including skeletal, cardiac, smooth, and/or diaphragm-specific) promoters are contemplated by the present invention. Mammalian and avian promoters are also preferred.

The promoter can advantageously be an "early" promoter. An "early" promoter is known in the art and is defined as a promoter that drives expression of a gene that is rapidly and transiently expressed in the absence of de novo protein synthesis. The promoter can also be a "strong" or "weak" promoter. The terms "strong promoter" and "weak promoter" are known in the art and can be defined by the relative frequency of transcription initiation (times per minute) at the promoter. A "strong" or "weak" promoter can also be defined by its affinity to RNA polymerase.

More preferably, the antigens or immunogens are operatively associated with, for example, a human cytomegalovirus (CMV) major immediate-early promoter, a simian virus 40 (SV40) promoter, a β-actin promoter, an albumin promoter, an Elongation Factor 1-α (EF1-α) promoter, a PγK promoter, a MFG promoter, or a Rous sarcoma virus promoter. Other expression control sequences include promoters derived from immunoglobin genes, adenovirus, bovine papilloma virus, herpes virus, and so forth. Any mammalian viral promoter can also be used in the practice of the invention, in addition to any avian viral promoter. Among avian promoters of viral origin, the promoters of immediate early (i.e., ICP4, ICP27) genes of the infectious laryngotracheitis virus (ILTV) virus, early (i.e., thymidine kinase, DNA helicase, ribonucleotide reductase) or late (i.e., gB, gD, gC, gK), of the Marek's disease virus, (i.e., gB, gC, pp 38, pp 14, ICP4, Meq) or of the herpes virus of turkeys (i.e., gB, gC, ICP4) can be used in the methods and vectors of the present invention. Moreover, it is well within the purview of the skilled artisan to select a suitable promoter that expresses the antigen or immunogen of interest at sufficiently high levels so as to induce or elicit an immunogenic response to the antigen or immunogen, without undue experimentation.

It has been speculated that driving heterologous nucleotide transcription with the CMV promoter can result in downregulation of expression in immunocompetent animals (see, e.g., Guo et al., 1996). Accordingly, it is also preferred to operably associate the antigen or immunogen sequences with, for example, a modified CMV promoter that does not result in this down-regulation of antigen or immunogen expression.

The vectors of the invention can also comprise a polylinker or multiple cloning site ("MCS"), which can advantageously be located downstream of a promoter. The polylinker provides a site for insertion of the antigen or immunogen molecules that are "in-frame" with the promoter sequence, resulting in "operably linking" the promoter sequence to the antigen or immunogen of interest. Multiple cloning sites and polylinkers are well known to those skilled in the art. As used herein, the term "operably linked" means that the components described are in a relationship permitting them to function in their intended manner.

Depending on the vector, selectable markers encoding antibiotic resistance may be present when used for in vitro amplification and purification of the recombinant vector, and, in the context of the commercially available AdEasy, AdEasier, and AdHigh adenoviral systems, to monitor homologous recombination between a donor vector and an adenoviral helper vector. The AdEasy, AdEasier, and AdHigh systems facilitate homologous recombination between a donor vector and an adenoviral helper vector at the ITR sequences. Each vector comprises a different antibiotic resistance gene, and by dual selection, recombinants expressing the recombined vector can be selected. Examples of such antibiotic resistance genes that can be incorporated into the vectors of the invention include, but are not limited to, ampicillin, tetracycline, neomycin, zeocin, kanamycin, bleomycin, hygromycin, chloramphenicol, among others.

In embodiments wherein there is more than one antigen or immunogen, the antigen or immunogen sequences may be operatively associated with a single upstream promoter and one or more downstream internal ribosome entry site (IRES) sequences (e.g., the picornavirus EMC IRES sequence).

In embodiments of the invention in which the antigen or immunogen sequence(s) will be transcribed and then translated in the target cells, specific initiation signals are generally required for efficient translation of inserted protein coding sequences. These exogenous translational control sequences, which may include the ATG initiation codon and adjacent sequences, can be of a variety of origins, both natural and synthetic.

Any avian antigen or immunogen derived from an avian pathogen can be used in the methods and recombinant vectors of the invention. Preferred antigens or immunogens include, but are not limited to, antigens or immunogens derived from avian influenza virus, such as hemagglutinin, neuraminidase, matrix, and nucleoprotein antigens or immunogens, infectious bursal disease virus antigens such as VP1, VP1s1, VP1s2, VP2 (Heine, H. G. et al., 1991; Dormitorio, T. V. et al., 1997; and Cao, Y. C. et al., 1998), VP2S, VP3, VP4, VP4S and VP5, Marek's disease virus antigens like thymidine kinase, gA, gB, gC, gD, gE, gH, gI, and gL (Coussens et al. 1988); Ross et al. 1989); Ross et al. 1991); International Publication No. WO 90/02803 (1990); Brunovskis and Velicer, 1995); and Yoshida et al. 1994), Herpesviruses such as infectious laryngotracheitis virus antigens including gA, gB, gD, gE, gI, and gG (Veits, J. et al 2003), avian infectious bronchitis virus antigens such as spike glycoprotein, integral membrane protein M, small membrane protein E, and polyprotein (Casais, R. et al 2003), avian reovirus antigens such as capsid, sigma NS, sigma A, sigma B, and sigma C proteins (Spandidos, D. A. et al, 1976), poxviruses including avipox, fowlpox, canarypox, pigeonpox, quailpox, and dovepox antigens such as thymidine kinase, avian polyomavirus antigens such as VP1, VP2, VP3, and VP4 (Rott, O. et al 1988), Newcastle Disease virus antigens such as HN, P, NP, M, F, and L proteins (reviewed in Alexander, D. J., 1990), avian pneumovirus antigens SH, F, G and N (Seal, B. S., 2000), avian rhinotracheitis virus antigens such as glycoprotein, matrix, fusion, and nucleocapsid (Cook, J. K., 1990), avian reticuloendotheliosis virus antigens such as p29, envelope, gag, protease, and polymerase (Dornburg, R. 1995), avian retroviruses including avian carcinoma virus antigens gag, pol, and env, avian endogenous virus gag, pol, env, capsid, and protease (Rovigatti, U. G. et al, 1983), avian erythroblastosis virus gag, erbA, erbB (Graf, T. et al, 1983), avian hepatitis virus core protein, pol, and surface protein (Cova, L. et al, 1993), avian anemia virus VP1, VP2, VP3 (Rosenberger, J. K. et al, 1998), avian enteritis virus antigens polymerase, 52K protein, penton, Ma, and core proteins (Pitcovski, J. et al., 1988), Pacheco's disease virus IE protein, glycoprotein K, helicase, glycoprotein N, VP11-12, glycoprotein H, thymidine kinase, glycoprotein B, and nuclear phosphoprotein (Kaleta E. F., 1990), avian leukemia virus antigens envelope, gag, and polymerase (Graf, T. et al, 1978), avian parvovirus, avian rotavirus antigens like NSP1, NSP2, NSP3, NSP4, VP1, VP2, VP3, VP4, VP5, VP6, and VP7 (Mori, Y. et al, 2003; Borgan, M. A. et al, 2003), avian leukosis virus antigens such as envelope, gag, and polymerase (Bieth, E. et al, 1992); avian musculoaponeurotic fibrosarcoma virus (Kawai, S. et al, 1992), avian myeloblastosis virus antigens p15, p27, envelope, gag, and polymerase, nucleocapsid, and gs-b (Joliot, V. et al., 1993), avian myeloblastosis-associated virus (Perbal, B., 1995), avian myelocytomatosis virus (Petropoulos, C. J., 1997), avian sarcoma virus antigens such as p19 and envelope (Neckameyer, W. S. et al, 1985), and avian spleen necrosis virus gag, envelope, and polymerase (Purchase, H. G. et al, 1975).

Other immunogens/antigens that can be used in the context of the present invention include avian bacterial antigens from *Pasteurella multocida* strains, such as the 39 kDa capsular protein (Ali, H. A. et al, 2004; Rimler, R. B. 2001), 16-kDa outer membrane protein (Kasten, R. W., et al, 1995), lipopolysaccharide (Baert, K. et al, 2005), *Escherichia coli*, such as type 1 fimbriae, P fimbriae, and curli (Roland, K. et al, 2004); F1 pilus adhesin, P pilus adhesin, aerobactin receptor protein, and lipopolysaccharide (Kariyawasam, S. et al, 2002), *Mycoplasma gallisepticum*, such as the major membrane antigen pMGA (also known as P67; Jan, G. et al, 2001; Noormohammadi, A. H. et al, 2002a), TM-1 (Saito, S. et al, 1993), adhesin (Barbour, E. K. et al, 1989), P52 (Jan, G. et al, 2001) serum-plate-agglutination (SPA) antigen (Ahmad, I. et al, 1988), *Mycoplasma gallinaceum, Mycoplasma gallinarum, Mycoplasma gallopavonis, Mycoplasma synoviae*, including antigens such as major membrane antigen MSPB (Noormohammadi, A. H. et al, 2002b) and 165-kDa protein (Ben Abdelmoumen, B. et al, 1999), *Mycoplasma meleagridis, Mycoplasma iowae, Mycoplasma pullorum, Mycoplasma imitans, Salmonella enteritidis* such as flagellin, porins, OmpA, SEF21 and SEF14 fimbriae (Ochoa-Reparaz, J. et al, 2004), *Salmonella enterica* serovars such as *Gallinarum* and *Typhimurium* that express, for example, SEF14 and SEF21 (Li, W. et al, 2004), *Campylobacter jejuni*, such as flagellin, 67-kDa antigen, CjaA, CjaC, and CjaD proteins (Widders, P. R. et al, 1998; Wyszynska, A. et al, 2004), *Haemophilus paragallinarum* such as serogroups A, B, and C antigens like hemagglutinin (Yamaguchi, T. et al, 1988), *Riemerella anatipestifer*, such as bacterin antigens (Higgins, D. A. et al, 2000), *Chlamydia psittaci* strains such as serovar A and 6B and expressing, for example, major outer membrane protein (MOMP) (Vanrompay, D. et al, 1999), *Erysipelothrix rhusiopathiae* including 66-64 kDa protein antigen (Timoney, J. F. et al, 1993), *Erysipelothrix insidiosa* such as bacterin (Bigland, C. H. and Matsumoto, J. J., 1975), *Brucella abortus*, such as antigens P39 and bacterioferrin (Al-Mariri, A. et al, 2001), *Borrelia anserina* such as 22-kilodalton major outer surface protein (Sambri, V. et al, 1999), outer membrane protein P66 (Bunikis, J. et al, 1998), and OspC (Marconi, R. T. et al, 1993), *Alcaligenes faecalis, Streptococcus faecalis, Staphylococcus aureus*, among many others.

The invention also comprehends the use of immunogens/antigens derived from avian protozoal antigens, such as, but not limited to *Eimeria acervulina* such as 3-1E antigen (Lillehoj, H. S. et al, 2005; Ding, X. et al, 2004), apical complex antigens (Constantinoiu, C. C. et al, 2004), and lactate dehydrogenase (Schaap, D. et al, 2004), *Eimeria maxima* such as gam56 and gam82 (Belli, S. I. et al, 2004), 56 and 82 kDa antigen proteins (Belli, S. I. et al, 2002), and EmTFP250 (Witcombe, D. M. et al, 2004), *Eimeria necatrix* such as 35-kD protein (Tajima, O. et al, 2003), *Eimeria tenella* such as the TA4 and $SO_7$ gene products (Wu, S. Q. et al, 2004; Pogonka, T. et al, 2003) and 12-kDa oocyst wall protein (Karim, M. J. et al, 1996), *Eimeria vermiformis, Eimeria adenoeides, Leucocytozoon caulleryi* such as R7 outer membrane antigen (Ito, A., et al, 2005), *Plasmodium relictum, Plasmodium gallinaceum* such as CSP protein (Grim, K. C. et al, 2004) and 17- and 32-kDa protein antigens (Langer, R. C. et al, 2002), and *Plasmodium elongatum*, among others.

A preferred embodiment of the invention utilizes avian influenza viral antigens or immunogens. The invention also provides a recombinant vector expressing various avian antigens or immunogens, such as, for example, a multivalent vaccine or immunogenic composition that can protect avians against multiple avian diseases with a single injection.

Avian influenza viruses have been transmitted to humans, pigs, horses, and even sea mammals, and have been key contributors to the emergence of human influenza pandemics. Influenza viruses, which belong to the Orthomyxoviridae family, are classified as A, B, and C based on antigenic differences in their nucleoprotein (NP) and matrix (M1) protein. All avian influenza viruses are classified as type A. Further subtyping is based on the antigenicity of two surface glycoproteins, hemagglutinin (HA) and neuraminidase (NA). Currently, 15 HA and 9 NA subtypes have been identified among influenza A viruses (Murphy, B. R. et al, 1996; Röhm, C. et al, 1996b). The amino acid sequences of the HA1 region, which is responsible for HA antigenicity, differ from subtype to subtype by 30% or more (Rohm, C. et al, 1996b). Although viruses with all HA and NA subtypes are found in avian species, viral subtypes of mammalian influenza viruses are limited.

Avian influenza A viruses are defined by their virulence; highly virulent types that can cause fowl plagues, and avirulent types that generally cause only mild disease or asymptomatic infection. In rare instances, however, viruses with low pathogenicity in the laboratory cause outbreaks of severe disease in the field. Nonetheless, the morbidity and mortality associated with these viruses tend to be much lower than those caused by lethal viruses.

Highly virulent avian influenza viruses have caused outbreaks in poultry in Australia (1976 [H7] (Bashiruddin, J. B. et al, 1992); 1985 [H7] (Cross, G. M., 1987; Nestorowicz, A. et al, 1987), 1992 [H7] (Perdue, M. L. et al, 1997), 1995 [H7], and 1997 [H7]), England (1979 [H7] (Wood, G. W., et al, 1993) and 1991 [H5] (Alexander, D. J. et al, 1993), the United States (1983 to 1984 [H5] (Eckroade, R. J. et al, 1987), Ireland (1983 to 1984 [H5]) (Kawaoka, Y. et al, 1987), Germany (1979 [H7] (Rohm, C. et al, 1996a), Mexico (1994 to 1995 [H5] (Garcia, M. et al, 1996; Horimoto, T. et al, 1995), Pakistan (1995 [H7] (Perdue, M. L. et al, 1997), Italy (1997 [H5]), and Hong Kong (1997 [H5] (Claas, E. J. et al, 1988). Without wishing to be bound by any one theory, it is believed that all of the pathogenic avian influenza A viruses are of the H5 or H7 subtype, although the reason for this subtype specificity remains unknown. There appears to be no association of NA subtypes with virulent viruses. Two additional subtypes, H4 [A/Chicken/Alabama/7395/75 (H4N8)] (Johnson, D. C. et al, 1976) and H10 [A/Chicken/Germany/N/49 (H10N7)], have been isolated from chickens during severe fowl plague-like outbreaks.

The structures of influenza A viruses are quite similar (Lamb, R. A. et al, 1996). By electron microscopy, the viruses are pleomorphic, including virions that are roughly spherical (approximately 120 nm in diameter) and filamentous. Two distinct types of spikes (approximately 16 nm in length), corresponding to the HA and NA molecules, reside on the surface of the virions. These two glycoproteins are anchored to the lipid envelope derived from the plasma membrane of host cells by short sequences of hydrophobic amino acids (transmembrane region). HA is a type I glycoprotein, containing an N-terminal ectodomain and a C-terminal anchor, while NA is a type II glycoprotein, containing an N-proximal anchor and a C-terminal ectodomain. HA enables the virion to attach to cell surface sialyloligosaccharides (Paulson, J. C., 1985) and is responsible for its hemagglutinating activity (Hirst, G. K., 1941). HA elicits virus-neutralizing antibodies that are important in protection against infection. NA is a sialidase (Gottschalk, A., 1957) that prevents virion aggregation by removing cell and virion surface sialic acid (the primary moiety in sialyloligosaccharides recognized by HA) (Paulson, J. C., 1985). Antibodies to NA are also important in protecting hosts (Webster, R. G., et al, 1988).

In addition to HA and NA, a limited number of M1 proteins are integrated into the virions (Zebedee, S. L. et al, 1988). They form tetramers, have H1 ion channel activity, and, when activated by the low pH in endosomes, acidify the inside of the virion, facilitating its uncoating (Pinto, L. H. et al, 1992). M1 protein that lies within the envelope is thought to function in assembly and budding. Eight segments of single-stranded RNA molecules (negative sense, or complementary to mRNA) are contained within the viral envelope, in association with NP and three subunits of viral polymerase (PB1, PB2, and PA), which together form a ribonucleoprotein (RNP) complex that participates in RNA replication and transcription. NS2 protein, now known to exist in virions (Richardson, J. C. et al, 1991; Yasuda, J. et al, 1993), is thought to play a role in the export of RNP from the nucleus (O'Neill, R. E. et al, 1998) through interaction with M1 protein (Ward, A. C. et al, 1995). NS1 protein, the only nonstructural protein of influenza A viruses, has multiple functions, including regulation of splicing and nuclear export of cellular mRNAs as well as stimulation of translation (Lamb, R. A. et al, 1996). Its major function is believed to counteract the interferon activity of the host, since an NS1 knockout virus was viable although it grew less efficiently than the parent virus in interferon-non-defective cells (Garcia-Sastre, A. et al, 1988).

The avian influenza immunogens or antigens useful in the present invention include, but are not limited to, HA, NA, as well as M1, NS2, and NS1. Particularly preferred avian influenza immunogens or antigens are HA and NA. The avian influenza immunogens or antigens can be derived from any known strain of AI, including all avian influenza A strains, clinical isolates, field isolates, and reassortments thereof. Examples of such strains and subtypes include, but are not limited to, H10N4, H10N5, H10N7, H10N8, H10N9, H11N1, H11N13, H11N2, H11N4, H11N6, H11N8, H11N9, H12N1, H12N4, H12N5, H12N8, H13N2, H13N3, H13N6, H13N7, H14N5, H14N6, H15N8, H15N9, H16N3, H1N1, H1N2, H1N3, H1N6, H2N1, H2N2, H2N3, H2N5, H2N7, H2N8, H2N9, H3N1, H3N2, H3N3, H3N4, H3N5, H3N6, H3N8, H4N1, H4N2, H4N3, H4N4, H4N5, H4N6, H4N8, H4N9, H5N1, H5N2, H5N3, H5N7, H5N8, H5N9, H6N1, H6N2, H6N4, H6N5, H6N6, H6N7, H6N8, H6N9, H7N1, H7N2, H7N3, H7N5, H7N7, H7N8, H8N4, H8N5, H9N1, H9N2, H9N3, H9N5, H9N6, H9N7, H9N8, and H9N9. The invention also relates to the use of mutated or otherwise altered avian influenza immunogens or antigens that reflect, among other things, antigenic drift and antigenic shift.

The antigenicity of influenza viruses changes gradually by point mutation (antigenic drift) or drastically by genetic reassortment (antigenic shift) (Murphy, B. R. et al, 1996). Immunological pressure on HA and NA is thought to drive antigenic drift. Antigenic shift can be caused by either direct transmission of nonhuman influenza viruses to humans or the reassortment of genes from two different influenza viruses that have infected a single cell (Webster, R. G. et al, 1982). Theoretically, 256 different combinations of RNA can be produced from the shuffling of the eight different genomic segments of the virus. Genetic reassortment is well documented both in vitro and in vivo under laboratory conditions (Webster, R. G. et al, 1975). More importantly, mixed infections occur relatively frequently in nature and can lead to genetic reassortment, resulting in new field isolates, hybrid forms, or reassortant forms (Bean, W. J. et al, 1980; Hinshaw, V. S. et al, 1980; Young, J. F., et al, 1979). Reemergence of a previously circulating virus is another mechanism by which antigenic shift can occur.

Thus, the invention also concerns the use of avian influenza immunogens or antigens that have undergone antigenic drift or antigenic shift, including clinical isolates of avian influenza, field or environmental isolates of avian influenza, hybrid forms, and reassortant forms of avian influenza. Moreover, the invention comprehends the use of more than one avian influenza immunogen or antigen in the vectors and methods disclosed herein, delivered either in separate recombinant vectors, or together in one recombinant vector so as to provide a multivalent avian influenza vaccine or immunogenic composition that stimulates or modulates immunogenic response to one or more avian influenza strains and/or hybrids.

Many domestic and wild avian species are infected with influenza viruses. These include chickens, turkeys, ducks, guinea fowl, domestic geese, quail, pheasants, partridge, mynah birds, passerines, psittacines, budgerigars, gulls, shorebirds, seabirds, and emu (Easterday, B. C. et al, 1997; Webster, R. G. et al, 1988). Some infected birds show symptoms of influenza, while others do not. Among domestic avian species, turkeys are the most frequently involved in outbreaks of influenza; chickens have also been involved but less frequently. Avian influenza A viruses produce an array of syndromes in birds, ranging from asymptomatic to mild upper respiratory infections to loss of egg production to rapidly fatal systemic disease (Eckroade, R. J. et al, 1987). The severity of disease depends on multiple factors, including the virulence of the virus, the immune status and diet of the host, accompanying bacterial infections, and stresses imposed on the host. Depending on their pathogenicity in chickens and turkeys, avian influenza A viruses are classified as virulent (capable of causing fowl plague) or avirulent (causing mild or asymptomatic disease). Even when highly pathogenic for one avian species, influenza A viruses may not be pathogenic for another avian species (Alexander, D. J. et al, 1986). For example, ducks are typically resistant to viruses that are lethal in chickens. As another example, A/Turkey/Ireland/1378/85 (H5N8), which readily kills chickens and turkeys, does not cause disease symptoms in ducks, even though it can be detected in a variety of internal organs and in the blood of infected birds (Kawaoka, Y. et al, 1987).

Influenza viruses are secreted from the intestinal tract into the feces of infected birds (Kida, H., et al, 1980; Webster, R. G. et al, 1978). The modes of transmission can be either direct or indirect; they include contact with aerosol and other virus-contaminated materials. Since infected birds excrete large amounts of virus in their feces, many different items can become contaminated (e.g., feed, water, equipment, and cages) and contribute to dissemination of the virus. Waterborne transmission may provide a mechanism for the year-to-year perpetuation of avian influenza viruses in natural waterfowl habitats. The typical signs and symptoms manifested by commercial avians, such as poultry infected with highly pathogenic avian influenza viruses include decreased egg production, respiratory signs, rales, excessive lacrimation, sinusitis, cyanosis of unfeathered skin (especially the combs and wattles), edema of the head and face, ruffled feathers, diarrhea, and nervous system disorders.

The number of presenting features depends on the species and age of the bird, the strain of virus, and accompanying bacterial infections (Easterday, B. C. et al, 1997; Webster, R. G. et al, 1988). Occasionally, a bird will die without showing any signs of illness (Alexander, D. J. et al, 1993; Wood, G. W., et al, 1994). The gross and histological lesions in chickens inoculated with highly pathogenic viruses are quite similar but do show some strain variation (Alexander, D. J. et al, 1986; Mo, I. P. et al, 1997; Swayne, D. E. et al, 1997). Some of the differences among reported cases may reflect differences in experimental conditions, including the route of inoculation, the breed and age of the chickens, and the dose of virus. Swelling of the microvascular endothelium, systemic congestion, multifocal hemorrhages, perivascular mononuclear cell infiltration, and thrombosis are commonly seen in chickens infected with highly virulent viruses. Such viruses replicate efficiently in the vascular endothelium and perivascular parenchymatous cells, a property that can be important for viral dissemination and systemic infection (Kobayashi, Y. et al, 1996; Suarez, D. L. et al, 1998). Viral antigens can also be found in necrotic cardiac myocytes in addition to cells in other organs with necrotic and inflammatory changes (Kobayashi, Y. et al, 1996).

The present invention also relates to methods of expressing one or more antigens or immunogens in a cell. As a preliminary step in the laboratory setting, the antigen or immunogen can instead be replaced by a heterologous nucleotide sequences encoding proteins and peptides that include those encoding reporter proteins (e.g., an enzyme). Reporter proteins are known in the art and include, but are not limited to, Green Fluorescent Protein, β-galactosidase, β-glucuronidase, luciferase, alkaline phosphatase, and chloramphenicol acetyltransferase gene. Many of these reporter proteins and methods of their detection are included as a part of many commercially available diagnostic kits. The antigen or immunogen of interest may encode an antisense nucleic acid, small interfering RNAs (siRNAs), a ribozyme, or other non-translated RNAs, such as "guide" RNAs (Gorman et al., 1998), and the like.

The recombinant vectors and methods of the invention also comprehend the use of therapeutic proteins or adjuvant molecules that can modulate immune responses upon delivery of recombinant vectors or immunogenic compositions. Such therapeutic proteins or adjuvant molecules can include, but are not limited to, immunomodulatory molecules such as interleukins, interferon, and co-stimulatory molecules. Avian cytokines that are known in the art to modulate immune responses in an avian subject are chicken interferon-α (IFNα) (Karaca, K. et al, 1998; Schijns, V. E. et al, 2000), chicken interferon-γ (IFNγ), chicken interleukin-1β (ChIL-1β) (Karaca, K. et al, 1998), chicken interleukin-2 (ChIL-2) (Hilton, L. S. et al, 2002), and chicken myelomonocytic growth factor (cMGF1 York, J. J. et al, 1996; Djeraba, A. et al, 2002). The immunomodulatory molecules can be co-administered with the inventive immunogenic compositions, or alternatively, the nucleic acid of the immunomodulatory molecule(s) can be co-expressed along with the avian immunogens or antigens in the recombinant vectors of the invention.

Expression in the subject of the heterologous sequence, i.e. avian influenza immunogens, can result in an immune response in the subject to the expression products of the antigen or immunogen. Thus, the recombinant vectors of the present invention may be used in an immunological composition or vaccine to provide a means to induce an immune response, which may, but need not be, protective. The molecular biology techniques used in the context of the invention are described by Sambrook et al. (2001).

Even further alternatively or additionally, in the immunogic or immunological compositions encompassed by the present invention, the nucleotide sequence encoding the antigens or immunogens can have deleted therefrom a portion encoding a transmembrane domain. Yet even further alternatively or additionally, the vector or immunogenic composition can further contain and express in a host cell a nucleotide sequence encoding a heterologous tPA signal sequence such as human or avian tPA and/or a stabilizing intron, such as intron II of the rabbit β-globin gene.

The present invention also provides a method of delivering and/or administering a heterologous nucleotide sequence into a cell in vitro or in vivo. According to this method a cell is infected with a recombinant human adenovirus vector according to the present invention (as described in detail herein). The cell may be infected with the adenovirus vector by the natural process of viral transduction. Alternatively, the vector may be introduced into the cell by any other method known in the art. For example, the cell may be contacted with a targeted adenovirus vector (as described below) and taken up by an alternate mechanism, e.g., by receptor-mediated endocytosis. As another example the vector may be targeted to an internalizing cell-surface protein using an antibody or other binding protein.

A vector can be administered to an avian subject in an amount to achieve the amounts stated for gene product (e.g., epitope, antigen, therapeutic, and/or antibody) compositions. Of course, the invention envisages dosages below and above those exemplified herein, and for any composition to be administered to an avian subject, including the components thereof, and for any particular method of administration, it is preferred to determine therefor: toxicity, such as by determining the lethal dose (LD) and $LD_{50}$ in a suitable avian model; and, the dosage of the composition(s), concentration of components therein and timing of administering the composition(s), which elicit a suitable response, such as by titrations of sera and analysis thereof, e.g., by ELISA and/or seroneutralization analysis. Such determinations do not require undue experimentation from the knowledge of the skilled artisan, this disclosure and the documents cited herein.

Examples of compositions of the invention include liquid preparations for orifice, or mucosal, e.g., oral, nasal, anal, vaginal, peroral, intragastric, etc., administration such as suspensions, solutions, sprays, syrups or elixirs; and, preparations for parenteral, epicutaneous, subcutaneous (i.e., through lower neck), intradermal, intraperitoneal, intramuscular (i.e., through wing-web, wing-tip, pectoral, and thigh musculature puncture), intranasal, or intravenous administration (e.g., injectable administration) such as sterile suspensions or emulsions. Reference is made to U.S. Pat. No. 6,716,823 issued Apr. 6, 2004; U.S. Pat. No. 6,706,693 issued Mar. 16, 2004; U.S. Pat. No. 6,348,450 issued Feb. 19, 2002; U.S. application Ser. Nos. 10/052,323 and 10/116,963; and 10/346,021, the contents of which are incorporated herein by reference and which disclose immunization and delivery of immunogenic or vaccine compositions through a non-invasive mode of delivery, i.e. epicutaneous and intranasal administration. Other methods of administration and delivery to avians include administering the recombinant vectors or immunogenic compositions in drinking water or feed, wherein the dose of vaccine can be selected between $10^1$ and $10^4$ per animal.

For intramuscular injections, administration can occur through the breast (pectoral), leg (upper thigh/lateral flank musculature), wing-web (patagium), under wings (axilla), and wing-tip. The length and diameter (gauge) of the needle used should be such that it will allow delivery of the vaccine to the center of the chosen muscle.

A particularly preferred method of administration is in ovo delivery (Gildersleeve, R. P., 1993a; Gildersleeve, R. P. et al, 1993b; Sharma, J. M., 1985; Sharma, J. M. et al, 1984). In ovo delivery is emerging as a promising method for mass immunization of avians as administration of a uniform dose of vaccines by a robotic injector is both labor- and time-saving (Johnston et al., 1997; Oshop et al., 2002). To date, over 80% of U.S. commercial broiler chickens are treated in ovo with a mechanized injector against Marek's disease (Wakenell et al., 2002). This method is also being used increasingly to administer infectious bursal disease (IBD) and Newcastle disease (ND) vaccines. Immune responses have also been elicited in chickens by in ovo delivery of DNA vaccines (Kapczynski et al., 2003; Oshop et al., 2003) and a replicating alphavirus-vectored vaccine (Schultz-Chemy et al., 2000). Compared with their replicating counterparts, DNA and viral vectored in ovo vaccines and immunogenic compositions are less likely to kill or harm the embryo and Ad vectors in particular have a higher compliance rate due to their incompetence to replicate in ovo.

Mechanized systems, apparatuses, and devices, such as those commercially available as INOVOJECT®, gently injects compounds, vaccines, and immunogenic compositions in precisely calibrated volumes without causing trauma to the developing embryo, thereby reducing chick handling, improving hatchery manageability through automation, and reducing costs of live production. INOVOJECT® and other mechanized systems, devices, or apparatuses, work by gently lowering an injection head onto the top of the egg and a small diameter hollow punch pierces a small opening in the shell. A needle descends through a tube to a controlled depth (usually 2.54 cm), a small, pre-determined volume of vaccine, immunogenic composition, or compound is delivered to the embryo, and then the needle is withdrawn and cleansed in a sterilization wash. Methods of in ovo vaccine and gene delivery can be found in U.S. Pat. Nos. 4,458,630; RE 35973; 6,668,753; 6,601,534; 6,506,385; 6,395,961; 6,286,455; 6,244,214; 6,240,877; 6,032,612; 5,784,992; 5,699,751; 5,438,954; 5,339,766; 5,176,101; 5,136,979; 5,056,464; 4,903,635; 4,681,063; U.S. application Ser. No. 10/686,762, filed on Oct. 16, 2003; Ser. No. 10/216,427, filed on Aug. 9, 2002; Ser. No. 10/074,714, filed on Feb. 13, 2002; and Ser. No. 10/043,025, filed on Jan. 9, 2002, the contents of which are expressly incorporated by reference. Accordingly, the invention contemplates a device or apparatus for in ovo delivery or administration of the recombinant vectors, vaccine or immunogenic compositions described herein. The device or apparatus can optionally comprise the recombinant human adenovirus vectors or immunogenic compositions of the present invention, i.e. can be pre-loaded with the vectors or immunogenic compositions for in ovo administration into an avian.

The invention also comprehends sequential administration of inventive compositions or sequential performance of herein methods, e.g., periodic administration of inventive compositions such as in the course of therapy or treatment for a condition and/or booster administration of immunological compositions and/or in prime-boost regimens; and, the time and manner for sequential administrations can be ascertained without undue experimentation.

Further, the invention comprehends compositions and methods for making and using vectors, including methods for producing gene products and/or immunological products and/or antibodies in vivo and/or in vitro and/or ex vivo (e.g., the latter two being, for instance, after isolation therefrom from cells from a host that has had an administration according to the invention, e.g., after optional expansion of such cells), and uses for such gene and/or immunological products and/or antibodies, including in diagnostics, assays, therapies, treatments, and the like.

Vector compositions are formulated by admixing the vector with a suitable carrier or diluent; and, gene product and/or immunological product and/or antibody compositions are likewise formulated by admixing the gene and/or immunological product and/or antibody with a suitable carrier or diluent; see, e.g., U.S. Pat. No. 5,990,091, WO 99/60164, WO 98/00166, documents cited therein, and other documents cited herein, and other teachings herein (for instance, with respect to carriers, diluents and the like).

In such compositions, the recombinant vectors may be in admixture with a suitable veterinarily or pharmaceutically acceptable carrier, diluent, or excipient such as sterile water, physiological saline, glucose or the like. The compositions can also be lyophilized. The compositions can contain auxiliary substances, such as wetting or emulsifying agents, pH buffering agents, adjuvants, gelling or viscosity enhancing additives, preservatives, flavoring agents, colors, and the like, depending upon the route of administration and the preparation desired.

DMSO has been known to enhance the potency of vaccine and immunogenic compositions, particularly in regard to in ovo delivery of vectors or immunogenic compositions comprising vectors. DMSO is thought to enhance the potency of vaccines by increasing the permeability of cellular membranes (Oshop et al, 2003). Other agents or additives that are capable of permeabilizing cells, reducing the viscosity of amniotic fluid, and exhibiting a higher compliance rate as compared to DMSO can be used in the formulation of vaccines or immunogenic compositions, especially when administered by in ovo delivery. Absorption of a variety of proteins, such as insulin, leptin, and somatotropin, have been shown to be enhanced by surfactants such as tetradecyl maltoside (TDM) without appreciable side effects, following intranasal administration (Arnold, et al, 2004). The present invention therefore comprehends the use of TDM in the methods and compositions described herein.

Formulations containing 0.125% TDM can cause moderate alterations in cell morphology, while higher concentrations of TDM (i.e., 0.5%) can transiently induce more extensive morphological changes. TDM is believed to enhance vector delivery in an in ovo setting due to the viscous nasal mucus in mammals and amniotic fluid of embryonated avian eggs. The safety profile of TDM as described in Arnold, et al (2004) is also particularly advantageous to promote the health of immunized avians and compliance for entering the food chain.

The quantity of vector to be administered will vary for the subject and condition being treated and will vary from one or a few to a few hundred or thousand micrograms of body weight per day and preferably the dose of vaccine or immunogenic composition being chosen preferably between $10^1$-$10^6$ plaque forming units (PFU), preferably $10^2$-$10^5$ PFU per bird. For injection, vaccines containing the above titer should be diluted with a pharmaceutically or veterinarily acceptable liquid such as physiological saline to a final volume of approximately 0.1 ml or 0.01 ml in the case of wing web administration. The vectors and methods of the present invention permit vaccination in ovo and vaccination of 1-day old-chicks, as well as vaccination of older chicks and adults.

A vector can be non-invasively administered to an avian subject in an amount to achieve the amounts stated for gene product (e.g., epitope, antigen, therapeutic, and/or antibody) compositions. Of course, the invention envisages dosages below and above those exemplified herein, and for any composition to be administered to an avian subject, including the components thereof, and for any particular method of administration, it is preferred to determine therefor: toxicity, such as by determining the lethal dose (LD) and $LD_{50}$ in a suitable avian model; and, the dosage of the composition(s), concentration of components therein and timing of administering the composition(s), which elicit a suitable response, such as by titrations of sera and analysis thereof, e.g., by ELISA and/or seroneutralization analysis. Such determinations do not require undue experimentation from the knowledge of the skilled artisan, this disclosure and the documents cited herein.

Recombinant vectors can be administered in a suitable amount to obtain in vivo expression corresponding to the dosages described herein and/or in herein cited documents. For instance, suitable ranges for viral suspensions can be determined empirically. If more than one gene product is expressed by more than one recombinant, each recombinant can be administered in these amounts; or, each recombinant can be administered such that there is, in combination, a sum of recombinants comprising these amounts.

In vector or plasmid compositions employed in the invention, dosages can be as described in documents cited herein or as described herein or as in documents referenced or cited in herein cited documents. Advantageously, the dosage should be a sufficient amount of plasmid to elicit a response analogous to compositions wherein the antigen(s) are directly present; or to have expression analogous to dosages in such compositions; or to have expression analogous to expression obtained in vivo by recombinant compositions.

However, the dosage of the composition(s), concentration of components therein and timing of administering the composition(s), which elicit a suitable immunological response, can be determined by methods such as by antibody titrations of sera, e.g., by ELISA and/or seroneutralization assay analysis. Such determinations do not require undue experimentation from the knowledge of the skilled artisan, this disclosure and the documents cited herein. And, the time for sequential administrations can be likewise ascertained with methods ascertainable from this disclosure, and the knowledge in the art, without undue experimentation.

The immunogenic or immunological compositions contemplated by the invention can also contain an adjuvant. Suitable adjuvants include fMLP (N-formyl-methionyl-leucyl-phenylalanine; U.S. Pat. No. 6,017,537) and/or acrylic acid or methacrylic acid polymer and/or a copolymer of maleic anhydride and of alkenyl derivative. The acrylic acid or methacrylic acid polymers can be cross-linked, e.g., with polyalkenyl ethers of sugars or of polyalcohols. These compounds are known under the term "carbomer" (*Pharmeuropa*, Vol. 8, No. 2, June 1996). A person skilled in the art may also refer to U.S. Pat. No. 2,909,462 (incorporated by reference), which discusses such acrylic polymers cross-linked with a polyhydroxylated compound containing at least 3 hydroxyl groups: in one embodiment, a polyhydroxylated compound contains not more than 8 hydroxyl groups; in another embodiment, the hydrogen atoms of at least 3 hydroxyls are replaced with unsaturated aliphatic radicals containing at least 2 carbon atoms; in other embodiments, radicals contain from about 2 to about 4 carbon atoms, e.g., vinyls, allyls and other ethylenically unsaturated groups. The unsaturated radicals can themselves contain other substituents, such as methyl. The products sold under the name Carbopol® (Noveon Inc., Ohio, USA) are particularly suitable for use as an adjuvant. They are cross-linked with an allyl sucrose or with allylpentaerythritol, as to which, mention is made of the products Carbopol® 974P, 934P, and 971P.

As to the copolymers of maleic anhydride and of alkenyl derivative, mention is made of the EMA® products (Monsanto), which are copolymers of maleic anhydride and of ethylene, which may be linear or cross-linked, for example cross-linked with divinyl ether. Also, reference may be made to U.S. Pat. No. 6,713,068 and Regelson, W. et al., 1960; incorporated by reference).

Cationic lipids containing a quaternary ammonium salt are described in U.S. Pat. No. 6,713,068, the contents of which are incorporated by reference, can also be used in the methods and compositions of the present invention. Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994), to form DMRIE-DOPE.

A recombinant vaccine or immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is available under the name Provax® (IDEC Pharmaceuticals, San Diego, Calif.).

The recombinant adenovirus, or recombinant adenoviral vector expressing one or more antigen or immunogen of interest, e.g., vector according to this disclosure, can be preserved and/or conserved and stored either in liquid form, at about 5° C., or in lyophilized or freeze-dried form, in the presence of a stabilizer. Freeze-drying can be according to well-known standard freeze-drying procedures. The pharmaceutically acceptable stabilizers may be SPGA (sucrose phosphate glutamate albumin; Bovarnick, et al., 1950), carbohydrates (e.g., sorbitol, mannitol, lactose, sucrose, glucose, dextran, trehalose), sodium glutamate (Tsvetkov, T. et al., 1983; Israeli, E. et al., 1993), proteins such as peptone, albumin or casein, protein containing agents such as skimmed milk (Mills, C. K. et al., 1988; Wolff, E. et al., 1990), and buffers (e.g., phosphate buffer, alkaline metal phosphate buffer). An adjuvant and/or a vehicle or excipient may be used to make soluble the freeze-dried preparations.

The invention will now be further described by way of the following non-limiting Examples, given by way of illustration of various embodiments of the invention and are not meant to limit the present invention in any fashion.

EXAMPLES

Example 1: Construction of an Ad Vector Encoding the A/Panama/2007/99 HA

The influenza virus strain, A/Panama/2007/99 (H3N2) (SEQ ID NOs: 1, 2), selected for vaccine production in 2003-2004, was provided by the Centers for Disease Control (CDC). The hemagglutinin (HA) gene was cloned by reverse transcription of the influenza RNA, followed by amplification of the HA gene with polymerase chain reaction (PCR) using the following primers in Table 1.

TABLE 1

Primers Used in Construction of Ad vectors

| Primer | Sequence |
|---|---|
| 5' HA | 5'-CACACAGGTACCGCCATGAAGACTATCATTGCTTTGAGC-3' (SEQ ID NO: 9) |
| 3' HA | 5'-CACACAGGTACCTCAAATGCAAATGTTGCACC-3' (SEQ ID NO: 10) |

These primers contain sequences that anneal to the 5' and 3' ends of the A/Panama/2007/99 HA gene, as well as sequences corresponding to an eukaryotic ribosomal binding site (Kozak, 1986) immediately upstream from the HA initiation ATG codon, and KpnI sites for subsequent cloning. The KpnI fragment containing the full-length HA gene was inserted into the KpnI site of pShuttle-CMV (He et al., 1998) (provided by T. He) in the correct orientation under transcriptional control of the human cytomegalovirus (CMV) early promoter. An E1/E3-defective Ad5 vector encoding the A/Panama/2007/99 HA (AdPNM2007/99.H3) was generated in human 293 cells using a simplified recombination system as described (Zeng et al., 2001).

The AdPNM2007/99.H3 vector was validated by sequencing both 5' and 3' junctions between the HA insert and vector. HI antibodies against A/Panama/2007/99 were elicited in mice after intranasal administration of AdPNM2007/99.H3.

Example 2: Immunization of Chickens by in Ovo and Intramuscular Injection of a Recombinant Ad Vector Immunization of chickens by inoculation of a human Ad-vectored vaccine has not been heretofore reported. Since Ad5 is not naturally found in birds, this vector was believed to be unable to infect and/or replicate in chicken cells efficiently. Surprisingly, serum HI titers of 512 were achieved in all 3 chickens two weeks after intramuscular injection of AdPNM2007/99.H3 (FIG. 1).

When AdPNM2007/99.H3 vectors were injected into 9-day-old and 18-day-old embryonated chicken eggs, serum HI titers of 8 and 16 were achieved in the former, and HI titers of <4, 4, and 8 were achieved in the latter two weeks post-hatch. The results suggest that the E1/E3-defective human Ad5 vector can be used as a vaccine carrier in avians due to its competence to transduce and inability to replicate in avian cells. The relatively low HI titers induced by in ovo vaccination may be attributed to, among other things, the dosage and the age of the embryos. The Ad5 vector may have transduced part of the chicken embryo through binding of its fiber to the coxsackievirus and adenovirus receptor (CAR) found on the surface of chicken cells (Tan et al., 2001). An immune response can be elicited in chickens following transduction of only a small number of cells, because Ad is a potent vector capable of protecting the vector DNA by disrupting endosomes after internalization (Curiel, 1994). In addition, at least one of the Ad components, the hexon, is highly immunogenic and confers adjuvant activity to exogenous antigens (Molinier-Frenkel et al., 2002).

The AdPNM2007/99.H3 vector was injected into the amnion of 9-day-old (Group 1) and 18-day-old (Group 2) embryonated chicken eggs, respectively, in a volume of 200 µl at a dose of $5 \times 10^{10}$ pfu per egg. There were 6 eggs per group; however, only 2 birds hatched in Group 1 and 3 birds in Group 2. Serum HI titers were determined as described (Van Kampen et al., 2005) 2 weeks post-hatch. In Group 3, the AdPNM2007/99.H3 vector was injected intramuscularly into three 4-week-old chickens in a volume of 100 µl at a dose of $2.5 \times 10^{10}$ pfu per animal. HI titers were determined two weeks post-immunization.

In Group 1 (in ovo immunization of 9-day-old embryos), HI titers of 8 and 16 were achieved; in Group 2 (in ovo immunization of 18-day-old embryos), HI titers of <4 (arbitrarily assigned a titer of 2), 4, and 8 were achieved; and in Group 3 (intramuscular immunization of 4-week-old chickens), HI titers of 512 were achieved in all three birds. FIG. 1 shows the HI titers on $\log_2$ scale. The squares correspond to HI titers in individual birds in Group 1; while the triangles correlate to HI titers in individual birds in Group 2. The circles correspond to HI titers in individual birds in Group 3.

Example 3: Construction of an Ad Vector Encoding the A/Turkey/Wisconsin/68 H Gene (AdTW68.H5)

The DNA template of the A/Turkey/WI/68 H (SEQ ID NOs: 3, 4) encoding the H of the AI virus strain, was provided by USDA Southeast Poultry Research Laboratory, Athens Ga., and was PCR amplified using the primers shown in Table 2.

TABLE 2

Primers Used in Construction of Ad vectors

| Primer | Sequence |
|---|---|
| 5' HA | 5'CACACAAAGCTTGCCGCCATGGAAAGAATAGTGATTGC3' (SEQ ID NO: 10) |
| 3' HA | 5'CACACAGGATCCATCTGAACTCACAATCCTAGATGC3' (SEQ ID NO: 11) |

These primers contain sequences that anneal to the 5' and 3' ends of the A/Turkey/Wisconsin/68 H gene, an eukaryotic ribosomal binding site (Kozak, 1986) immediately upstream from the H initiation ATG codon, and unique restriction sites for subsequent cloning. The fragment containing the full-length H gene was inserted into the HindIII-BamHI site of the shuttle plasmid pAdApt (provided by Crucell, Leiden, The Netherlands) in the correct orientation under transcriptional control of the human cytomegalovirus (CMV) early promoter. An RCA-free, E1/E3-defective Ad vector encoding the A/Turkey/Wisconsin/68 H gene (AdTW68.H5) was subsequently generated in human PER.C6 cells (provided by Crucell) by co-transfection of pAdApt-TW68.H5 with the Ad5 backbone plasmid pAdEasy1 (He et al., 1998) as described (Shi et al., 2001). The AdTW68.H5 vector was validated by sequencing both 5' and 3' junctions between the H insert and the vector backbone.

Ad-vectored in ovo AI vaccines may be produced rapidly and mass-administered into chicken populations within the context of a superb safety profile in response to an emerging AI pandemic. Large-scale production of RCA-free Ad5 vectors in the well-characterized PER.C6 cell line in serum-free suspension bioreactors (Lewis, 2006) in conjunction with chromatography-mediated purification (Konz, 2005) and buffers that do not require freezers for long-term storage (Evans, 2004) should greatly reduce the production costs of Ad5 vectors. The use of cultured cells instead of embryonated eggs as a substrate for AI vaccine production is significant, particularly during an AI outbreak when fertile eggs may be in short supply. This Ad5-vectored AI vaccine is in compliance with a DIVA strategy because the vector only encodes the viral HA. Thus, analysis of serum HI antibodies together with measurement of anti-AI nucleoprotein by enzyme-linked immunosorbent assay would allow rapid determination of exposure to the AI vaccine or virus.

Although an aerosol AI vaccine may be developed by expressing HA from a Newcastle disease virus vector (Swayne, 2003) or a reassortant influenza virus containing a non-pathogenic influenza virus backbone (Lee, 2004), the RCA-free Ad5-vectored in ovo AI vaccine provides a unique platform capable of arresting HPAI virus infections in immunized birds through automated delivery of a uniform dose of non-replicating AI vaccine that is compatible with a DIVA strategy. Unlike replicating recombinant vectors that are associated with the risk of generating revertants and allow spread of genetically modified organisms in both target and non-target species in the environment, the RCA-free Ad5 vectors will not propagate in the field. In contrast to the reassortant AI virus vaccine that may generate undesirable further reassortments with a concurrently circulating wild influenza virus (Hilleman, 2002), it is not possible for the DNA genome of Ad5 to undergo reassortment with the segmented RNA genome of an influenza virus.

Example 4: In Ovo Inoculation of AdTW68.H5

In ovo inoculation was performed as described (Senne, 1998; Sharma et al., 1982). Before inoculation all embryos were candled for viability, and the site of inoculation marked and disinfected with a solution of 70% ethyl alcohol containing 3.5% iodine. A hole was made in the shell using a rotating drill equipped with a pointed tip. Inoculation was performed by the amnion-allantoic route by use of 1 ml syringes. After inoculation, the hole was sealed with melted paraffin.

Example 5: Serology Post-Inoculation of AdTW68.H5

AI strain A/Turkey/WI/68 was passaged in SPF embryonated chicken eggs to achieve a titer of $10^6$ embryo infective doses 50%/ml. Amnioallantoic fluids were tested for hemagglutinating activity. Antibody titers in individual serum samples were determined by hemagglutination inhibition using 4 hemagglutinating units of the AI virus as described (Swayne et al., 1998, Thayer et al., 1998).

Example 6: Sampling and Quantification of AI Genomes

Oro-pharyngeal samples from individual birds were suspended in 1.0 ml of brain heart infusion medium (Difco, Detroit, Mich.) and stored at −70° C. RNA was extracted by using the RNeasy mini kit (Qiagen). Quantitative real-time RT-PCR was performed with primers specific for type A influenza virus matrix RNA, as described previously (Spackman, 2002). Viral RNA was interpolated from the cycle thresholds by using standard curves generated from known amounts of control A/Ck/Queretaro/14588-19/95 RNA ($10^{1.0}$ to $10^{6.0}$ $EID_{50}$/mL).

Example 7: Immunization of Chickens by in Ovo Inoculation of AdTW68.H5 Followed by Post-Hatch Boost Immunization of chickens by inoculation was accomplished by administering 300 µl of the AdTW68.H5 containing $10^{11}$ viral particles/ml (vp/ml) into SPF embryonated eggs on days 10 or 18 of embryonation. Hatched chicks of each group were equally divided into two groups: half of the chickens were revaccinated via the nasal route with the same dose of AdTW68.H5 at day 15 post-hatch, and the remaining chickens did not receive a booster application post-hatch.

Figure 2:
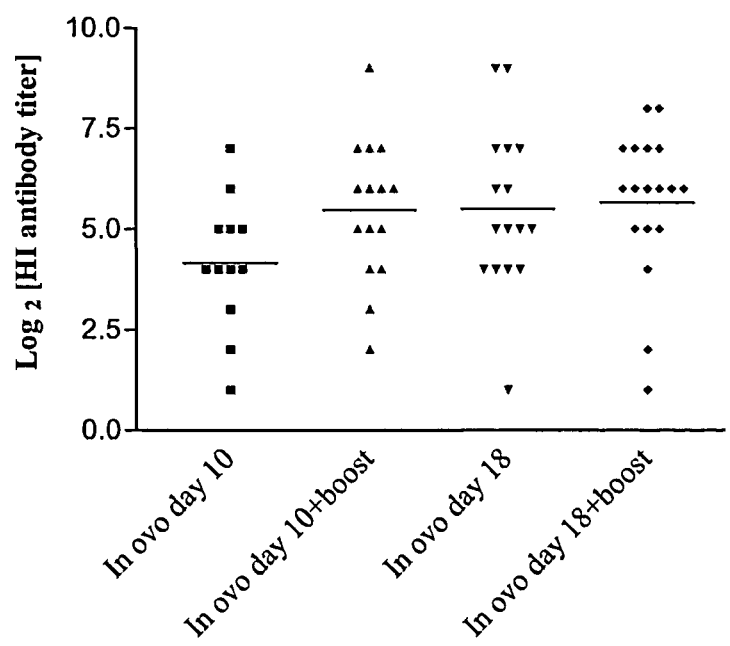
FIG. 2 is a graph depicting the hemagglutination inhibition antibody titers (dots) detected in 28-day-old SPF chickens vaccinated with AdTW68.H5 in ovo only at days 10 or 18 of incubation, and chickens that were vaccinated in ovo at days 10 or 18 of incubation and were boosted by the nasal route at day 15 post-hatch. Bar, geometric mean $\log_2$[HI titer]. No HI titers were detected in naïve control chickens (data not shown).

The HI antibody titers detected in sera obtained at day 28 post-hatch from these bird groups are shown in FIG. 2. Chicks vaccinated in ovo on day 10 of embryonation showed HI titers varying between 2 and 7 $\log_2$ (mean of 4.2); chickens vaccinated at day 10 of embryonation with post-hatch booster application showed HI titers varying between 2 and 9 $\log_2$ (mean of 5.5); chicks vaccinated at day 18 of embryonation showed titers varying between 2 and 9 $\log_2$ (mean of 5.5); and chickens vaccinated at day 18 of embryonation and boosted at day 15 post-hatch showed HI values between 2 and 8 $\log_2$ (mean of 5.7). Overall, in ovo administration of this human Ad-vectored AI vaccine induced a robust immune response against AI in chickens, whereas intranasal instillation of this vectored vaccine into chickens, as recently demonstrated (Gao, 2006), is ineffective.

Example 8: In Ovo Inoculation of AdTW68.H5 Protects Against Lethal Challenge with the Highly Pathogenic Avian Influenza Strain HPAI A/Ck/Queretaro/19/95 (H5N2)

Figure 3:
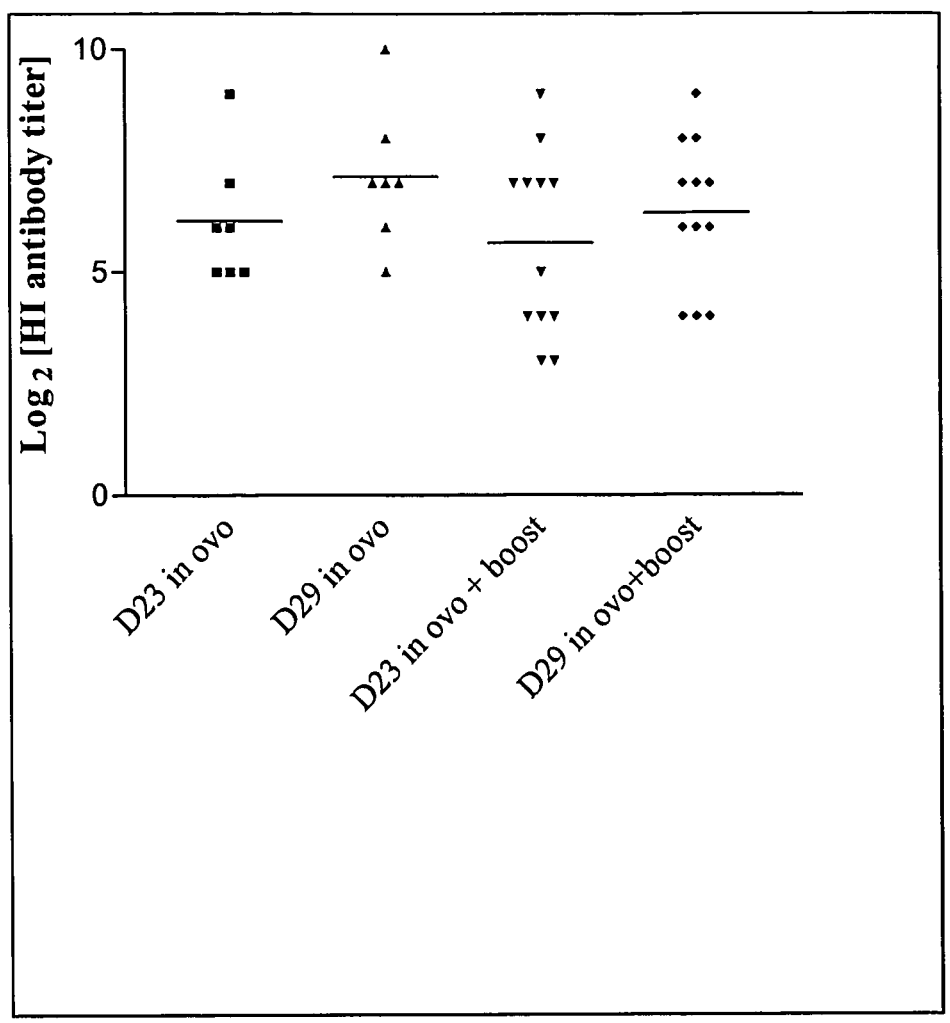
FIG. 3 is a graph depicting the hemagglutination inhibition antibodies in SPF chickens at days 23 and 29 post-hatch either vaccinated in ovo only (7 chicks) at day 18 of embryonation or vaccinated in ovo and boosted intranasally at day 15 post-hatch (12 chicks) with AdTW68.H5. D23 and D29, HI titers at days 23 and 29 post-hatch, respectively; dots, $\log_2$ [HI titer] in individual birds; bar, geometric mean $\log_2$[HI titer]. No HI titers were detected in 11 naïve control chickens at days 23 and 29 post-hatch (data not shown).

19 SPF chicken embryos were immunized by the in ovo route at day 18 of incubation with the same dose of AdTW68.H5 as described in Example 7. Hatched chickens were individually identified by wing band. A group of 12 chickens was boosted via the nasal route at day 15 after hatch and the remaining 7 chickens were not boosted. Blood samples were obtained from each wing-banded bird at days 23 and 29 of age and tested by HI for antibodies against avian influenza strain A/Turkey/Wisconsin/68. Overall, the HI antibody titers detected in these birds (FIG. 3) were similar to the values obtained in the previous trial (FIG. 2). Most birds achieved titers ≥5 $\log_2$. Chicks inoculated only in ovo achieved titers between 5 and 9 $\log_2$ at day 23 post-hatch (FIG. 3). Those chickens either maintained or increased their antibody titers by day 29 post-hatch. In ovo vaccination in conjunction with intranasal booster showed antibody titers varying between 3 and 9 $\log_2$ by day 23 post-hatch (FIG. 3). Similarly as in the previous group, most chicks had increased their titers by 1 or 2 $\log_2$ steps by day 29 post-hatch.

Challenge was performed in biosafety level 3+ facilities by oro-pharyngeal inoculation with $10^5$ embryo infective doses ($EID_{50}$) of the HPAI A/Ck/Queretaro/19/95 ($H_5N_2$) (Horimoto, 1995, Garcia, 1998). The H gene of this challenge strain has 90.1% nucleotide identity and 94.4% deduced amino acid similarity with the H of AI strain A/Tk/WI/68 used in the Ad-vectored vaccine (GenBank accessions U79448 & U79456) (SEQ ID NOS: 5, 6, 7, 8).

Figure 4:
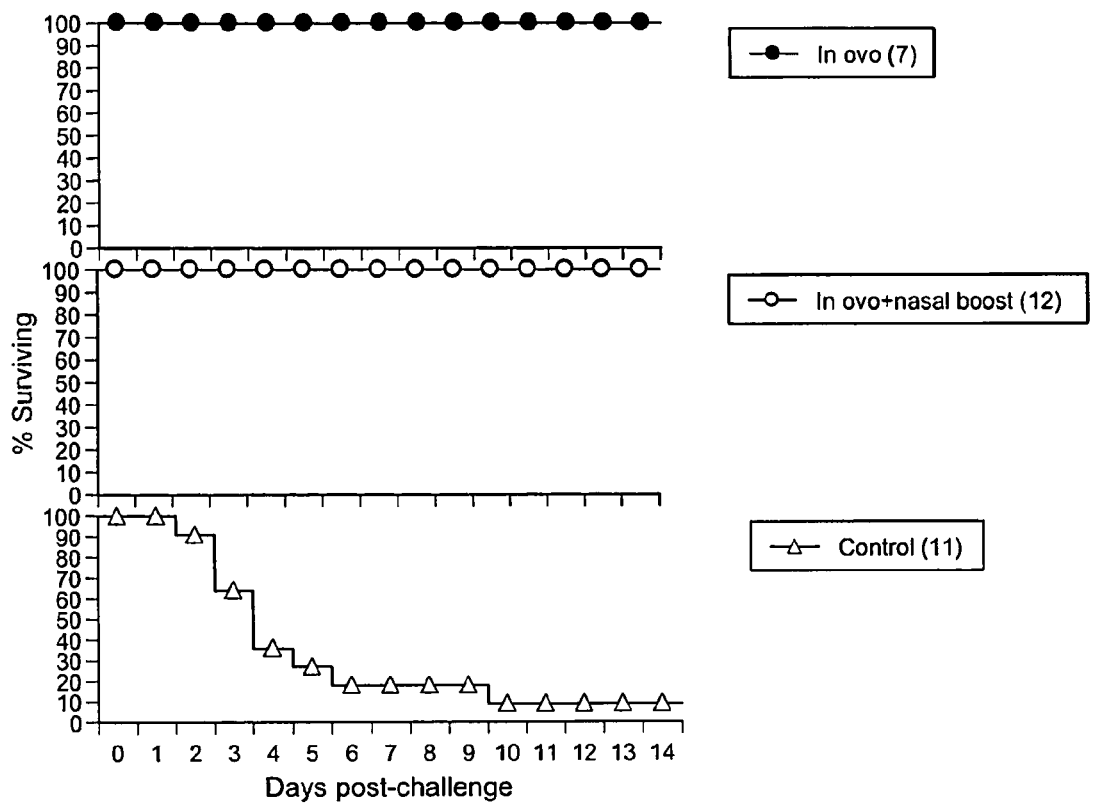
FIG. 4 is a graph depicting in ovo vaccination of day-18 white Leghorn chicken embryos. In ovo vaccination was performed using $10^{11}$ vp of AdTW68.H5 (in ovo). In a separate group, in ovo-vaccinated birds were boosted at day 15 post-hatch by intranasal instillation of AdTW68.H5 with the same dose (in ovo+nasal booster). Naïve embryos without immunization served as negative controls (Control). On day 34 of age chickens were intranasally challenged through the choanal slit with a lethal dose of the highly pathogenic A/Ck/Queretaro/14588-19/95 ($H_5N_2$) AI virus strain. Statistically significant changes in survival were determined throughout the study using the Logrank test (Prism 4.03, GraphPad Software). In ovo vaccination with AdTW68.H5 with or without nasal booster applications significantly protected chickens (100%) against a lethal challenge with AI virus, when compared to unvaccinated controls ($P<0.001$).

A total of 30 chickens, including 7 chicks vaccinated in ovo and 12 chicks vaccinated in ovo and subsequently boosted intranasally at day 15 post-hatch, as well as 11 unvaccinated controls, were challenged at day 34 post-hatch. Challenged birds were observed daily for morbidity and mortality throughout an experimental period of 14 days. Clinical signs of AI, including swelling of comb and wattles, conjunctivitis, anorexia and hypothermia, were observed two days post-challenge in 10 of 11 control birds. Two days later, most survivors in the control group exhibited comb necrosis, swelling of wattles, diarrhea, dehydration, lethargy, and subcutaneous hemorrhages of the leg shank. No signs of disease were developed in any of the vaccinated birds. All birds vaccinated with the AdTW68.H5 (19/19) (in ovo only and in ovo+nasal boost) survived the challenge (FIG. 4).

Figure 5:
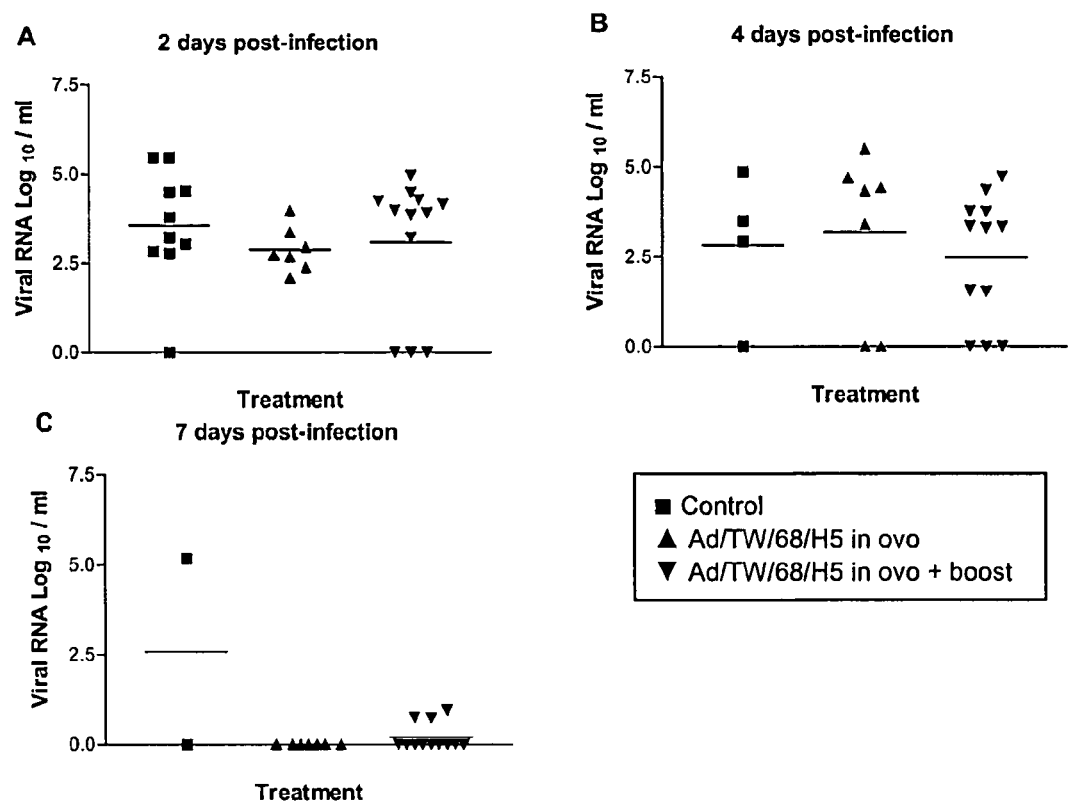
FIG. 5 is a graph depicting A/Ck/Queretaro/14588-19/95 viral RNA quantitated by quantitative real-time RT-PCR (16) in oro-pharyngeal samples from vaccinated and control chickens after intranasal challenge with this highly pathogenic AI virus. Chickens were vaccinated as miformes. Avian subjects can comprise adult avians, avian chicks, and avian embryos/eggs.

Viral genomes of the A/Chicken/Queretaro/19/95 in challenged birds were quantitatively determined by real-time reverse transcriptase-polymerase chain reaction (RT-PCR) in oropharyngeal swabs collected 2, 4, and 7 days post-challenge. There was a significant difference ($P<0.05$) in the concentration of AI viral genomes between vaccinated and unvaccinated chickens 7 days after challenge (FIG. 5). Absence of detectable viral RNA in immunized birds provides evidence that in ovo vaccination elicited an immune response capable of controlling AI virus shedding within a week.

These results collectively show that chickens immunized in ovo with RCA-free human Ad vectors encoding H genes from different influenza viruses (human and avian origin) developed HI antibody titers against the homologous AI virus, and were protected against lethal challenge with a highly pathogenic AI virus strain of the same H type.

Example 9: In Ovo Inoculation of AdTW68.H5 Protects Against Lethal Challenge with the Highly Pathogenic Avian Influenza Strain A/Swan/Mongolia/244L/2005 (H5N1)

To determine whether the AdTW68.H5-vectored AI vaccine can confer protection against a recent H5N1 HPAI virus strain, 31 chickens were vaccinated in ovo with the AdTW68.H5 vector at a dose of $2 \times 10^8$ ifu. Control groups included 10 chickens vaccinated with an Ad5 vector (Ad-CMV-tetC) encoding an irrelevant antigen (tetanus toxin C-fragment) (Shi et al., 2001) and 10 chickens which were not exposed to Ad5 vectors.

Figure 6:
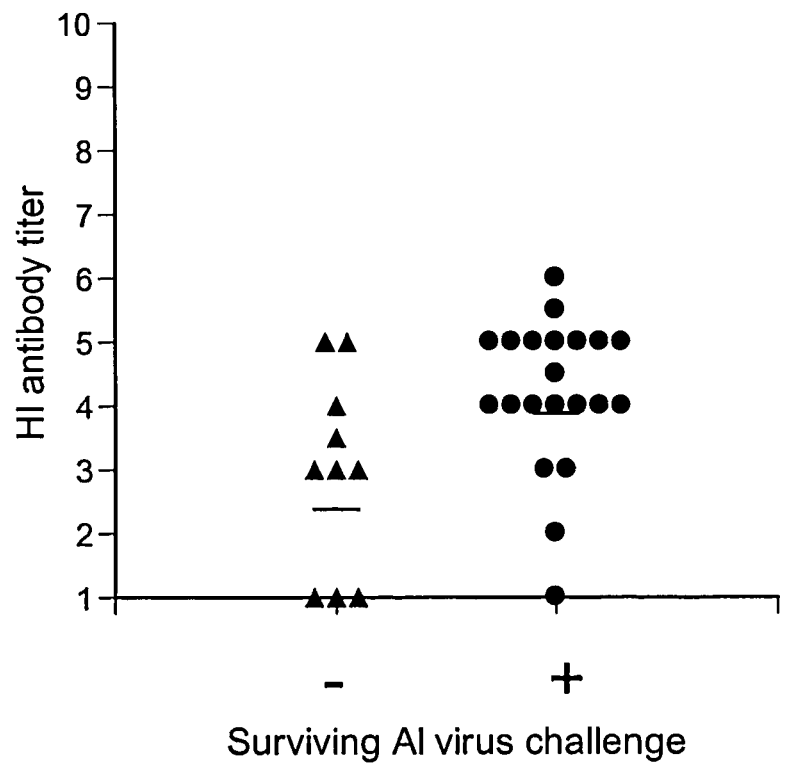
Figure 7:
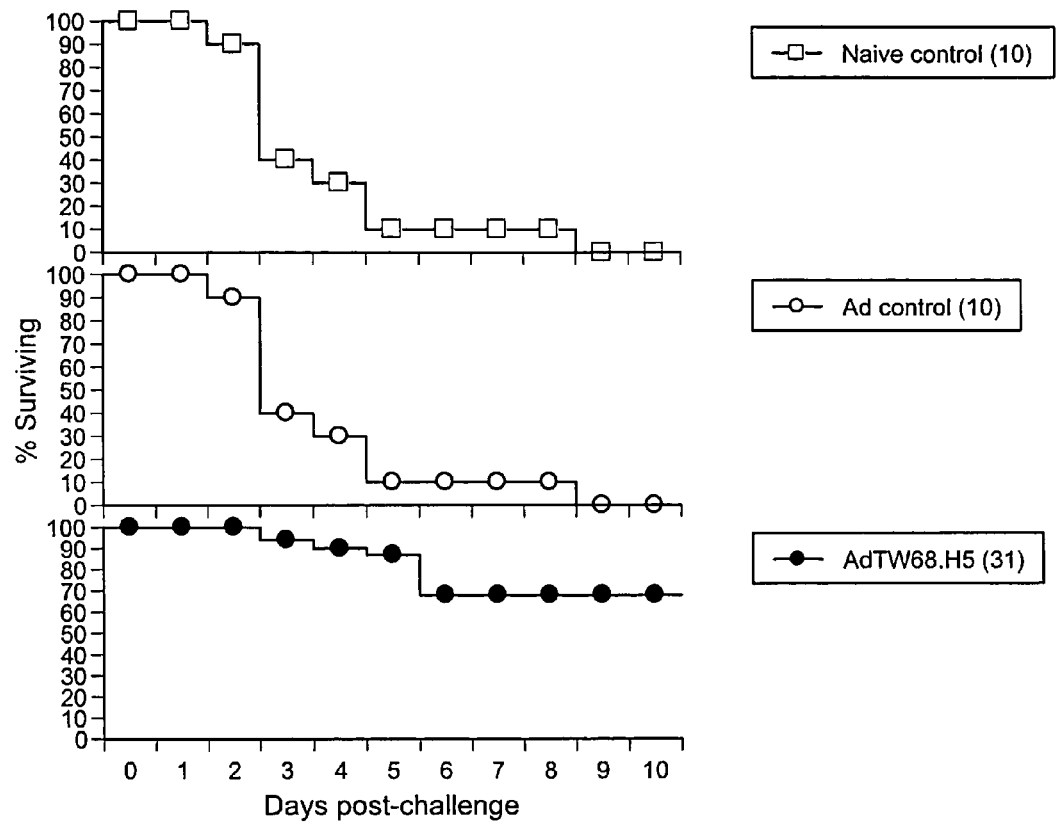

On D31, control and immunized chickens were challenged with the H5N1 AI virus A/Swan/Mongolia/244L/2005 (the HA of this challenge strain has 89% deduced HA amino acid sequence similarity with the HA of the A/Turkey/Wisconsin/68 strain). As shown in FIG. 6, in ovo immunization induced antibodies within a range of 1 and 6 $\log_2$ on D25. None of the unvaccinated (10/10) and AdCMV-tetC-immunized (10/10) birds produced measurable HI antibodies and all died from AI within 9 days post-challenge, whereas 68% (21/31) of the AdTW68.H5-vaccinated birds survived without clinical signs 10 days after the challenge (FIG. 7). Notably, 7 birds in the immunized group with HI titers of ≥3 $\log_2$ (FIG. 6) were still killed by this highly lethal H5N1 AI virus. It is likely that the survival rate against this $H_5N_1$ AI virus may be improved by in ovo vaccination with an Ad5 vector encoding an HA with closer antigenicity.

These results demonstrate that chickens immunized in ovo with an RCA-free human Ad5 vector encoding avian H5 HA could elicit protective immunity against HPAI viruses.

Having thus described in detail preferred embodiments of the present invention, it is to be understood that the invention defined by the appended claims is not to be limited by particular details set forth in the above description as many apparent variations thereof are possible without departing from the spirit or scope thereof.

The invention will now be further described by the following numbered paragraphs:

1. A recombinant human adenovirus expression vector that comprises and expresses an adenoviral DNA sequence, and a promoter sequence operably linked to a foreign sequence encoding one or more avian antigens or immunogens of interest.

2. The expression vector according to paragraph 1, wherein the adenoviral DNA sequence is derived from adenovirus serotype 5 (Ad5).

3. The expression vector according to paragraph 1, wherein the adenoviral DNA sequence is selected from the group consisting of replication-defective adenovirus, non-replicating adenovirus, replication-competent adenovirus, or wild-type adenovirus.

4. The expression vector according to paragraph 1, wherein the promoter sequence is selected from the group consisting of viral promoters, avian promoters, CMV promoter, SV40 promoter, β-actin promoter, albumin promoter, Elongation Factor 1-α (EF1-α) promoter, PγK promoter, MFG promoter, or Rous sarcoma virus promoter.

5. The expression vector according to paragraph 1, wherein the foreign sequence encoding the one or more avian antigens or immunogens of interest is derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

6. The expression vector according to paragraph 5, wherein the foreign sequence encoding the one or more avian antigens or immunogens of interest is derived from one or more avian viruses.

7. The expression vector according to paragraph 5, wherein the foreign sequence encoding the one or more avian antigens or immunogens of interest is derived from avian influenza.

8. The expression vector of paragraph 7, wherein the foreign sequence encoding the one or more avian antigens or immunogens of interest is selected from the group consisting of hemagglutinin, nucleoprotein, matrix, or neuraminidase.

9. The expression vector of paragraph 7, wherein the foreign sequence encoding the one or more avian antigens or immunogens of interest is selected from the group consisting of hemagglutinin subtype 3, 5, 7, or 9.

10. An immunogenic composition or vaccine for in vivo delivery into an avian subject comprising a veterinarily acceptable vehicle or excipient and a recombinant human adenovirus expression vector that comprises and expresses an adenoviral DNA sequence, and a promoter sequence operably linked to a foreign sequence encoding one or more avian antigens or immunogens of interest.

11. The immunogenic composition or vaccine of paragraph 10, wherein the adenoviral DNA sequence is derived from adenovirus serotype 5 (Ad5).

12. The immunogenic composition or vaccine of paragraph 10, wherein the adenoviral DNA sequence is selected from the group consisting of replication-defective adenovirus, non-replicating adenovirus, replication-competent adenovirus, or wild-type adenovirus.

13. The immunogenic composition or vaccine of paragraph 10, wherein the promoter sequence is selected from the group consisting of viral promoters, avian promoters, CMV promoter, SV40 promoter, β-actin promoter, albumin promoter, Elongation Factor 1-α (EF1-α) promoter, PγK promoter, MFG promoter, or Rous sarcoma virus promoter.

14. The immunogenic composition or vaccine of paragraph 10, wherein the foreign sequence encoding the one or more avian antigens or immunogens of interest is derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

15. The immunogenic composition or vaccine of paragraph 10, wherein the foreign sequence encoding the one or more avian antigens or immunogens of interest is derived from one or more avian viruses.

16. The immunogenic composition or vaccine of paragraph 10, wherein the foreign sequence encoding the one or more avian antigens or immunogens of interest is derived from avian influenza.

17. The immunogenic composition or vaccine of paragraph 16, wherein the foreign sequence encoding the one or more avian antigens or immunogens of interest is selected from the group consisting of hemagglutinin, nucleoprotein, matrix, or neuraminidase.

18. The immunogenic composition or vaccine of paragraph 17, wherein the foreign sequence encoding the one or more avian antigens or immunogens of interest is selected from the group consisting of hemagglutinin subtype 3 or 5.

19. The composition or vaccine of paragraph 10, further comprising an adjuvant.

20. The composition or vaccine of paragraph 10, further comprising an additional vaccine.

21. A method of introducing and expressing one or more avian antigens or immunogens in a cell, comprising contacting the cell with a recombinant human adenovirus expression vector that comprises and expresses an adenoviral DNA sequence, and a promoter sequence operably linked to a foreign sequence encoding one or more avian antigens or immunogens of interest., and culturing the cell under conditions sufficient to express the one or more avian antigens or immunogens in the cell.

22. The method of paragraph 21, wherein the cell is a 293 cell.

23. The method of paragraph 21, wherein the cell is a PER.C6 cell.

24. The method of paragraph 21, wherein the one or more avian antigens or immunogens of interest are derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

25. The method of paragraph 24, wherein the foreign sequence encoding the one or more avian antigens or immunogens of interest is derived from one or more avian viruses.

26. The method of paragraph 24, wherein the foreign sequence encoding the one or more avian antigens or immunogens of interest is derived from avian influenza.

27. The method of paragraph 26, wherein the foreign sequence encoding the one or more avian antigens or immunogens of interest is selected from the group consisting of hemagglutinin, nucleoprotein, matrix, or neuraminidase.

28. The method of paragraph 27, wherein the foreign sequence encoding the one or more avian antigens or immunogens of interest is selected from the group consisting of hemagglutinin subtype 3, 5, 7, or 9.

29. A method of introducing and expressing one or more avian influenza antigens or immunogens in an avian embryo, comprising contacting the avian embryo with a recombinant human adenovirus expression vector that comprises and expresses an adenoviral DNA sequence, and a promoter sequence operably linked to a foreign sequence encoding one or more avian antigens or immunogens of interest, thereby obtaining expression of the one or more avian influenza antigens or immunogens in the avian embryo.

30. The method of paragraph 29, wherein the foreign sequence encoding the one or more avian antigens or immunogens of interest is derived from one or more avian viruses.

31. The method of paragraph 29, wherein the foreign sequence encoding the one or more avian antigens or immunogens of interest is derived from avian influenza.

32. The method of paragraph 31, wherein the foreign sequence encoding the one or more avian antigens or immunogens of interest is selected from the group consisting of hemagglutinin, nucleoprotein, matrix, or neuraminidase.

33. The method of paragraph 32, wherein the foreign sequence encoding the one or more avian antigens or immunogens of interest is selected from the group consisting of hemagglutinin subtype 3, 5, 7, or 9.

34. The method of paragraph 29 further comprising administering an additional vaccine.

35. The method of paragraph 29, wherein the contacting occurs by in ovo delivery.

36. A method of eliciting an immunogenic response in an avian subject, comprising administering an immunologically effective amount of the composition of any one of paragraphs 10-20 to the avian subject.

37. A method of eliciting an immunogenic response to avian influenza in an avian subject, comprising administering an immunologically effective amount of the composition of any one of paragraphs 10-20 to the avian subject.

38. A method of eliciting an immunogenic response in an avian subject, comprising infecting the avian subject with an immunologically effective amount of an immunogenic composition comprising a recombinant human adenovirus expression vector that comprises and expresses an adenoviral DNA sequence, and a promoter sequence operably linked to a foreign sequence encoding one or more avian antigens or immunogens of interest, wherein the one or more avian antigens or immunogens of interest are expressed at a level sufficient to elicit an immunogenic response to the one or more avian antigens or immunogens of interest in the avian subject.

39. The method of paragraph 38, wherein the one or more avian antigens or immunogens of interest are derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

40. The method of paragraph 39, wherein the foreign sequence encoding the one or more avian antigens or immunogens of interest is derived from avian influenza.

41. The method of paragraph 40, wherein the foreign sequence encoding the one or more avian antigens or immunogens of interest is selected from the group consisting of hemagglutinin, nucleoprotein, matrix, or neuraminidase.

42. The method of paragraph 41, wherein the foreign sequence encoding the one or more avian antigens or immunogens of interest is selected from the group consisting of hemagglutinin subtype 3, 5, 7, or 9.

43. The method of paragraph 38 further comprising an additional vaccine.

44. The method of paragraph 38, wherein the avian subject is infected by intramuscular injection of the wing-web, wing-tip, pectoral muscle, or thigh musculature.

45. The method of paragraph 38, wherein the avian subject is infected in ovo.

46. A method for inoculation of an avian subject, comprising in ovo administration of a recombinant human adenovirus containing and expressing an heterologous nucleic acid molecule encoding an antigen of a pathogen of the avian subject.

47. The method of paragraph 46, wherein the human adenovirus comprises sequences derived from adenovirus serotype 5.

48. The method of paragraph 46, wherein the human adenovirus comprises sequences derived from replication-defective adenovirus, non-replicating adenovirus, replication-competent adenovirus, or wild-type adenovirus.

49. The method of paragraph 46, wherein the antigen of a pathogen of the avian is derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

50. The method of paragraph 49, wherein the antigen of a pathogen of the avian is derived from avian influenza.

51. The method of paragraph 50, wherein the avian influenza antigens or immunogens are selected from the group consisting of hemagglutinin, nucleoprotein, matrix, or neuraminidase.

52. The method of paragraph 50, wherein the avian influenza antigens or immunogens are selected from the group consisting of hemagglutinin subtype 3, 5, 7, or 9.

53. The method of paragraph 46 further comprising administering an additional vaccine.

54. An in ovo administration apparatus for delivery of an immunogenic composition to an avian embryo wherein the apparatus contains a recombinant human adenovirus expression vector expressing one or more avian antigens or immunogens of interest, wherein the apparatus delivers to the recombinant human adenovirus to the avian embryo.

55. The apparatus of paragraph 54, wherein the human adenovirus expression vector comprises sequences derived from adenovirus serotype 5.

56. The apparatus of paragraph 54, wherein the human adenovirus expression vector comprises sequences derived from replication-defective adenovirus, non-replicating human adenovirus, replication-competent adenOvirus, or wild-type adenovirus.

57. The apparatus of paragraph 54, wherein the one or more avian antigens or immunogens of interest are derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

58. The method of paragraph 57, wherein the one or more avian antigens or immunogens of interest are derived from avian influenza.

59. The method of paragraph 58, wherein the avian influenza antigens or immunogens are selected from the group consisting of hemagglutinin, nucleoprotein, matrix, or neuraminidase.

60. The method of paragraph 58, wherein the avian influenza antigens or immunogens of interest is selected from the group consisting of hemagglutinin subtype 3, 5, 7, or 9.

61. The method of paragraph 58 further comprising administering an additional vaccine.

62. A method of immunizing an avian host comprising inoculation of a non-replicating expression vector that encodes one or more pathogen-derived antigens.

REFERENCES

1. Ahmad, I., Kleven, S. H., Avakian, A. P., and Glisson, J. R. (1988) Sensitivity and specificity of *Mycoplasma gallisepticum* agglutination antigens prepared from medium with artificial liposomes substituting for serum. Avian Dis. 32, 519-26.
2. Al-Mariri, A., Tibor, A., Mertens, P., De Bolle, X., Michel, P., Godefroid, J., Walravens, K., and Letesson, J. J. (2001) Protection of BALB/c mice against *Brucella abortus* 544 challenge by vaccination with bacterioferritin or P39 recombinant proteins with CpG oligodeoxynucleotides as adjuvant. Infect Immun. 69, 4816-22.
3. Alexander, D. J., Lister, S. A., Johnson, M. J., Randall, C. J., and Thomas, P. J. (1993). An outbreak of highly pathogenic avian influenza in turkeys in Great Britain in 1991. Vet. Rec. 132, 535-536.
4. Alexander D. J. (1990) Avian Paramyxoviridae—recent developments. Vet Microbiol. 23, 103-14.
5. Alexander, D. J., Parsons, G., and Manvell, R. J. (1986) Experimental assessment of the pathogenicity of eight avian influenza A viruses of H5 subtype for chickens, turkeys, ducks and quail. Avian Pathol. 15, 647-662.
6. Ali, H. A., Sawada, T., and Noda K. (2004) Protectivity of an immunoaffinity-purified 39 kDa capsular protein of avian *Pasteurella multocida* in mice J. Vet. Med. Sci. 66, 1603-4.
7. Arnold, J. J., Ahsan, F., Meezan, E., and Pillion, D. J. (2004) Correlation of tetradecylmaltoside induced increases in nasal peptide drug delivery with morphological changes in nasal epithelial cells. J. Pharm. Sci. 93, 2205-13.
8. Baert, K., Duchateau, L., De Bocver, S., Cherlet, M., and De Backer, P. (2005) Antipyretic effect of oral sodium salicylate after an intravenous *E. coli* LPS injection in broiler chickens. Br Poult Sci. 46, 137-43.
9. Barbour, E. K., Newman, J. A., Sasipreeyajan, J., Caputa, A. C., and Muneer, M. A. (1989) Identification of the antigenic components of the virulent *Mycoplasma gallisepticum* (R) in chickens: their role in differentiation from the vaccine strain (F). Vet Immunol Immunopathol. 21, 197-206.
10. Baserga, R., and Denhardt, D. T. (eds.)(1992), Antisense Strategies, Annals of the New York Academy of Sciences. Vol. 600, New York Academy of Sciences, New York, N.Y.
11. Bashiruddin, J. B., Gould, A. R., and Westbury, H. A. (1992) Molecular pathotyping of two avian influenza viruses isolated during the Victoria 1976 outbreak. Aust. Vet. J. 69, 140-142.
12. Bean, W. J., Cox, N. J., and Kendal, A. P. (1980) Recombination of human influenza A viruses in nature. Nature 284, 638-640.
13. Beard, C. W., Schnitzlein, W. M., and Tripathy, D. N. (1992). Effect of route of administration on the efficacy of a recombinant fowlpox virus against H5N2 avian influenza. Avian Dis 36, 1052-1055.
14. Behr, J. P. (1994) Gene transfer with synthetic cationic amphiphiles: prospects for gene therapy. Bioconjug Chem. 5, 382-9.
15. Belli, S. I., Lee, M., Thebo, P., Wallach, M. G., Schwartsburd, B., and Smith, N. C. (2002) Biochemical characterisation of the 56 and 82 kDa immunodominant gametocyte antigens from *Eimeria maxima*. Int J. Parasitol. 32, 805-16.
16. Ben Abdelmoumen, B., Roy, R. S., and Brousseau, R. (1999) Cloning of *Mycoplasma synoviae* genes encoding specific antigens and their use as species-specific DNA probes. J Vet Diagn Invest. 11, 162-9.
17. Berk, A. J. (1986) Adenovirus promoters and E1A transactivation. Annu Rev Genet. 20, 45-79.
18. Bieth, E., and Darlix, J. L. (1992) Complete nucleotide sequence of a highly infectious avian leukosis virus. Nucleic Acids Res. 20, 367.

19. Bigland, C. H., and Matsumoto, J. J. (1975) Nonspecific reactions to *Mycoplasma* antigens caused in turkeys sera by *Erysipelothrix insidiosa* bacterin. Avian Dis. 19, 617-21.
20. Borgan, M. A., Mori, Y., Ito, N., Sugiyama, M., and Minamoto, N. (2003) Antigenic analysis of nonstructural protein (NSP) 4 of group A avian rotavirus strain P0-13. Microbiol Immunol. 47, 661-8.
21. Bovarnick, M. R., Miller, J. C., and Snyder, J. C. (1950) The influence of certain salts, amino acids, sugars, and proteins on the stability of rickettsiae. J. Bacteriol. 59, 509-22.
22. Brody, S. L., and Crystal, R. G. (1994) Adenovirus-mediated in vivo gene transfer. Ann N Y Acad. Sci. 716, 90-101; discussion 101-3.
23. Brunovskis, P., and Velicer, L. F. (1995) The Marek's disease virus (MDV) unique short region: alphaherpesvirus-homologous, fowlpox virus-homologous, and MDV-specific genes. Virology 206, 324-38.
24. Bunikis, J., Luke, C. J., Bunikiene, E., Bergstrom, S., and Barbour, A. G. (1998) A surface-exposed region of a novel outer membrane protein (P66) of *Borrelia* spp. is variable in size and sequence. J. Bacteriol. 180, 1618-23.
25. Cao, Y. C., Yeung, W. S., Law, M., Bi, Y. Z., Leung, F. C., and Lim, B. L. (1998) Molecular characterization of seven Chinese isolates of infectious bursal disease virus: classical, very virulent, and variant strains. Avian Dis. 42, 340-51.
26. Casais, R., Dove, B., Cavanagh, D., and Britton, P. (2003) Recombinant avian infectious bronchitis virus expressing a heterologous spike gene demonstrates that the spike protein is a determinant of cell tropism. J. Virol. 77, 9084-9.
27. Chambers, T. M., Kawaoka, Y., and Webster, R. G. (1988). Protection of chickens from lethal influenza infection by vaccinia-expressed hemagglutinin. Virology 167, 414-421.
28. Chiocca, S., Kurzbauer, R., Schaffner, G., Baker, A., Mautner, V., and Cotten, M. (1996). The complete DNA sequence and genomic organization of the avian adenovirus CELO. J Virol 70, 2939-2949.
29. Claas, E. J., Osterhaus, A. E., Van Beek, R., De Jong, J. C., Rimmelzwaan, G. F., Senne, D. A., Krauss, S., Shortridge, K. F., and Webster, R. G. (1998) Human influenza A H5N1 virus related to a highly pathogenic avian influenza virus Lancet 351, 472-477.
30. Constantinoiu, C. C., Lillehoj, H. S., Matsubayashi, M., Tani, H., Matsuda, H., Sasai, K., Baba, E. (2004) Characterization of stage-specific and cross-reactive antigens from *Eimeria acervulina* by chicken monoclonal antibodies. J Vet Med. Sci. 66, 403-8.
31. Cook, J. K. (2000) Avian rhinotracheitis. Rev Sci Tech. 19, 602-13.
32. Crawford, J., Wilkinson, B., Vosnesensky, A., Smith, G., Garcia, M., Stone, H., and Perdue, M. L. (1999) Baculovirus-derived hemagglutinin vaccines protect against lethal influenza infections by avian H5 and H7 subtypes. Vaccine 17, 2265-2274.
33. Crawford, J. M., Garcia, M., Stone, H., Swayne, D., Slemons, R., and Perdue, M. L. (1998). Molecular characterization of the hemagglutinin gene and oral immunization with a waterfowl-origin avian influenza virus. Avian Dis 42, 486-496.
34. Crook, S, and Lebleu, B. (eds.)(1993) Antisense Research and Applications, CRC Press, Boca Raton, Fla.
35. Cross, G. M. (1987) The status of avian influenza in poultry in Australia, p. 96-103. In Proceedings of the Second International Symposium on Avian Influenza.
36. Coussens, P. M., and Velicer, L. F. (1988) Structure and complete nucleotide sequence of the Marek's disease herpesvirus gp57-65 gene. J. Virol. 62, 2373-9.
37. Cova, L., Duflot, A., Prave, M., and Trepo, C. (1993) Duck hepatitis B virus infection, aflatoxin B1 and liver cancer in ducks. Arch Virol Suppl. 8, 81-7.
38. Curiel, D. T. (1994). High-efficiency gene transfer employing adenovirus-polylysine-DNA complexes. Nat Immun 13, 141-164.
39. Ding, X., Lillehoj, H. S., Quiroz, M. A., Bevensee, E., and Lillehoj, E. P. (2004) Protective immunity against *Eimeria acervulina* following in ovo immunization with a recombinant subunit vaccine and cytokine genes. Infect Immun. 72, 6939-44.
40. Djeraba, A., Musset, E., Lowenthal, J. W., Boyle, D. B., Chausse, A. M., Peloille, M., and Quere, P. (2002) Protective effect of avian myelomonocytic growth factor in infection with Marek's disease virus. J. Virol. 76, 1062-70.
41. Dormitorio, T. V., Giambrone, J. J., and Duck, L. W. (1997) Sequence comparisons of the variable VP2 region of eight infectious bursal disease virus isolates. Avian Dis. 41, 36-44.
42. Dornburg, R. (1995) Reticuloendotheliosis viruses and derived vectors. Gene Ther. 2, 301-10.
43. Easterday, B. C., Hinshaw, V. S., and Halvorson, D. A. (1997) Influenza, p. 583-605. In B. W. Calnek, H. J. Barnes, C. W. Beard, L. R. McDougald, and Y. M. Saif (eds), Diseases of Poultry. Iowa State University Press, Ames.
44. Eckroade, R. J. and Bachin, L. A. S. (1987) Avian influenza in Pennsylvania: the beginning, p. 22-32. In Proceedings of the Second International Symposium on Avian Influenza.
45. Eckstein, F. (eds.) (1992) Oligonucleotides and Analogues, A Practical Approach, Oxford University Press, New York, N.Y.
46. Evans, R. K., Nawrocki, K. K., Isopi, L. A., Williams, D. M., Casimiro, D. R., Chin, S., Chen, M., Zhu, D. M., Shiver, J. W., Volkin, D. B. (2004) Development of stable liquid formulations for adenovirus-based vaccines. J. Pharm. Sci. 93, 2458-2475.
47. Fields, B. N., Howley, P. M., Griffin, D. E., Lamb, R. A., Martin, M. A., Roizman, B., Straus, S. E., and Knipe, D. M. (eds)(2001) Fields—Virology, Lippincott, Williams, and Wilkins, Philadelphia, Pa.
48. Francois, A., Chevalier, C., Delmas, B., Eterradossi, N., Toquin, D., Rivallan, G., and Langlois, P. (2004). Avian adenovirus CELO recombinants expressing VP2 of infectious bursal disease virus induce protection against bursal disease in chickens. Vaccine 22, 2351-2360.
49. Fynan, E. F., Webster, R. G., Fuller, D. H., Haynes, J. R., Santoro, J. C., and Robinson, H. L. (1993). DNA vaccines: Protective immunizations by parenteral, mucosal, and gene-gun inoculations. Proc Natl Acad Sci USA 90, 11478-11482.
50. Gao, W., Soloff, A. C. and Lu, X. et al., (2006) Protection of mice and poultry from lethal H5N1 avian influenza virus through adenovirus-based immunization. J. Virol. 80, 1959.
51. Garcia, M., Crawford, J. M., Latimer, J. W., Rivera-Cruz, E., and Perdue, M. L. (1996) Heterogeneity in the haemagglutinin gene and emergence of the highly pathogenic phenotype among recent H5N2 avian influenza viruses from Mexico. J. Gen Virol. 77, 1493-1504.
52. Garcia, A. Johnson, H., Srivastava, D. K., Jayawardene, D. A., Wehr, D. R., Webster, R. G., (1998) Efficacy of inactivated H5N2 influenza vaccines against lethal A/Chicken/Queretaro/19/95 infection. Avian Dis. 42, 248.
53. Garcia-Sastre, A., Egorov, A., Matassov, D., Brandt, S., Levy, D. E., Durbin, J. E., Palese, P., and Muster, T. (1998) Influenza A virus lacking the NS1 gene replicates in interferon-deficient systems. Virology 252, 324-330.
54. Gildersleeve, R. P., (1993) In ovo technology update. Zootec. Int. 73-77.
55. Gildersleeve, R. P., Hoyle, C. M., Miles, A. M., Murray, D. L., Ricks, C. A., Secrest, M. N., Williams, C. J., and Womack, C. L. (1993) Developmental performance of an egg injection machine for administration of Marek's disease vaccine. J. Appl. Poult. Res. 2, 337-346.
56. Gorman, L., Suter, D., Emerick, V., Schumperli, D., and Kole, R. (1998) Stable alteration of pre-mRNA splicing patterns by modified U7 small nuclear RNAs. Proc Natl Acad Sci USA. 95, 4929-34.
57. Gottschalk, A. (1957) The specific enzyme of influenza virus and *Vibrio cholerae*. Biochim. Biophys. Acta 23, 645-646.
58. Graf, T., and Beug, H. (1978) Avian leukemia viruses: interaction with their target cells in vivo and in vitro. Biochim Biophys Acta 516, 269-99.
59. Graf, T., and Beug, H. (1983) Role of the v-erbA and v-erbB oncogenes of avian erythroblastosis virus in erythroid cell transformation. Cell. 34, 7-9.
60. Graham, F. L., and Prevec, L. (1995). Methods for construction of adenovirus vectors. Mol Biotechnol 3, 207-220.
61. Grim, K. C., McCutchan, T., Li, J., Sullivan, M., Graczyk, T. K., McConkey, G., and Cranfield, M. (2004) Preliminary results of an anticircumsporozoite DNA vaccine trial for protection against avian malaria in captive African black-footed penguins (*Spheniscus demersus*). J Zoo Wildl Med. 35, 154-61.
62. Guo, Z. S., Wang, L. H., Eisensmith, R. C., and Woo, S. L. (1996) Evaluation of promoter strength for hepatic gene expression in vivo following adenovirus-mediated gene transfer. Gene Ther. 3, 802-10.
63. Havenga, M. J., Lemckert, A. A., Grimbergen, J. M., Vogels, R., Huisman, L. G., Valerio, D., Bout, A., and Quax, P. H. (2001) Improved adenovirus vectors for infection of cardiovascular tissues. J. Virol. 75, 3335-42.
64. Havenga, M. J., Lemckert, A. A., Ophorst, O. J., van Meijer, M., Germeraad, W. T., Grimbergen, J., van Den Doel, M. A., Vogels, R., van Deutekom, J., Janson, A. A., de Bruijn, J. D., Uytdehaag, F., Quax, P. H., Logtenberg, T., Mehtali, M., and Bout, A. (2002) Exploiting the natural diversity in adenovirus tropism for therapy and prevention of disease. J. Virol. 76, 4612-20.
65. He, T. C., Zhou, S., da Costa, L. T., Yu, J., Kinzler, K. W., Vogelstein, B. (1998) A simplified system for generating recombinant adenovirus. Proc. Nat. Acad. Sci. USA. 95, 2509 (1998).
66. He, T. C., Zhou, S., da Costa, L. T., Yu, J., Kinzler, K. W., and Vogelstein, B. (1998). A simplified system for generating recombinant adenoviruses. Proc Natl Acad Sci USA 95, 2509-2514.
67. Heine, H. G., Haritou, M., Fulla, P., Fahey, K., and Azad, A. (1991) Sequence analysis and expression of the host-protective immunogen VP2 of a variant strain of infectious bursal disease virus which can circumvent vaccination with standard type I strains. J Gen Virol. 72, 1835-43.
68. Higgins, D. A., Henry, R. R., and Kounev, Z. V. (2000) Duck immune responses to *Riemerella anatipestifer* vaccines. Dev Comp Immunol. 24, 153-67.
69. Hilleman, M. R. (2002). Realities and enigmas of human viral influenza: pathogenesis, epidemiology and control. Vaccine 20, 3068-3087.
70. Hinshaw, V. S., Bean, W. J., Webster, R. G., and Sriram, G. (1980) Genetic reassortment of influenza A viruses in the intestinal tract of ducks. Virology 102, 412-419.
71. Hilton, L. S., Bean, A. G., Kimpton, W. G., and Lowenthal, J. W. (2002) Interleukin-2 directly induces activation and proliferation of chicken T cells in vivo. J Interferon Cytokine Res. 22, 755-63.
72. Hirst, G. K. (1941) Agglutination of red cells by allantoic fluid of chick embryos infected with influenza virus. Science 94, 22-23.
73. Horimoto, T., Rivera, E., Pearson, J., Senne, D., Krauss, S., Kawaoka, Y., and Webster, R. G. (1995) Origin and molecular changes associated with emergence of a highly pathogenic H5N2 influenza virus in Mexico. Virology 213, 223-230.
74. Israeli, E., Shaffer, B. T., and Lighthart, B. (1993) Protection of freeze-dried *Escherichia coli* by trehalose upon exposure to environmental conditions. Cryobiology 30, 519-23.
75. Ito A. Gotanda, T., Kobayashi, S., Kume, K., Sugimoto, C., and Matsumura, T. (2005) Increase of antibody titer against *Leucocytozoon caulleryi* by oral administration of recombinant R7 antigen. J. Vet. Med. Sci. 67, 211-3.
76. Jan, G., Le Henaff, M., Fontenelle, C., and Wroblewski, H. (2001) Biochemical and antigenic characterisation of *Mycoplasma gallisepticum* membrane proteins P52 and P67 (pMGA). Arch Microbiol. 177, 81-90.
77. Jochemsen, A. G., Peltenburg, L. T., to Pas, M. F., de Wit, C. M., Bos, J. L., and van der Eb, A. J. (1987) Activation of adenovirus 5 E1A transcription by region E1B in transformed primary rat cells. EMBO J. 6, 3399-405.
78. Johnson, D. C., Maxfield, B. G., and Moulthrop, J. I. (1976) Epidemiologic studies of the 1975 avian influenza outbreak in chickens in Alabama. Avian Dis. 21, 167-177.
79. Johnston, P. A., Liu, H., O'Connell, T., Phelps, P., Bland, M., Tyczkowski, J., Kemper, A., Harding, T., Avakian, A., Haddad, E., et al. (1997). Applications in in ovo technology. Poult Sci 76, 165-178.
80. Joliot, V., Boroughs, K., Lasserre, F., Crochet, J., Dambrine, G., Smith, R. E., and Perbal, B. (1993) Pathogenic potential of myeloblastosis-associated virus: implication of env proteins for osteopetrosis induction. Virology 195, 812-9.
81. Kaleta, E. F. (1990) Herpesviruses of birds—a review. Avian Pathol. 10, 193-211.
82. Kapczynski, D. R., Hilt, D. A., Shapiro, D., Sellers, H. S., and Jackwood, M. W. (2003). Protection of chickens from infectious bronchitis by in ovo and intramuscular vaccination with a DNA vaccine expressing the Si glycoprotein. Avian Dis 47, 272-285.
83. Karaca, K., Sharma, J. M., Winslow, B. J., Junker, D. E., Reddy, S., Cochran, M., and McMillen, J. (1998) Recombinant fowlpox viruses coexpressing chicken type I IFN and Newcastle disease virus HN and F genes: influence of IFN on protective efficacy and humoral responses of chickens following in ovo or post-hatch administration of recombinant viruses. Vaccine. 16, 1496-503.
84. Karim, M. J., Basak, S. C., and Trees, A. J. (1996) Characterization and immunoprotective properties of a monoclonal antibody against the major oocyst wall protein of *Eimeria tenella*. Infect Immun. 64, 1227-32.

85. Kariyawasam, S., Wilkie, B. N., Hunter, D. B., and Gyles, C. L. (2002) Systemic and mucosal antibody responses to selected cell surface antigens of avian pathogenic *Escherichia coli* in experimentally infected chickens. Avian Dis. 46, 668-78.

86. Kasten, R. W., Hansen, L. M., Hinojoza, J., Bieber, D., Ruehl, W. W., and Hirsh, D. C. (1995) *Pasteurella multocida* produces a protein with homology to the P6 outer membrane protein of *Haemophilus influenzae*. Infect Immun. 63, 989-93.

87. Kawai, S., Goto, N., Kataoka, K., Saegusa, T., Shinno-Kohno, H., and Nishizawa, M. (1992) Isolation of the avian transforming retrovirus, AS42, carrying the v-maf oncogene and initial characterization of its gene product. Virology 188, 778-84.

88. Kawaoka, Y., Nestorowicz, A., Alexander, D. J., and Webster, R. G. (1987) Molecular analyses of the hemagglutinin genes of H5 influenza viruses: origin of a virulent turkey strain. Virology 158, 218-227.

89. Kawaoka, Y., Krauss, S., and Webster, R. G. (1989). Avian-to-human transmission of the PB1 gene of influenza A viruses in the 1957 and 1968 pandemics. J Virol 63, 4603-4608.

90. Kida, H., Yanagawa, R., and Matsuoka, Y. (1980) Duck influenza lacking evidence of disease signs and immune response. Infect. Immun. 30, 547-553.

91. Kobayashi, Y., Horimoto, T., Kawaoka, Y., Alexander, D. J., and Itakura, C. (1996) Pathological studies of chickens experimentally infected with two highly pathogenic avian influenza strains. Avian Pathol. 25, 285-304.

92. Konz, J. O. et al. (2005) Serotype specificity of adenovirus purification using anion-exchange chromatography. Hum. Gene Ther. 16, 1346-1353.

93. Kozak, M. (1986). Point mutations define a sequence flanking the AUG initiator codon that modulates translation by eukaryotic ribosomes. Cell 44, 283-292.

94. Lamb, R. A. and Krug, R. M. (1996) Orthomyxoviruses: the viruses and their replication, p. 1353-1395. In B. N. Fields, D. M. Knipe, and P. M. Howley (ed.), Fields virology, $3^{rd}$ ed. Lippincott-Raven, Philadelphia, Pa.

95. Langer, R. C., Li, F., and Vinetz, J. M. Identification of novel *Plasmodium gallinaceum* zygote- and ookinete-expressed proteins as targets for blocking malaria transmission. Infect Immun. 70, 102-6.

96. Lee, C. W., Senne, D. A., and Suarez, D. L. (2004). Generation of reassortant influenza vaccines by reverse genetics that allows utilization of a DIVA (Differentiating Infected from Vaccinated Animals) strategy for the control of avian influenza. Vaccine 22, 3175-3181.

97. Lewis, J. A., Brown, E. L. & Duncan, P. A. (2006) Approaches to the release of a master cell bank of PER.C6 cells; a novel cell substrate for the manufacture of human vaccines. *Dev. Biol. (Basel)* 123, 165-176.

98. Li, W., Watarai, S., Iwasaki, T., and Kodama, H. (2004) Suppression of *Salmonella enterica* serovar Enteritidis excretion by intraocular vaccination with fimbriae proteins incorporated in liposomes. Dev Comp Immunol. 28, 29-38.

99. Lillehoj, H. S., Ding, X., Quiroz, M. A., Bevensee, E., and Lillehoj, E. P. (2005) Resistance to intestinal coccidiosis following DNA immunization with the cloned 3-1E *Eimeria* gene plus IL-2, IL-15, and IFN-gamma. Avian Dis. 49, 112-7.

100. Marconi, R. T., Samuels, D. S., Schwan, T. G., and Garon, C. F. (1993) Identification of a protein in several *Borrelia* species which is related to OspC of the Lyme disease spirochetes. J Clin Microbiol. 31, 2577-83.

101. Mata, J. E., Joshi, S. S., Palen, B., Pirruccello, S. J., Jackson, J. D., Elias, N., Page, T. J., Medlin, K. L., and Iversen, P. L. (1997) A hexameric phosphorothioate oligonucleotide telomerase inhibitor arrests growth of Burkitt's lymphoma cells in vitro and in vivo. Toxicol Appl Pharmacol. 144, 189-97.

102. McEwan, N. R., and Gatherer, D. (1998) Adaptation of standard spreadsheet software for the analysis of DNA sequences. Biotechniques 24, 131-6, 138.

103. Milligan, J. F., Matteucci, M. D., and Martin, J. C. (1993) Current concepts in antisense drug design. J Med. Chem. 36, 1923-37.

104. Mills, C. K., and Gherna, R. L. (1988) Cryopreservation studies of *Campylobacter*. Cryobiology 25, 148-52.

105. Mo, I. P., Brugh, M., Fletcher, O. J., Rowland, G. N., and Swayne, D. E. (1997) Comparative pathology of chickens experimentally inoculated with avian influenza viruses of low and high pathogenicity. Avian Dis. 41, 125-136.

106. Mori, Y., Borgan, M. A., Takayama, M., Ito, N., Sugiyama, M., and Minamoto, N. (2003) Roles of outer capsid proteins as determinants of pathogenicity and host range restriction of avian rotaviruses in a suckling mouse model. Virology 316, 126-34.

107. Molinier-Frenkel, V., Lengagne, R., Gaden, F., Hong, S. S., Choppin, J., Gahery-Segard, H., Boulanger, P., and Guillet, J. G. (2002). Adenovirus hexon protein is a potent adjuvant for activation of a cellular immune response. J Virol 76, 127-135.

108. Murphy, B. R. and Webster, R. G. (1996) Orthomyxoviruses, p. 1397-1445. In B. N. Fields, D. M. Knipe, and P. M. Howley (ed.), Fields virology, $3^{rd}$ ed. Lippincott-Raven, Philadelphia, Pa.

109. Nakamura, Y., Wada, K., Wada, Y., Doi, H., Kanaya, S., Gojobori, T., and Ikemura, T. (1996) Codon usage tabulated from the international DNA sequence databases. Nucleic Acids Res. 24, 214-5.

110. Neckameyer, W. S., and Wang, L. H. (1985) Nucleotide sequence of avian sarcoma virus UR2 and comparison of its transforming gene with other members of the tyrosine protein kinase oncogene family. J. Virol. 53, 879-84.

111. Nestorowicz, A., Kawaoka, Y., Bean, W. J., and Webster, R. G., (1987) Molecular analysis of the hemagglutinin genes of Australian H7N7 influenza viruses: role of passerine birds in maintenance or trainsmission? Virology 160, 411-418.

112. Noormohammadi, A. H., Browning, G. F., Cowling, P. J., O'Rourke, D., Whithear, K. G., and Markham, P. F. (2002a) Detection of antibodies to *Mycoplasma gallisepticum* vaccine ts-11 by an autologous pMGA enzyme-linked immunosorbent assay. Avian Dis. 46, 405-11.

113. Noormohammadi, A. H., Browning, G. F., Jones, J., and Whithear, K. G. (2002b) Improved detection of antibodies to *Mycoplasma synoviae* vaccine MS-H using an autologous recombinant MSPB enzyme-linked immunosorbent assay. Avian Pathol. 31, 611-7.

114. Normile, D. (2004). Influenza: girding for disaster. Vaccinating birds may help to curtail virus's spread. Science 306, 398-399.

115. O'Neill, R. E., Talon, J., and Palese, P. (1998) The influenza virus NEP (NS2 protein) mediates the nuclear export of viral ribonucleoproteins. EMBO J. 17, 288-296.

116. Ochoa-Reparaz, J., Sesma, B., Alvarez, M., Jesus Renedo, M., Irache, J. M., and Gamazo, C. (2004) Humoral immune response in hens naturally infected with 116. ...Salmonella Enteritidis against outer membrane proteins and other surface structural antigens. Vet Res. 35, 291-8.
117. Oshop, G. L., Elankumaran, S., and Heckert, R. A. (2002). DNA vaccination in the avian. Vet Immunol Immunopathol 89, 1-12.
118. Oshop, G. L., Elankumaran, S., Vakharia, V. N., and Heckert, R. A. (2003). In ovo delivery of DNA to the avian embryo. Vaccine 21, 1275-1281.
119. Paulson, J. C. (1985) Interactions of animal viruses with cell surface receptors, p. 131-219. In M. Connor (ed.), The receptors. Academic Press, Inc., Orlando, Fla.
120. Perbal, B. (1995) Pathogenic potential of myeloblastosis-associated viruses. Infect Agents Dis. 4, 212-27.
121. Perdue, M. L., Garcia, M., and Senne, D. (1997) Virulence-associated sequence duplication at the hemagltinin cleavage site of avian influenza viruses. Virus Res. 49, 173-186.
122. Petropoulos, C. J., Appendix 2: Retroviral Taxonomy, protein structure, sequences, and genetic maps. In: Coffin, J. M. (Ed.); RETROVIRUSES: Cold Spring Harbor Laboratory Press, Cold Spring Harbor, N.Y. USA (1997).
123. Pinto, L. H., Holsinger, L. J., and Lamb, R. A. (1992) Influenza virus M2 protein has ion channel activity. Cell 69, 517-528.
124. Pitcovski, J., Mualem, M., Rei-Koren, Z., Krispel, S., Shmueli, E., Peretz, Y., Gutter, B., Gallili, G. E., Michael, A., and Goldberg, D. (1998) The complete DNA sequence and genome organization of the avian adenovirus, hemorrhagic enteritis virus. Virology 249, 307-15.
125. Pogonka, T., Klotz, C., Kovacs, F., and Lucius, R. (2003) A single dose of recombinant Salmonella typhimurium induces specific humoral immune responses against heterologous Eimeria tenella antigens in chicken. Int J Parasitol. 33, 81-8.
126. Purchase, H. G., and Witter, R. L. (1975) The reticuloendotheliosis viruses. Curr Top Microbiol Immunol. 71, 103-24.
127. Rajakumar, A., Swierkosz, E. M., and Schulze, I. T. (1990). Sequence of an influenza virus hemagglutinin determined directly from a clinical sample. Proc Natl Acad Sci USA 87, 4154-4158.
128. Regelson, W., Kuhar, S., Tunis, M., Fields, J., Johnson, J., Gluesenkamp, E. (1960) Synthetic polyelectrolytes as tumour inhibitors. Nature. 186, 778-80.
129. Richardson, J. C., and Akkina, R. K. (1991) NS2 protein of influenza virus is found in purified virus and phosphorylated in infected cells. Arch. Virol. 116, 69-80.
130. Rimler, R. B. (2001) Purification of a cross-protective antigen from Pasteurella multocida grown in vitro and in vivo. Avian Dis. 45, 572-80.
131. Roberts, B. E., Miller, J. S., Kimelman, D., Cepko, C. L., Lemischka, I. R., and Mulligan, R. C. (1985) Individual adenovirus type 5 early region 1A gene products elicit distinct alterations of cellular morphology and gene expression. J. Virol. 56, 404-13.
132. Röhm, C., Süss, J., Pohle, V., and Webster, R. G. (1996a) Different hemagglutinin cleavage site variants of H7N7 in an influenza outbreak in chickens in Leipzig, Germany. Virology 218, 253-257.
133. Röhm, C., Zhou, N. A., Süss, J., Mackenzie, J., and Webster, R. G. (1996b) Characterization of a novel influenza hemagglutinin, H15: criteria for determination of influenza A subtypes. Virology 217, 508-516.
134. Roland, K., Karaca, K., and Sizemore, D. (2004) Expression of Escherichia coli antigens in Salmonella typhimurium as a vaccine to prevent airsacculitis in chickens. Avian Dis. 48, 595-605.
135. Rosenberger, J. K., and Cloud, S. S. (1998) Chicken anemia virus. Poult Sci. 77, 1190-2.
136. Ross, L. J., Sanderson, M., Scott, S. D., Binns, M. M., Doel, T., and Milne, B. (1989) Nucleotide sequence and characterization of the Marek's disease virus homologue of glycoprotein B of herpes simplex virus. J Gen Virol. 70, 1789-804.
137. Ross, L. J., and Binns, M. M. (1991) Properties and evolutionary relationships of the Marek's disease virus homologues of protein kinase, glycoprotein D and glycoprotein I of herpes simplex virus. J Gen Virol. 72, 939-47.
138. Rott, O., Kroger, M., Muller, H., and Hobom, G. (1988) The genome of budgerigar fledgling disease virus, an avian polyomavirus. Virology 165, 74-86.
139. Rovigatti, U. G., and Astrin, S. M. (1983) Avian endogenous viral genes. Curr Top Microbiol Immunol. 103, 1-21.
140. Saito, S., Fujisawa, A., Ohkawa, S., Nishimura, N., Abe, T., Kodama, K., Kamogawa, K., Aoyama, S., Iritani, Y., and Hayashi, Y. (1993) Cloning and DNA sequence of a 29 kilodalton polypeptide gene of Mycoplasma gallisepticum as a possible protective antigen. Vaccine 11, 1061-6.
141. Sambri, V., Marangoni, A., Olmo, A., Storni, E., Montagnani, M., Fabbi, M., and Cevenini, R. (1999) Specific antibodies reactive with the 22-kilodalton major outer surface protein of Borrelia anserina Ni-NL protect chicks from infection. Infect Immun. 67, 2633-7.
142. Sambrook, J., Russell, D. W., and Sambrook, J. (2001) Molecular Cloning, Cold Spring Harbor Press, Cold Spring Harbor, N.Y.
143. Samstag, W., Eisenhardt, S., Offensperger, W. B., and Engels, J. W. (1996) Synthesis and properties of new antisense oligodeoxynucleotides containing benzylphosphonate linkages. Antisense Nucleic Acid Drug Dev. 6, 153-6.
144. Schaap, D., Arts, G., Kroeze, J., Niessen, R., Roosmalen-Vos, S. V., Spreeuwenberg, K., Kuiper, C. M., Beek-Verhoeven, N. V., Kok, J. J., Knegtel, R. M., and Vermeulen, A. N. (2004) An Eimeria vaccine candidate appears to be lactate dehydrogenase; characterization and comparative analysis. Parasitology. 128, 603-16.
145. Schijns, V. E., Weining, K. C., Nuijten, P., Rijke, E. O., and Staeheli, P. (2000) Immunoadjuvant activities of E. coli—and plasmid-expressed recombinant chicken IFN-alpha/beta, IFN-gamma and IL-1beta in 1-day- and 3-week-old chickens. Vaccine. 18, 2147-54.
146. Schultz-cherry, S., Dybing, J. K., Davis, N. L., Williamson, C., Suarez, D. L., Johnston, R., and Perdue, M. L. (2000). Influenza virus (A/HK/156/97) hemagglutinin expressed by an alphavirus replicon system protects chickens against lethal infection with Hong Kong-origin H5N1 viruses. Virology 278, 55-59.
147. Seal, B. S. (2000) Avian pneumoviruses and emergence of a new type in the United States of America. Anim Health Res Rev. 1, 67-72.
148. Senne, D. A., in A laboratory manual for the isolation and identification of avian pathogens Swayne, D. E., Glisson, J. R., Jackwood, M. W., Pearson, J. E., Reed, W. M., Eds. (American Association of Avian Pathologists, Kennett Square, Pa., 1998) pp. 235-240.
149. Sharma, J. M. (1985) Embryo vaccination with infectious bursal disease virus alone or in combination with Marek's disease vaccine. Avian Dis. 27, 134-139.

150. Sharma, J. M. and Burmester, B. R. (1982) Resistance of Marek's disease at hatching in chickens vaccinated as embryos with the turkey herpesvirus. Avian Dis. 26, 134-139.

151. Shi, Z., Zeng, M., Yang, G., Siegel, F., Cain, L. J., van Kampen, K., Elmets, C. A., and Tang, D. C. Protection against tetanus by needle-free inoculation of adenovirus-vectored nasal and epicutaneous vaccines. J. Virol. 75, 11474 (2001).

152. Spackman, E., Senne, D. A., Myers, T. J., Bulaga, L. L., Garber, L. P., Perdue, M. L., Lohman, K., Daum, L. T., Suarez, D. L. Development of a real-time reverse transcriptase PCR assay for type A influenza virus and the avian H5 and H7 hemagglutinin subtypes. J. Clin. Microbiol. 40, 3256 (2002).

153. Spandidos, D. A., and Graham, A. F. (1976) Physical and chemical characterization of an avian reovirus. J. Virol. 19, 968-76.

154. Strauss-Soukup, J. K., Vaghefi, M. M., Hogrefe, R. I., Maher, L. J., 3rd. (1997) Effects of neutralization pattern and stereochemistry on DNA bending by methylphosphonate substitutions. Biochemistry. 36, 8692-8.

155. Suarez D. L., Perdue, M. K., Cox, N., Rowe, T., Bender, C., Huang, J., and Swayne, D. E. (1998) Comparisons of highly virulent H5N1 influenza A viruses isolated from humans and chickens from Hong Kong. J. Virol. 72, 6678-6688.

156. Subbarao, K., Klimov, A., Katz, J., Regnery, H., Lim, W., Hall, H., Perdue, M., Swayne, D., Bender, C., Huang, J., et al. (1998). Characterization of an avian influenza A (H5N1) virus isolated from a child with a fatal respiratory illness. Science 279, 393-396.

157. Swayne, D. E., Perdue, M. L., Garcia, M., Rivera-Cruz, E., and Brugh, M. (1997) Pathogenicity and diagnosis of H5N2 Mexican avian influenza viruses in chickens. Avian Dis. 41, 335-346.

158. Swayne, D. E. (2003). Vaccines for List A poultry diseases: emphasis on avian influenza. Dev Biol (Basel) 114, 201-212.

159. Swayne, D. E., Senne, D. A. and Beard., C. W., in *A laboratory Manual for the Isolation and Identification of Avian Pathogens* D. E. Swayne, J. R. Glisson, M. W. Jackwood, J. E. Pearson, and W. M. Reed, Eds. (American Association of Avian Pathologists, Kennett Square, Pa., 1998) pp. 150-155.

160. Tajima, O., Onaga, H., and Nakamura, T. (2003) An enzyme-linked immunosorbent assay with the recombinant merozoite protein as antigen for detection of antibodies to *Eimeria necatrix*. Avian Dis. 47, 309-18.

161. Tan, P. K., Michou, A. I., Bergelson, J. M., and Cotten, M. (2001). Defining CAR as a cellular receptor for the avian adenovirus CELO using a genetic analysis of the two viral fibre proteins. J Gen Virol 82, 1465-1472.

162. Telling, G. C., Perera, S., Szatkowski-Ozers, M., and Williams, J. (1994) Absence of an essential regulatory influence of the adenovirus E1B 19-kilodalton protein on viral growth and early gene expression in human diploid WI38, HeLa, and A549 cells. J. Virol. 68, 541-7.

163. Thayer, S. G. and Beard., C. W., in *A laboratory Manual for the Isolation and Identification of avian pathogens* D. E. Swayne, J. R. Glisson, M. W. Jackwood, J. E. Pearson, and W. M. Reed, Eds. (American Association of Avian Pathologists, Kennett Square, Pa., 1998) pp. 255-266.

164. Timoney, J. F., and Groschup, M. M. (1993) Properties of a protective protein antigen of *Erysipelothrix rhusiopathiae*. Vet Microbiol. 37, 381-7.

165. Tollis, M., and Di Trani, L. (2002). Recent developments in avian influenza research: epidemiology and immunoprophylaxis. Vet J 164, 202-215.

166. Tooze, J. (1980) DNA Tumor Viruses (Part 2): Moelcular Biology of Tumor Viruses, Cold Spring Harbor Laboratory Press, Cold Spring Harbor, N.Y.

167. Tsvetkov, T., and Brankova, R. (1983) Viability of micrococci and lactobacilli upon freezing and freeze-drying in the presence of different cryoprotectants. Cryobiology 20, 318-23.

168. Ungchusak, K., Auewarakul, P., Dowell, S. F., Kitphati, R., Auwanit, W., Puthavathana, P., Uiprasertkul, M., Boonnak, K., Pittayawonganon, C., Cox, N. J., et al. (2005). Probable person-to-person transmission of avian influenza A (H5N1). N Engl J Med 352, 333-340.

169. Van Kampen, K. R., Shi, Z., Gao, P., Zhang, J., Foster, K. W., Chen, D. T., Marks, D., Elmets, C. A., and Tang, D. C. (2005). Safety and immunogenicity of adenovirus-vectored nasal and epicutaneous influenza vaccines in humans. Vaccine 23, 1029-1036.

170. Vanrompay, D., Cox, E., Volckaert, G., and Goddeeris, B. (1999) Turkeys are protected from infection with *Chlamydia psittaci* by plasmid DNA vaccination against the major outer membrane protein. Clin Exp Immunol. 118, 49-55.

171. Veits, J., Mettenleiter, T. C., and Fuchs, W. (2003) Five unique open reading frames of infectious laryngotracheitis virus are expressed during infection but are dispensable for virus replication in cell culture. J Gen Virol. 84, 1415-25.

172. Wakenell, P. S., Bryan, T., Schaeffer, J., Avakian, A., Williams, C., and Whitfill, C. (2002). Effect of in ovo vaccine delivery route on herpesvirus of turkeys/SB-1 efficacy and viremia. Avian Dis 46, 274-280.

173. Wang, T. T., Cheng, W. C., and Lee, B. H. (1998) A simple program to calculate codon bias index. Mol. Biotechnol. 10, 103-6.

174. Ward, A. C., Castelli, L. A., Lucantoni, A. C., White, J. F., Azad, A. A., and Macreadie, I. G. (1995) Expression and analysis of the NS2 protein of influenza A virus. Arch. Virol. 140, 2067-2073.

175. Webby, R. J., Perez, D. R., Coleman, J. S., Guan, Y., Knight, J. H., Govorkova, E. A., McClain-Moss, L. R., Peiris, J. S., Rehg, J. E., Tuomanen, E. I., and Webster, R. G. (2004). Responsiveness to a pandemic alert: use of reverse genetics for rapid development of influenza vaccines. Lancet 363, 1099-1103.

176. Webster, R. G., and Layer, W. G. (1975) Antigenic variation of influenza viruses, P. 270-314. In E. D. Kilbourne (ed.), The influenza viruses and influenza. Academic Press, Inc., New York, N.Y.

177. Webster, R. G., Yakhno, M. A., Hinshaw, V. S., Bean, W. J., and Murti, K. G. (1978) Intestinal influenza: replication and characterization of influenza viruses in ducks. Virology 84, 268-278.

178. Webster, R. G., Layer, W. G., Air, G. M., and Schild, G. C. (1982) Molecular mechanisms of variation in influenza viruses. Nature 296, 115-121.

179. Webster, R. G., and Kawaoka, Y. (1988) Avian influenza. Crit. Rev. Poult. Biol. 1, 211-246.

180. Webster, R. G., Reay, P. A., and Layer, W. G. (1998) Protection against lethal influenza with neuraminidase. Virology 164, 230-237.

181. White, E., Denton, A., and Stillman, B. (1988) Role of the adenovirus E1B 19,000-dalton tumor antigen in regulating early gene expression. J. Virol. 62, 3445-54.

182. Widders, P. R., Thomas, L. M., Long, K. A., Tokhi, M. A., Panaccio, M., and Apos, E. (1998) The specificity of antibody in chickens immunised to reduce intestinal colonisation with *Campylobacter jejuni*. Vet Microbiol. 64, 39-50.
183. Wolff, E., Delisle, B., Corrieu, G., and Gibert, H. (1990) Freeze-drying of *Streptococcus thermophilus*: a comparison between the vacuum and the atmospheric method. Cryobiology 27, 569-75.
184. Wood, G. W., McCauley, J. W., Bashiruddin, J. B., and Alexander, D. J. (1993) Deduced amino acid sequences at the haemagglutinin cleavage site of avian influenza A viruses of H5 and H7 subtypes. Arch. Virol. 130, 209-217.
185. Wood, G. W., Banks, J., McCauley, J. W., and Alexander, D. J. (1994) Deduced amino acid sequences of the haemagglutinin of H5N1 avian influenza virus isolates from an outbreak in turkeys in Norfolk, England. Arch. Virol. 134, 185-194.
186. Wood, J. M., Major, D., Newman, R. W., Dunleavy, U., Nicolson, C., Robertson, J. S., and Schild, G. C. (2002). Preparation of vaccines against H5N1 influenza. Vaccine 20, S84-S87.
187. Wu, S. Q., Wang, M., Liu, Q., Zhu, Y. J., Suo, X., and Jiang, J. S. (2004) Construction of DNA vaccines and their induced protective immunity against experimental *Eimeria tenella* infection. Parasitol Res. 94, 332-6.
188. Wyszynska, A., Raczko, A., L is, M., and Jagusztyn-Krynicka, E. K. (2004) Oral immunization of chickens with avirulent *Salmonella* vaccine strain carrying *C. jejuni* 72Dz/92 cjaA gene elicits specific humoral immune response associated with protection against challenge with wild-type *Campylobacter*. Vaccine 22, 1379-89.
189. Yamaguchi, T., Iritani, Y., and Hayashi, Y. (1988) Serological response of chickens either vaccinated or artificially infected with *Haemophilus paragallinarum*. Avian Dis. 32, 308-12.
190. Yasuda, J., Nakada, S., Kato, A., Toyoda, T., and Ishihama, A., (1993) Molecular assembly of influenza virus: association of the NS2 protein with virion matrix. Virology 196, 249-255.
191. York, J. J., Strom, A. D., Connick, T. E., McWaters, P. G., Boyle, D. B., and Lowenthal, J. W. (1996) In vivo effects of chicken myelomonocytic growth factor: delivery via a viral vector. J. Immunol. 156, 2991-7.
192. Yoshida, S., Lee, L. F., Yanagida, N., and Nazerian, K. (1994) Identification and characterization of a Marek's disease virus gene homologous to glycoprotein L of herpes simplex virus. Virology 204, 414-9.
193. Young, J. F., and Palese, P. (1979) Evolution of human influenza A viruses in nature. Recombination contributes to genetic variation of H1N1 strains. Proc. Natl. Acad. Sci. USA 76, 6547-6551.
194. Zebedeem S. L., and Lamb, R. A. (1988) Influenza A virus M2 protein: monoclonal antibody restriction of virus growth and detection of M2 in virions. J. Virol. 62, 2762-2772.
195. Zeng, M., Smith, S. K., Siegel, F., Shi, Z., Van Kampen, K. R., Elmets, C. A., and Tang, D. C. (2001). AdEasy system made easier by selecting the viral backbone plasmid preceding homologous recombination. Biotechniques 31, 260-262.

---

What is claimed is:

1. A method of introducing and expressing one or more avian antigens or immunogens in an avian embryo, comprising administering a recombinant human adenovirus expression vector that comprises and expresses a human adenoviral DNA sequence, and a promoter sequence operably linked to a foreign sequence encoding one or more avian antigens or immunogens of interest into an amnion-allantois space of an embryonated avian egg, thereby obtaining expression of the one or more avian antigens or immunogens in the avian embryo.

2. The method of claim 1, wherein the adenovirus expression vector is a replication competent adenovirus (RCA) free recombinant human adenovirus expression vector.

3. The method of claim 1, wherein the adenovirus expression vector is E1 and/or E3 defective adenovirus serotype 5 (Ad5).

4. The method of claim 1, wherein the one or more avian antigens or immunogens of interest are derived from avian influenza virus, infectious bursal disease virus, Marek's disease virus, avian herpesvirus, infectious laryngotracheitis virus, avian infectious bronchitis virus, avian reovirus, avipox, fowlpox, canarypox, pigeonpox, quailpox, and dovepox, avian polyomavirus, Newcastle Disease virus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, or avian spleen necrosis virus.

5. The method of claim 1, wherein the foreign sequence encoding the one or more avian antigens or immunogens of interest is derived from avian influenza, wherein the avian influenza antigens or immunogens are selected from the group consisting of hemagglutinin, nucleoprotein, matrix, or neuraminidase.

6. A method for inoculation of an avian subject, comprising administration, into an amnion-allantois space of an embryonated avian egg, of a recombinant human adenovirus containing and expressing an heterologous nucleic acid molecule encoding an antigen of a pathogen of the avian subject.

7. The method of claim 6, wherein the human adenovirus comprises sequences derived from replication-defective adenovirus, non-replicating adenovirus, replication-competent adenovirus, or wild-type adenovirus.

8. The method of claim 6, wherein the antigen of a pathogen of the avian is derived from avian influenza, wherein the avian influenza antigens or immunogens are selected from the group consisting of hemagglutinin, nucleoprotein, matrix, or neuraminidase.

9. A method of inducing an immune response to avian influenza in an avian, comprising:

administering in ovo to an avian a recombinant human adenovirus expression vector expressing one or more avian influenza antigens, wherein the administering in ovo is into the amnion-allantois space, and wherein induction of the immune response provides protection against challenge with avian influenza virus.

10. The method of claim 9, wherein the adenovirus expression vector expressing one or more avian influenza antigens is administered at a dose of about $1\times10^8$ to about $1\times10^{11}$ pfu per egg or an equivalent dose measured by ifu or an equivalent dose measured by virus particles.

11. The method of claim 9, wherein the adenovirus expression vector expressing one or more avian influenza antigens is administered at a dose of about $5\times10^{10}$ pfu per egg or about at a dose of $2\times10^8$ ifu per egg or at a dose of about $3\times10^{10}$ viral particles per egg.

12. The method of claim 9, wherein the immune response provides protection from a different influenza subtype than was administered in ovo.

13. The method of claim 9, wherein the avian is administered a second dose of the recombinant human adenovirus expression vector expressing one or more avian influenza antigens post hatch.

14. The method of claim 13, wherein the second dose is administered about 2-weeks to about 4-weeks post hatch.

15. The method of claim 13, wherein the second dose is administered intra-muscularly or intranasally.

16. The method of claim 9, wherein the avian is a chicken.

17. The method of claim 9, wherein the one or more avian antigens are selected from the group consisting of hemagglutinin, nucleoprotein, matrix, or neuraminidase.

18. The method of claim 9, wherein immunomodulatory molecules are co-administered with the one or more avian influenza antigens to the avian.

19. The method of claim 9, wherein the adenovirus expression vector is E1 and/or E3 defective adenovirus serotype 5 (Ad5).

* * * * *